US010994013B2

(12) United States Patent
Thakare et al.

(10) Patent No.: US 10,994,013 B2
(45) Date of Patent: May 4, 2021

(54) SOLID DOSAGE FORM CONTAINING ARABINOGALACTAN

(71) Applicant: TEMPLE UNIVERSITY—OF THE COMMONWEALTH SYSTEM OF HIGHER EDUCATION, Philadelphia, PA (US)

(72) Inventors: Kalpana N. Thakare, Lansdale, PA (US); David B. Lebo, Warminster, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 14/784,079

(22) PCT Filed: Apr. 24, 2014

(86) PCT No.: PCT/US2014/035225
§ 371 (c)(1),
(2) Date: Oct. 13, 2015

(87) PCT Pub. No.: WO2014/176389
PCT Pub. Date: Oct. 30, 2014

(65) Prior Publication Data
US 2016/0058868 A1 Mar. 3, 2016

Related U.S. Application Data

(60) Provisional application No. 61/815,333, filed on Apr. 24, 2013.

(51) Int. Cl.
A61K 47/36 (2006.01)
A61K 31/192 (2006.01)
A61K 9/16 (2006.01)
A61K 9/14 (2006.01)
A61K 9/50 (2006.01)
A61K 31/4178 (2006.01)
A61K 31/427 (2006.01)
A61K 31/4422 (2006.01)
A61K 31/496 (2006.01)

(52) U.S. Cl.
CPC .............. A61K 47/36 (2013.01); A61K 9/146 (2013.01); A61K 9/1652 (2013.01); A61K 9/5036 (2013.01); A61K 31/192 (2013.01); A61K 31/4178 (2013.01); A61K 31/427 (2013.01); A61K 31/4422 (2013.01); A61K 31/496 (2013.01)

(58) Field of Classification Search
CPC .............. A61K 31/192; A61K 31/4178; A61K 31/427; A61K 31/4422; A61K 31/496; A61K 47/36; A61K 9/146; A61K 9/1652; A61K 9/5036
See application file for complete search history.

(56) References Cited

U.S. PATENT DOCUMENTS

| 3,555,151 A | 1/1971 | Kaplan et al. |
| 3,787,327 A | 1/1974 | Emrick |
| 4,228,198 A | 10/1980 | Burge et al. |
| 4,818,542 A | 4/1989 | Deluca et al. |
| 5,288,502 A | 2/1994 | McGinty et al. |
| 5,336,506 A | 8/1994 | Josephson et al. |
| 5,478,576 A * | 12/1995 | Jung .................. A61K 47/4823 424/488 |
| 5,554,386 A | 9/1996 | Groman et al. |
| 5,756,098 A * | 5/1998 | Price .................... C07D 311/40 100/127 |
| 6,086,917 A | 7/2000 | Trubiano et al. |
| 6,087,092 A | 7/2000 | Richards |
| 6,214,378 B1 | 4/2001 | Tanida et al. |
| 6,258,796 B1 | 7/2001 | Richards |
| 6,296,873 B1 * | 10/2001 | Katzhendler ........ A61K 9/2031 424/464 |
| 6,399,086 B1 | 6/2002 | Katzhendler et al. |
| 6,455,053 B1 | 9/2002 | Okada et al. |
| 6,471,992 B1 | 10/2002 | Yoo et al. |
| 6,485,738 B1 | 11/2002 | Huang et al. |
| 6,749,867 B2 | 6/2004 | Robinson et al. |
| 6,881,420 B2 | 4/2005 | Flashner-Barak et al. |

(Continued)

FOREIGN PATENT DOCUMENTS

WO 1989005632 A1 6/1989
WO 1993025239 A1 12/1993
(Continued)

OTHER PUBLICATIONS

FiberAid 2010, http://ethorn.com/wp-content/uploads/2018/10/Lonza-2018.pdf (Year: 2010).*
Sigma Aldrich (diethylenetriaminepentaacetic acid product profile https://www.sigmaaldrich.com/catalog/product/sial/d6518?lang=en&region=US 2020). (Year: 2020).*
Groman et al. (Bioconjugate Chem. 1994, 5, 547-556) (Year: 1994).*
PCT/US2014/035225 International Search Report and Written Opinion of the International Searching Authority (dated Sep. 4, 2014).
Medvedeva et al, "Mechanical Composites Based on Biologically Active Compounds From Larch Wood," Chemistry of Natural Compounds, 46(2): 212-215 (2010).

(Continued)

Primary Examiner — Anna R Falkowitz
(74) Attorney, Agent, or Firm — Faegre Drinker Biddle & Reath LLP

(57) ABSTRACT

Provided is a dosage form for delivery of a therapeutic agent comprising a polymer matrix comprising arabinogalactan and a therapeutic agent uniformly dispersed in said polymer matrix. In some embodiments, the dosage form is selected from the group consisting of a microsphere, a nanosphere, a powder, a tablet, a film or a pellet enclosed in a capsule. Also provided are methods for preparing the dosage form.

34 Claims, 77 Drawing Sheets

(56) References Cited

U.S. PATENT DOCUMENTS

| | | | |
|---|---|---|---|
| 7,655,697 | B2 | 2/2010 | Franc et al. |
| 7,803,930 | B2 | 9/2010 | Crooke et al. |
| 8,252,322 | B2 | 8/2012 | Trubiano et al. |
| 9,011,920 | B2 | 4/2015 | Meier et al. |
| 9,114,072 | B2 | 8/2015 | Yoo et al. |
| 2003/0133975 | A1 | 7/2003 | Yoo et al. |
| 2004/0013731 | A1 | 1/2004 | Chen et al. |
| 2004/0234602 | A1* | 11/2004 | Fischer ............... A61K 9/0004 424/473 |
| 2004/0234608 | A1 | 11/2004 | Fleshner-Barak et al. |
| 2004/0242770 | A1 | 12/2004 | Feldstein et al. |
| 2006/0246127 | A1 | 11/2006 | Freier |
| 2007/0026075 | A1 | 2/2007 | Shudo et al. |
| 2007/0202232 | A1 | 8/2007 | Habich et al. |
| 2007/0275060 | A1 | 11/2007 | Befumo et al. |
| 2008/0234352 | A1 | 9/2008 | Fischer et al. |
| 2009/0230013 | A1 | 9/2009 | Born et al. |
| 2009/0269397 | A1 | 10/2009 | Saltzman et al. |
| 2010/0168074 | A1 | 7/2010 | Culligan et al. |

FOREIGN PATENT DOCUMENTS

| | | |
|---|---|---|
| WO | 1998036738 A1 | 8/1998 |
| WO | 1999021534 A1 | 5/1999 |
| WO | 2002000213 A1 | 1/2002 |
| WO | 2003087323 A2 | 10/2003 |

OTHER PUBLICATIONS

Medvedeva et al, "Structural Transformations of Arabinogalactan from the Siberian Larch during Mechanochemical Processing and the Biological Properties of the Products," Russian Journal of Bioorganic Chemistry, 36(7): 853-859 (2010).

Falk et al, "A Novel Injectable Water-Soluble Amphotericin B-Arabinogalactan Conjugate," Antimicrobial Agents and Chemoherapy, 43(8): 1975-1981 (Aug. 1999).

Nazareth et al, "Studies on Larch Arabogalactan I," Journal of Pharmaceutical Sciences, 50(7): 560-563 (Jul. 1961).

Nazareth et al, "Studies on Larch Arabogalactan II," Journal of Pharmaceutical Sciences, 50(7): 564-567 (Jul. 1961).

Kaneo et al, "Pharmacokinetics and biodisposition of fluorescein-labeled arabinogalactan in rats," International Journal of Pharmaceutics, 201: 59-69 (2000).

Enriquez et al, "Conjugation of Adenine Arabinoside 5'-Monophosphate to Arabinogalactan: Synthesis, Characterization, and Antiviral Activity," Bioconjugate Chem., 6(2): 195-202 (1995).

Udani et al, "Proprietary arabinogalactan extract increases antibody response to the pneumonia vaccine: a randomized, double-blind, placebo-controlled, pilot study in healthy volunteers," Nutrition Journal, 9:32 (seven pages), (2010).

Dushkin et al, "Mechanochemical preparation and pharmacological activities of water-soluble intermolecular complexes of arabinogalactan with medicinal agents," Russian Chemical Bulletin, International Edition, 57(6): 1299-1307 (Jun. 2008).

Badykova et al, "Arabinogalactan Poly- and Oligosaccharides Modified With 5-Aminosalicylic Acid," Chemistry of Natural Compounds, 41(3): 272-275 (2005).

Singh, "Modified-Release Solid Formulations for Colonic Delivery," Recent Patents on Drug Delivery & Formulation 2007, 1(1): 53-63 (2007).

Fitzpatrick et al, "Larch arabinogalactan: A novel and multifunctional natural product," AgroFOOD industry hi-tech—Special Highlight: Prebiotics & Probiotics, 30-32 (Jan./Feb. 2004).

Szafraniec et al., 2018, "Molecular Disorder of Bicalutamide-Amorphous Solid Dispersions Obtained by Solvent Methods," Pharmaceutics, 10(4):194. doi: 10.3390/pharmaceutics10040194.

Baghel et al., 2016, "Polymeric Amorphous Solid Dispersions: A Review of Amorphization, Crystallization, Stabilization, Solid-State Characterization, and Aqueous Solubilization of Biopharmaceutical Classification System Class II Drugs," Journal of Pharmaceutical Sciences, 105:2527-2544.

* cited by examiner

X-10 IBU AG PM
Y-20 IBU AG PM
Z-30 IBU AG PM

SOLID DOSAGE FORM CONTAINING ARABINOGALACTAN

CROSS REFERENCE TO RELATED APPLICATION

This application claims the benefit of U.S. Provisional Application No. 61/815,333, filed Apr. 24, 2013, the entire disclosure of which is incorporated herein by reference.

FIELD OF THE INVENTION

The invention relates to a solid dosage form containing arabinogalactan.

BACKGROUND OF THE INVENTION

Solid Dispersion

A solid dispersion (SD) of a pharmaceutical active agent results in the dispersion of one or more active ingredients in an inert carrier matrix at solid state prepared by the melting (fusion), solvent, or melting-solvent method. (Chiou and Riegelman, 1971, J. Pharm Sci 60(9):1281-1302). The active ingredient may exist in the SD in finely crystalline, solubilized or amorphous form (Chiou and Riegelman, 1971, J. Pharm Sci 60(9):1281-1302).

First Generation Solid Dispersion

First generation SDs were produced in the decade of the 1960s to obtain faster drug dissolution rates. They are characterized by the use of crystalline carriers such as sugar, urea etc., and were formed mostly as eutectic mixtures. First generation SDs provided enhanced dissolution and bioavailability of poorly water soluble drugs, primarily by particle size reduction and wettability. (Vasconcelos et al., 2007, Drug Discov Today 12(23-24):1068-1075). Chloramphenicol-urea eutectic mixture is one example of a first generation SD. (Goldberg et al., 1966, J Pharm Sci 55(6):581-583).

Second Generation Solid Dispersion

Second generation SDs were produced to overcome the disadvantages of first generation crystalline SDs which would not release the contained drug quickly enough for some applications. Second generation SDs have made use of semi-synthetic amorphous polymers or natural product-based amorphous polymers to molecularly disperse drug in the SD. The formation of the amorphous form of the drug, decreasing the particle size to the molecular level, increased wettability and dispersability by the amorphous polymer. As a result, drug dissolution was enhanced. (Vasconsuelos et al., 2007, Drug Discov Today 12(23-24):1068-1075). For example, a troglitazone-PVP K30 SD has achieved enhanced troglitazone dissolution by forming amorphous troglitazone. (Hasegawa et al., 2006, Int J Pharm 302:103-112).

Third Generation Solid Dispersion

Third generation SDs were produced with the intention of avoiding drug recrystallization, precipitation, and formation of fine crystalline drug precipitate. The precipitate would otherwise form agglomerations in the SD. This has enabled third generation SDs to achieve a high degree of bioavailability of poorly water soluble drug. Third generation SDs are produced using either a carrier with surface activity or a mixture of polymers (Vasconsuelos et al., 2007, Drug Discov Today 12(23-24):1068-1075). For example, a Piroxican gelucire 44/14 SD enhanced in vitro dissolution and in vivo bioavailability (Yuksel et al., 2003, Eur J Pharm Biopharm 56:453-459). Also, a felodipine-HPMC-poloxamer SD has achieved rapid dissolution (Dong-Han Won et al., 2005, Int J Pharm 301(1-2):199-208).

Larch Arabinogalactan

Larch arabinogalactan, a natural and biodegradable polymer is derived from the wood species of genus larex, also known as the larch tree. Larch arabinogalactan is a long and densely branched pure polysaccharide (MW-10,000-120,000) (Di Colo et al., 2009, Drug Dev Ind Pharm 35(8):941-949). Larch arabinogalactan comprises 98% of arabinogalactan and consists of two main monosaccharides, galactose and arabinose, in a ratio of 6:1. Larch arabinogalactan also contains a very small amount of glucuronic acid and mannose as well as traces of glucose and xylose. Larch arabinogalactan has very low microbial content. In the United States, it is categorized as GRAS (generally recognized as safe) and is approved by the FDA for use as a dietary fiber and immune enhancer. It is stable over a wide range of temperatures and pH values.

There remains a need for a solid dosage form comprising a natural polymer for enhancing the dissolution of poorly soluble drugs.

SUMMARY OF THE INVENTION

Provided is a dosage form for delivery of a therapeutic agent comprising a polymer matrix comprising arabinogalactan and a therapeutic agent uniformly dispersed in said polymer matrix.

In some embodiments, the dosage form is selected from the group consisting of a microsphere, a nanosphere, a powder, a tablet, a film or a pellet enclosed in a capsule.

In some embodiments, the dosage form is an oral dosage form.

In some embodiments, the relative degree of crystallinity of the therapeutic agent in the dosage form as compared to that of neat therapeutic agent is equal to or less than 0.20 as measured by X-ray diffraction. In some embodiments, the relative degree of crystallinity of the therapeutic agent in the dosage form as compared to that of neat therapeutic agent is equal to or less than 0.15, 0.1 or 0.05 as measured by X-ray diffraction.

In some embodiments, the therapeutic agent is substantially completely amorphous. This means that the therapeutic agent has no measurable crystallinity left as measured by X-ray diffraction.

In some embodiments, the therapeutic agent has no measurable crystallinity left as measured by Thermomechanical Analysis (TMA).

In some embodiments, the therapeutic agent is a therapeutic agent having low solubility in water and high permeability or a therapeutic agent having low solubility in water and low permeability. In further embodiments, the therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, cimetidine, ketoconazole and furesamide.

FTIR shows no detectable covalent bonding of the therapeutic agent to the polymer matrix. In further embodiments, FTIR shows non-covalent bonding of the therapeutic agent to the polymer matrix. In yet further embodiments, the therapeutic agent forms hydrogen bonds to the polymer matrix.

In some embodiments the dosage form is prepared by dissolving arabinogalactan in a solvent, followed by emulsion-solvent evaporation of a solvent for the polymer matrix comprising arabinogalactan.

In some embodiments the dosage form is prepared by dissolving arabinogalactan in a solvent, followed by solvent evaporation of a solvent for the polymer matrix comprising arabinogalactan.

In some embodiments the relative degree of crystallinity of the therapeutic agent in the dosage form as compared to that of neat therapeutic agent after at least 3 months of storage of the dosage form is less than the initial relative degree of crystallinity of the therapeutic agent in the dosage form as compared to that of neat therapeutic agent. In some embodiments the relative degree of crystallinity of the therapeutic agent in the dosage form as compared to that of neat therapeutic agent after at least 3 months of storage at 40° C. and 75% relative humidity, and 25° C. and 60% relative humidity for 6 months of the dosage form is less than the initial relative degree of crystallinity of the therapeutic agent in the dosage form as compared to that of neat therapeutic agent. In some embodiments the therapeutic agent in the dosage form is physically stable upon exposure to accelerated storage conditions.

In some embodiments the percentage drug load of the therapeutic agent in the polymer matrix comprising arabinogalactan is between about 10% and about 40% by weight. In some embodiments the percentage drug load of the therapeutic agent in the polymer matrix comprising arabinogalactan is between about 10% and about 20% by weight. In further embodiments, the percentage drug load of the therapeutic agent in the polymer matrix comprising arabinogalactan is about 10%, about 20%, about 30% or about 40% by weight. In yet further embodiments, the drug load is less than or equal to about 20% by weight, or less than or equal to about 10% by weight.

In some embodiments, the dissolution for % drug release at 15 minutes is from about 1.5 fold to about 55 fold when compared to that of neat therapeutic agent and wherein the percentage drug load of the therapeutic agent in the polymer matrix comprising arabinogalactan is between about 10% and about 30% by weight. In further embodiments, the dissolution enhancement for % drug release at 15 minutes is from about 8 fold to about 55 fold when compared to that of neat therapeutic agent and wherein the percentage drug load of the therapeutic agent in the polymer matrix comprising arabinogalactan is between about 10% and about 20% by weight. In yet further embodiments, the dissolution enhancement for % drug release at 15 minutes is from about 11 fold to about 48 fold when compared to that of neat therapeutic agent and wherein the percentage drug load of the therapeutic agent in the polymer matrix comprising arabinogalactan is about 10% by weight.

Provided is a method for preparing a dosage form comprising the steps of dissolving a therapeutic agent in a solvent to form a first solution of the therapeutic agent; adding the therapeutic agent solution to an arabinogalactan-water wet mass to form a second solution; and evaporating the water and solvent from the second solution to obtain a dosage form comprising a polymer matrix comprising arabinogalactan and the therapeutic agent dispersed in the polymer matrix. In some embodiments, the dosage form is a microsphere, a nanosphere, or a powder. In some embodiments, the dosage form is an oral dosage form. In further embodiments, the microsphere has a diameter of from about 100 μm to about 500 μm. In some embodiments the solvent is ethanol.

Provided is a method for preparing a dosage form comprising the steps of mixing arabinogalactan and a therapeutic agent to form a physical mixture; adding water to the physical mixture to obtain a wet mass; adding a solvent to the wet mass; and evaporating the water and solvent from the solution to obtain a dosage form comprising a polymer matrix comprising arabinogalactan and the therapeutic agent dispersed in the polymer matrix. In some embodiments, the dosage form is a microsphere, a nanosphere, or a powder. In some embodiments, the dosage form is an oral dosage form. In further embodiments, the microsphere has a diameter of from about 100 μm to about 500 μm. In some embodiments the solvent is ethanol.

Provided is a method for preparing a dosage form comprising the steps of suspending a therapeutic agent in an aqueous solution of arabinogalactan to form a solution; heating the solution near the melting point of the therapeutic agent; emulsifying the solution with an oil to form a water in oil emulsion; and evaporating the water from the solution to obtain a dosage form comprising a polymer matrix comprising arabinogalactan and the therapeutic agent dispersed in the polymer matrix. In some embodiments, the dosage form is a microsphere, a nanosphere, or a powder. In some embodiments, the dosage form is an oral dosage form. In further embodiments, the microsphere has a diameter of from about 100 μm to about 500 μm. In some embodiments the oil is safflower oil.

In some embodiments of any one of the previously described methods, the therapeutic agent is a therapeutic agent having low solubility and high permeability or a therapeutic agent having low solubility and low permeability. In further embodiments, the therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, ketoconazole and furesamide.

FTIR shows no detectable covalent bonding of the therapeutic agent to the polymer matrix. In further embodiments of any one of the previously described methods, FTIR shows non-covalent bonding of the therapeutic agent to the polymer matrix. In yet further embodiments, the therapeutic agent forms hydrogen bonds with the polymer matrix.

In some embodiments the percentage drug load of the therapeutic agent in the polymer matrix comprising arabinogalactan is from about 10% to about 40% by weight. In some embodiments the percentage drug load of the therapeutic agent in the polymer matrix comprising arabinogalactan is from about 10% to about 20% by weight. In further embodiments, the percentage drug load of the therapeutic agent in the polymer matrix comprising arabinogalactan is about 10%, about 20%, about 30% or about 40% by weight. In yet further embodiments, the drug load is less than or equal to about 20% by weight, or less than or equal to about 10% by weight.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

BRIEF DESCRIPTION OF THE DRAWINGS

FIG. 5A shows the surface of the MSDs. FIG. 5B shows a cross-section of the MSDs.

FIG. 6A shows the surface of the MSDs. FIG. 6B shows the cross-section of the MSDs.

FIG. 7A shows the surface of the MSDs. FIG. 7B shows the cross-section of the MSDs.

DEFINITIONS

Figure 1:
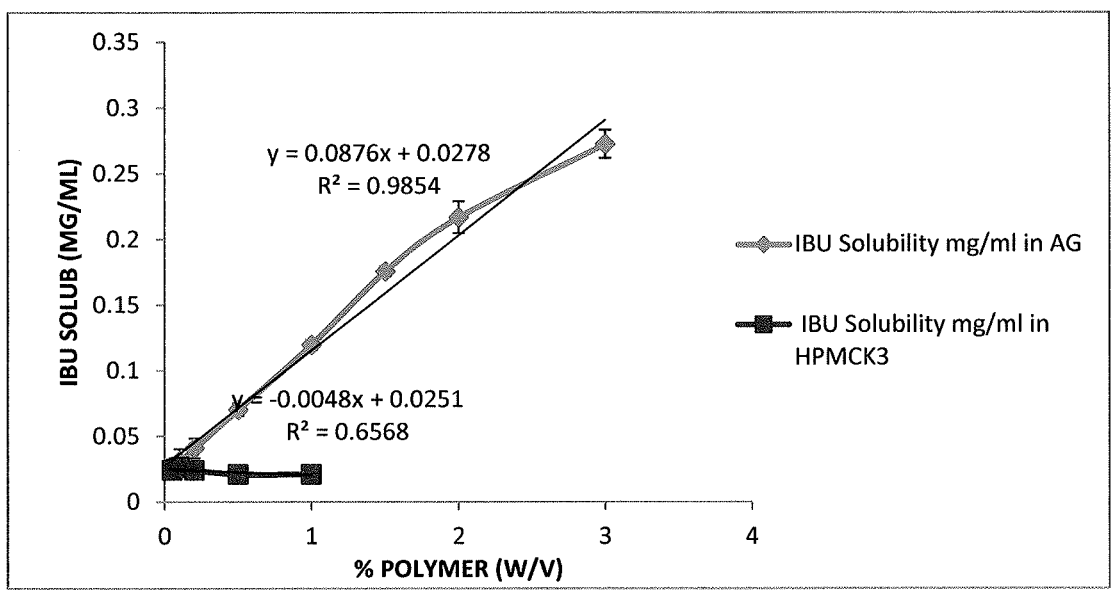
FIG. 1 shows the effect of arabinogalactan (AG) concentration on ibuprofen (IBU) solubility in 0.1N HCl, in comparison to IBU solubility contained in hydroxypropyl methyl cellulose K3 (HPMCK3).

As used herein, each of the following terms has the meaning associated with it in this section.

The articles "a" and "an" are used herein to refer to one or to more than one (i.e. to at least one) of the grammatical object of the article. By way of example, "an element" means one element or more than one elements.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "arabinogalactan," as used herein, describes a polymer comprising arabinose and galactose. In preferred embodiments, the arabinogalactan is larch arabinogalactan. The term "larch arabinogalactan," as used herein, describes a natural and biodegradable polymer derived from the wood species of genus larex, also known as the larch tree. It is a long and densely branched pure polysaccharide (MW 10,000-120,000). Larch arabinogalactan is comprised 98% of arabinogalactan and consists of two main monosaccharides, galactose and arabinose, in a ration of 6:1. It also contains a very small amount of glucuronic acid and mannose as well as traces of glucose and xylose. It has very low microbial content. In the United States, it is categorized as GRAS (generally recognized as safe) and is approved by the FDA for use as a dietary fiber and immune enhancer.

In especially preferred embodiments, the arabinogalactan is larch arabinogalactan Fiberaid™ grade. Larch arabinogalactan Fiberaid® grade may be obtained from Lonza, New Jersey, USA.

The term "therapeutic agent," as used herein, describes a drug for use in the treatment of a disease or medical condition. In some embodiments, the drug is a water soluble drug. In some preferred embodiments, the drug is a poorly water soluble drug. In further preferred embodiments, the poorly water soluble drug is an anti-fungal drug, an anti-viral drug, a calcium channel blocker, a beta blocker drug or a sulfonylurea antidiabeteic drug.

The term "polymer matrix," as used herein, describes a three-dimensional structure comprising a polymer. A polymer matrix is not a mere physical mixture, but rather it describes a structure where the polymer has formed a network and it the therapeutic agent is uniformly dispersed in the network. In the dosage forms of the present invention, the polymer matrix comprises arabinogalactan, and a therapeutic agent is uniformly dispersed in the polymer matrix.

The term "dispersed," as used herein with respect to the dosage forms of the present invention, describes being distributed or spread out throughout the arabinogalactan polymer matrix. The term "uniformly dispersed," as used herein with respect to the dosage forms of the present invention, describes being distributed or spread out throughout the polymer matrix in roughly equal amounts. The term "uniformly dispersed" as used with respect to the dosage forms of the present invention, does not encompass having the therapeutic agent substantially incorporated in walls and channels of the polymer or located in pores, cavities or pockets of the polymer.

The term "substantially completely amorphous," as used herein with respect to the dosage forms of the present invention means that the therapeutic agent has no measurable crystallinity left as measured by X-ray diffraction.

The term "low water solubility," as used herein, describes compounds including those that are considered "slightly soluble" (100 to 1000 parts solvent needed to dissolve 1 part solute), "very slightly soluble" (1000 to 10,000 parts solvent needed to dissolve 1 part solute), and "practically insoluble" (more than 10,000 parts solvent needed to dissolve 1 part solute), according to the United States Pharmacopeia (USP).

The term "permeability," as used herein and as applied to a therapeutic agent means the extent of the agent's absorption (fraction of dose absorbed) in humans by mass transfer across a human intestinal membrane. The term "high permeability," as used herein, thus describes agents with a high extent of absorption by mass transfer across the human intestinal membrane. The term "low permeability," as used herein, describes compounds with a low extent of absorption in humans and having a low rate of mass transfer across human intestinal membrane. The rate of mass transfer across human intestinal membrane can be determined in vitro, for example by employing epithelial cell culture methods that are known in the art.

The term "relative degree of crystallinity (RDC)," as used herein is the degree of crystallinity of the therapeutic agent in the dosage form relative to the degree of crystallinity of the neat therapeutic agent. RDC is calculated using the following formula:

$$RDC = I\text{ sample}/I\text{ therapeutic agent}$$

I sample: peak height of the formulation under investigation at a chosen angle (2θ)
I therapeutic agent: peak height of the neat therapeutic agent at the same angle that was chosen for the sample (2θ)

The term "modified water in oil emulsion solvent evaporation," as used herein, describes a process for preparing the microsphere solid dispersions (MSDs) disclosed herein. A therapeutic agent is suspended in an aqueous solution of arabinogalactan. This drug arabinogalactan solution is heated just near the melting point of the therapeutic agent. This solution is then emulsified with an oil. The water is then evaporated.

ABBREVIATIONS

AG: Larch arabinogalactan
AGF: Larch arabinogalactan FIBERAID grade
IBU: Ibuprofen
ITRA: Itraconazole
KETO: Ketoprofen
SD: Solid dispersions
HM: Hot Mix
IPSD: Innerphase solid dispersion
SBHM: Sand bath hot mix FRZD: Freezedried
SPRDY: Spray dried
SEWS: Solvent evaporation with water as a solvent
DL: Drug load
HPMC: Hydroxypropyl methyl cellulose
HPMCK3: Hydroxypropyl methyl cellulose K3
HPMCAS: Hydroxypropylmethylcellulose acetate succinate
% DR 15 min: % drug release at 15 min
% DR 30 min: % drug release at 30 min
% DR 120 min: % drug release at 120 min
PM: Physical mixture
SDM: Solid dispersion prepared by modified solvent evaporation method
MSD: microsphere solid dispersion
SDM: modified solvent evaporation method
TMA: thermomechanical analysis
CHLORP: Chlorpropamide
DSC: Differential scanning calorimetry (conventional)
E100: Eudragit E100
FLURBI: Flurbiprofen
FUROS: Furosemide
FTIR: Fourier transform infrared spectroscopy
KETOC: Ketoconazole
LC-MS: Liquid chromatography mass spectroscopy
NAPROX: Naproxen
NIMO: Nimodipine
PROPFB: Propranolol free base
PROPHCI: Propranolol hydrochloride
PAA: Poly (acrylic acid)
PSSA: Poly (styrene sulfonic acid)
PVP: Poly (vinylpyrrolidone)
PVPVA: Poly (vinylpyrrolidone-vinyl acetate)
RC: Relative crystallinity
RDC: Relative degree of crystallinity
RITO: Ritonavir
TIOCO: Triconazole
XRPD: Xray powder diffractogram (XRPD)
FENOP: Fenoprofen
CIMET: Cimetidine The convention for the dosage forms that is used in the figures and in the text is: X % DRUG POLYMER DOSAGE. For example "30 IBU AGF PM" means a 30% drug load of ibuprofen in an arabinogalactan physical mixture.

DETAILED DESCRIPTION OF THE INVENTION

The dosage forms of the present invention comprising arabinogalactan, a natural and biodegradable polymer, enhance the dissolution of poorly soluble drugs.

The dosage form disclosed herein confers many advantages over known dosage forms. The dosage form provided herein results in a significantly higher drug dissolution in water at stomach pH compared to neat therapeutic agents and mere physical mixtures of a therapeutic agent with arabinogalactan. The arabinogalactan polymer also increases therapeutic agent solubility in water significantly due to its low viscosity and hydrophilic nature. The dosage form provided herein results in therapeutic agent dispersion with low crystallinity.

Provided is a dosage form for delivery of a therapeutic agent comprising a polymer matrix comprising arabinogalactan and a therapeutic agent uniformly dispersed in said polymer matrix. In preferred embodiments, the therapeutic agent is not confined or concentrated in channels or pores of the polymer matrix.

In some embodiments, the dosage form is selected from the group consisting of a microsphere, a nanosphere, a powder, a tablet, a film or a pellet enclosed in a capsule. In further embodiments the dosage form is an oral dosage form.

Arabinogalactan

Arabinogalactan is a polymer comprising arabinose and galactose. In preferred embodiments, the arabinogalactan is larch arabinogalactan. Larch arabinogalactan describes a natural and biodegradable polymer derived from the wood species of genus larex, also known as the larch tree. It is a long and densely branched pure polysaccharide (MW 10,000-120,000). Larch arabinogalactan is comprised 98% of arabinogalactan and consists of two main monosaccharides, galactose and arabinose, in a ration of 6:1. The chemical name of larch arabinogalactan is L-arabino-D-galactan. It also contains a very small amount of glucuronic acid and mannose as well as traces of glucose and xylose. It has very low microbial content. In the United States, it is categorized as GRAS (generally recognized as safe) and is approved by the FDA for use as a dietary fiber and immune enhancer.

In especially preferred embodiments, the arabinogalactan is larch arabinogalactan Fiberaid® grade. Larch arabinogalactan Fiberaid® grade may be obtained from Lonza, New Jersey, USA.

Solid Dispersion Dosage Forms

The dosage forms of the present invention are solid dispersions. A solid dispersion is the dispersion of one or more therapeutic agents in a polymer matrix at solid state (Chiou and Riegelman, 1971, *J. Pharm Sci* 60(9):1281-1302). There are many methods for preparing solid dispersions, some of which are outlined below.

In the solid dispersions of the present invention, a therapeutic agent is uniformly dispersed in a polymer matrix comprising arabinogalactan. In some embodiments of the solid dispersions of the present invention, the therapeutic agent is in a substantially completely amorphous form. In further embodiments of the solid dispersions of the present invention, the therapeutic agent is in a completely amorphous form. In preferred embodiments, the therapeutic agent is not confined or concentrated in channels or pores of the polymer matrix.

The amorphous form of the drug does not require energy to break the crystal lattice of the drug and thus has the highest solubility, which in turn leads to a faster dissolution rate. Upon dissolution, a supersaturated solution of the drug is produced which enhances the bioavailability of the drug. Even if drug precipitates out from this supersaturated solution, it seems to form a metastable polymorphic form with higher solubility than its crystalline form (Chiou and Riegelman, 1971, *J. Pharm Sci* 60(9):1281-1302).

Some solid dispersion preparation methods for preparing the dosage forms of the present invention comprising arabinogalactan and a therapeutic agent are described below. However, a skilled artisan will recognize that there may be other methods for preparing solid dispersions that will produce the solid dosage forms of the present invention. Although AGF was used for the methods and examples described below, a skilled artisan would recognize that other forms of arabinogalactan may also be used to prepare the dosage forms of the present invention.

Solid Dispersion with Modified Solvent Evaporation Method (SDM)

The modified solvent evaporation method described by Rane et al., 2007, *AAPS PharmSciTech* 8(2): Article 27, and Karavas et al., 2001, *Trends in Colloid and Interface Science XV Progress in Colloid and Polymer Science* 118: 149-152, may be used to prepare SDMs with arabinogalactan fiberaid grade (AGF). Few modifications were made to the method. Drug is dissolved in ethanol using stirring until a clear solution is obtained (below saturation solubility). Polymer is placed in a round bottom flask. Sufficient nanopure water is added to the polymer to obtain a polymer wet mass. The drug-ethanol solution is added to the polymer wet mass at once. The AGF precipitates out due to the presence of ethanol. The entire solvent is evaporated at 70° C. under vacuum using a rotavap. It takes 45 minutes to 2 hours to obtain a dried mass. To ensure complete drying, the flask is kept in an oven at 45° C. overnight. The prepared SDMs are stored in an airtight container.

A slightly modified method may be used for drugs for which a saturated solution could not be obtained with a workable ethanol volume to process an adequate amount of solid dispersion. A physical mixture of AGF with drug is placed in a round bottom flask. Nanopure water is added to the physical mixture to obtain a wet mass. 5-7 ml of ethanol is added at once to this polymer mass. The entire solvent is removed using rotovap evaporation at 70° C. under vacuum. It takes 45 minutes to 2 hours (depending on the drug load) to obtain the desired SDM mass. To ensure complete drying, the SDM samples are kept in an oven at 45° C. overnight. The prepared SDM samples are stored in an airtight container until further analysis.

Microsphere Solid Dispersions (MSDs)

In preferred embodiments, the dosage form is a microsphere, or a microsphere solid dispersion (MSD). Therapeutic agent-loaded AGF MSDs of various drug loads (DLs) may be prepared by a modified water-in-oil emulsion solvent evaporation technique. The therapeutic agent is dispersed in a 28%-36% aqueous solution of arabinogalactan. This drug-arabinogalactan solution is heated just near the melting point of the therapeutic agent. This leads to formation of a viscous inner phase comprising molten therapeutic agent and outer oily phase. In addition, this viscous inner phase prevents the partitioning of the hydrophobic therapeutic agent into the outer oily phase. The thick inner viscous phase is then emulsified with an oil at room temperature. In preferred embodiments, the oil is safflower oil. After evaporation of the remaining water from the inner phase, solidified microspheres are obtained. After washing with HPLC grade acetone, the microspheres are subjected to thorough drying. For example, the microspheres are first dried at room temperature followed by drying in an oven at 45° C. overnight.

Therapeutic Agents that May be Delivered by the Presently Provided Dosage Forms

Various therapeutic agents may be dispersed in arabinogalactan polymer to form the dosage forms of the present invention. In some embodiments, the therapeutic agent is a therapeutic agent having low solubility and high permeability or a therapeutic agent having low solubility and low permeability. In some embodiments the therapeutic agent is acidic and forms hydrogen bonds with arabinogalactan polymer. In further embodiments the therapeutic agent is neutral and has a carbonyl group that may form hydrogen bonds with arabinogalactan polymer. In yet further embodiments, the therapeutic agent is basic and forms acid-base interactions with arabinogalactan polymer. In some embodiments the therapeutic agent has an inherent tendency to form glass and consequently forms an amorphous solid dispersion with arabinogalactan polymer.

The therapeutic agent having low solubility may be, for example, an anti-fungal drug, anti-viral drug, calcium channel blocker, beta blocker drug or a sulfonylurea antidiabetic drug.

The antineoplastic agent may comprise, for example, a differentiating agent, a plant alkaloid or its derivatives, a topoisomerase inhibitor, an anticancer antibiotic or an antimetabolite. In preferred embodiments the differentiating agent is all-trans retinoic acid. In preferred embodiments, the plant alkaloid or plant alkaloid derivative is paclitaxel, docetaxel, etoposide, camptothecin, vinblastine, vincristine, vindesine, vinorelbine or vinoreline. In preferred embodiments, the topoisomerase inhibitor is topotecan or irinotecan. In preferred embodiments the aromatase inhibitor is anastrozole or letrozole. In further preferred embodiments, the anticancer antibiotic is doxorubicin, daunorubicin, valrubicin, bleomycin, dactinomycin, epirubicin, idarubicin, mitoxantrone or mitomycin. In yet further preferred embodiments, the antimetabolite is methotrexate, pemetrexed, raltitrexed, cladribine, clofarabine, fludarabine, mercaptopurine, fluorouracil or gemcitabine.

Steroidal hormones that may be delivered by the presently provided dosage forms comprise, for example, anabolic steroids, corticosteroidal hormones, physiologically equivalent hormone derivatives or combinations thereof. In preferred embodiments, the anabolic steroid is androstenolone, androstenone, nandrolol, nerobolil or retabolil. In further preferred embodiments, the corticosteroidal hormone is betamethasone, dexamethasone, hydrocortisone, progesterone, prednisolone or a fluorinated corticosteroid.

Sex hormones that may be delivered by the presently provided dosage forms comprise, for example, androgens and estrogens. In preferred embodiments, the androgen is testosterone or dihydrotestosterone. In further preferred embodiments, the estrogen is estradiol or norestradiol.

Antiviral agents that may be delivered by the presently provided dosage forms comprise, for example, entry inhibitors, protease inhibitors, integrase inhibitors, maturation inhibitors and CCR5 receptor agonists. In preferred embodiments, the entry inhibitor is maraviroc or enfuvirtide. In further preferred embodiments, the protease inhibitor is saquinavir, ritonavir, indinavir, nelfinavir, amprenavir, lopinavir, atazanavir, fosamprenavir, tipranavir or darunavir. In yet further preferred embodiments, the integrase inhibitor is elvitegravir or raltegravir. In preferred embodiments, the maturation inhibitor is bevirimat. In further preferred embodiments, the CCR5 receptor agonist is aplaviroc or vicriviroc.

Antibiotics that may be delivered by the presently provided dosage forms comprise, for example, aminoglycosides, fluoroquinolones, macrolides, rifampines or tetracyclines. In preferred embodiments, the aminoglycoside is gentamycin, tobramycin, streptomycin or amikacin. In further preferred embodiments, the fluoroquinolone is ciproflaxin, moxifloxacin or gatifloxacin. In yet further preferred embodiments, the macrolide is azithromycin or clarithromycin. In preferred embodiments, the rifampine is rifampicin or rifabutine. In further preferred embodiments, the tetracycline is doxycyclin or minocyclin.

Other therapeutic agents that may be delivered by the presently provided dosage forms comprise, for example, skin whitening agents, sunscreen ingredients and oil-soluble vitamins. In preferred embodiments, the skin whitening ingredient is hydroquinone or monobenzone. In further preferred embodiments, the sunscreen ingredient is avobenzone bemotrizinol, octocrylene, padimate O, octyl salicylate or octyl methoxycinnamate. In yet further preferred embodiments, the oil-soluble vitamin is vitamin D or derivatives thereof, or vitamin E or derivatives thereof.

In further embodiments, the therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, ketoconazole and furesamide.

The chemical structure of ritonavir (RITO) is shown below:

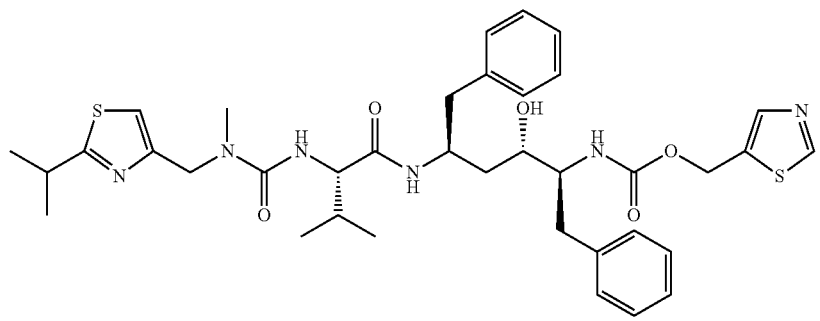 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

The chemical structure of tioconazole is shown below:

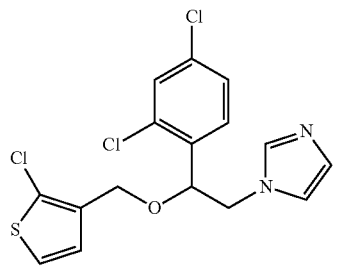 [SMILES: Clc1ccc(C(Cn2ccnc2)OCc2ccsc2Cl)c(Cl)c1]

The chemical structure of furosemide is shown below:

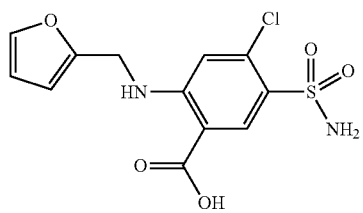 [SMILES: NS(=O)(=O)c1cc(C(=O)O)c(NCc2ccco2)cc1Cl]

The chemical structure of ketoconazole is shown below:

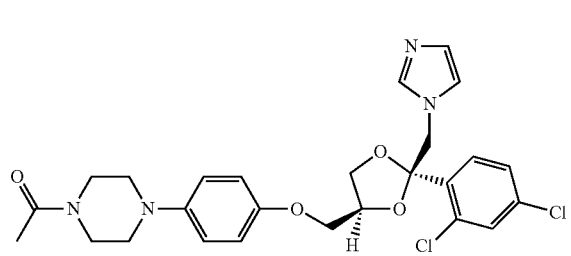 [SMILES: CC(=O)N1CCN(c2ccc(OC[C@H]3CO[C@](Cn4ccnc4)(c4ccc(Cl)cc4Cl)O3)cc2)CC1]

The chemical structure of propranolol free base is shown below:

The chemical structure of naproxen is shown below:

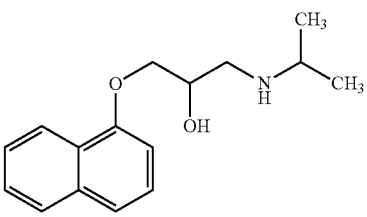 [SMILES: CC(C)NCC(O)COc1cccc2ccccc12]

The chemical structure of flurbiprofen is shown below:

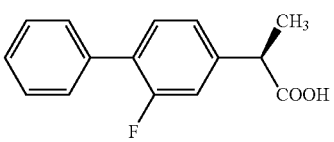 [SMILES: C[C@@H](C(=O)O)c1ccc(-c2ccccc2)c(F)c1]

The chemical structure of nimodipine is shown below:

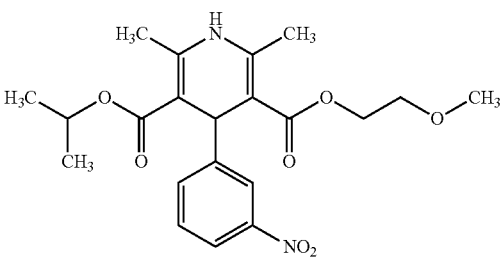 [SMILES: COCCOC(=O)C1=C(C)NC(C)=C(C(=O)OC(C)C)C1c1cccc([N+](=O)[O-])c1]

The chemical structure of chlorpropamide is shown below:

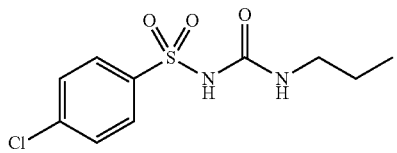 [SMILES: CCCNC(=O)NS(=O)(=O)c1ccc(Cl)cc1]

The chemical structure of fenoprofen is shown below:

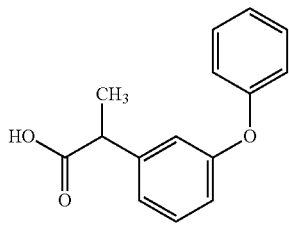 [SMILES: CC(C(=O)O)c1cccc(Oc2ccccc2)c1]

The chemical structure of cimetidine is shown below:

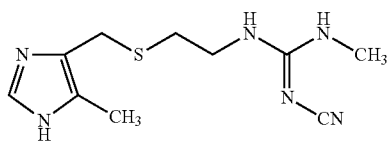 [SMILES: CN/C(=N\C#N)NCCSCc1nc[nH]c1C]

The physical properties of some of the drugs that may be used to prepare AGF solid dispersions are listed in Table 1 below.

TABLE 1

Physical properties of drugs that may be used to prepare AGF solid dispersions.

| Drug | BCS class | Functional group | Acidic/Basic | Solubility |
|---|---|---|---|---|
| RITO (MW 720.95) | BCS class II | Amide, hydroxyl | Basic | 1 μg/ml in distilled water |
| TIOCO (MW 387.7.) | BCS class II | Aliphatic ether | Basic | ~2 μg/ml |
| FUROS (MW 330.7) | BCS class IV | Amino, carboxyl | Basic | 18.25 μg/ml |
| KETOC (MW 531.44) | BCS class II | Carbonyl, aliphatic ether and aromatic ether | Basic | 10 μg/ml |
| PROPFB | High dose BCS class II | Hydroxyl and amino | Basic | 120 μg/ml |
| NAPROX (MW 252.23) | BCS class II | Carboxyl | Acidic | 84 μg/ml 28 μg/ml (0.12 mmole) |
| FLURBI (MW 244.08) | BCS class II | Carboxyl | Acidic | 482 μg/ml |
| NIMO (MW 418.5) | BCS class II | Amino, Nitro, Carbonyl | Neutral | 2299 μg/ml |
| CHLOPR (MW 276.74) | BCS class II | Amide | Acidic | 2500 μg/ml (water at pH 6) |
| Fenoprofen (MW 242.26) | 121.57 | Carboxyl | Acidic | <<<<<<2500 μg/ml (for its calcium salt) |

The melting, fusion enthalpy and Tg/Tm of some of the drugs that may be used to prepare AGF solid dispersions are listed in Table 2 below.

TABLE 2

Melting, fusion enthalpy and Tg/Tm of various drugs.

| Drug | Melting (Tm) (Expt) | Enthalpy of Fusion J/gram (Expt) | Tg | Tg/Tm (K) |
|---|---|---|---|---|
| IBU (MW 206.29) | 76.56 | 135 | −45° C. (228 K) | 0.658 |
| ITRA (MW 705.64) | 169.92 | 92.41 | 58° C. (331.15 K) | 0.747 |
| KETO (MW 254.28) | 96.53 | 80.1 | 3.15° C. 270 K | 0.731 |

TABLE 2-continued

Melting, fusion enthalpy and Tg/Tm of various drugs.

| Drug | Melting (Tm) (Expt) | Enthalpy of Fusion J/gram (Expt) | Tg | Tg/Tm (K) |
|---|---|---|---|---|
| RITO (MW 720.95) | 128.68 | 101.7 | 45 to 49° C. (318.15 to 322.15 K)* | 0.791-0.801 |
| TIOCO (MW 387.7.) | 84.24 | 104.9 | −12.67° C. (260.48 K) | 0.728 |
| FUROS (MW 330.7) | ~228 | 65.32 | 44.2° C. (317.35 K) form A 54° C. (327.15 Form B) | 0.633 to 0.6527 |
| KETOC (MW 531.44) | 150.51 | 116.2 | 44.35° C.(317.5 K) | 0.749 |
| PROPFB | 95.86 | 160.61 | −7.25° C. (265.9 K) | 0.720 |
| NAPROX (MW252.2) | 155.93 | 123.6 | 62° C. (279.35 K) | 0.651 |
| FLURBI (MW 244.08) | 116.96 | 145.3 | 4.65° C.(277.8 K) | 0.712 |
| NIMO (MW 418.5) | 126.77 | 96.76 | 20° C. (293.15 K) | 0.733 |
| CHLOPR (MW276.7) | 118.27 | 42.57 | 16° C. (289.15 K) | 0.738 |
| Fenoprofen | 113.36 | | | |

Expt—Experimentally derived.
*EP1418174

The practice of the invention is illustrated by the following non-limiting examples. The invention should not be construed to be limited solely to the compositions and methods described herein, but should be construed to include other compositions and methods as well. One of skill in the art will know that other compositions and methods are available to perform the procedures described herein.

EXAMPLES

Example 1. Equilibrium Solubility Studies with IBU

Equilibrium solubility experiments were conducted to evaluate the AGF polymer as a pharmaceutical carrier and to test its potential to enhance the solubility of IBU, a model poorly soluble drug. The results are presented in FIG. 1.

The saturation solubility of neat IBU in 0.1 N HCl was found to be 0.037 mg/ml. AG polymer enhanced the solubility of IBU in 0.1 N HCl. At all polymer concentrations ranging from 0% to 3%, AGF polymer resulted in an increment in IBU solubility of 7.3 fold. Hydroxypropyl methyl cellulose K3 (HPMCK3), the control polymer, did not enhance the solubility of the IBU in 0.1N HCl with increasing HPMCK3 concentration. The increase in IBU solubility in the presence of AGF polymer was statistically significant compared to that in the presence of HPMCK3 polymer. Thus, AGF produced the maximum solubilizing effect and HPMCK3 had a very weak solubilization effect, merely as a result of their presence in the dissolution media (without any formulation treatment).

The formation of a water soluble complex between IBU and AG in addition to increased IBU wetting due to the hydrophilic nature of AGF was found to be the reason for the observed solubilizing effect of AGF. Enhancement of IBU solubility due to the mere presence of AGF dissolved in 0.1N HCl was found to be 7.3 fold.

Figure 2:
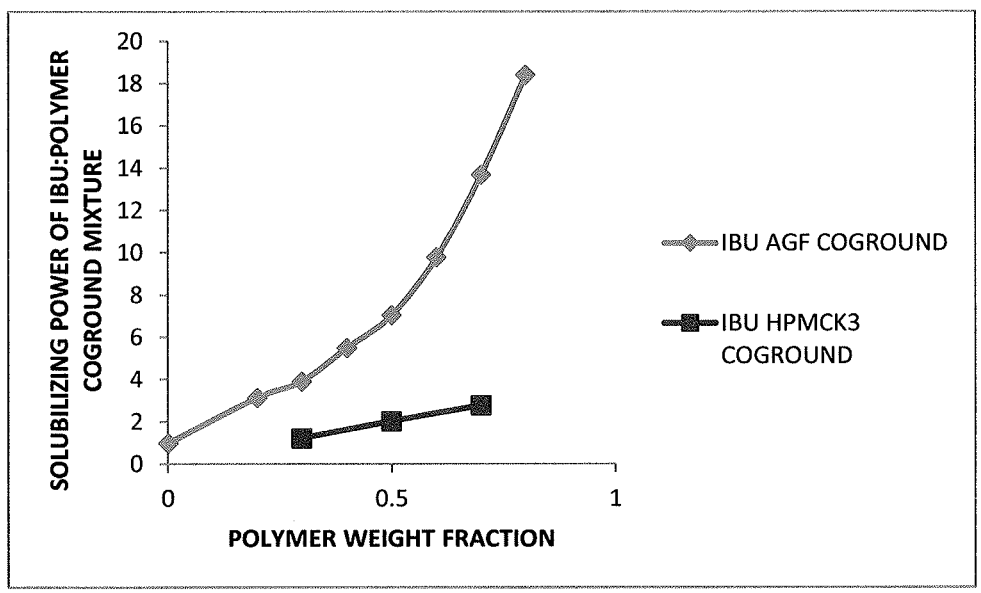
FIG. 2 shows the solubilizing power of IBU:polymer coground mixtures for the polymers AG and HPMCK3.

A similar experiment was conducted with IBU AGF coground mixture at different weight fractions. The results are shown in FIG. 2. IBU solubility increased by about 18 fold at 2:8 (IBU:AGF) coground mixture ratio. The 1:9 (IBU:AGF) coground mixture would have had a solubility increase of more than 18 fold.

Example 2. Solid Dispersion Preparation Methods

The unavailability of a common solvent for AGF polymer and IBU made the use of conventional solvent methods for preparing the solid dispersions impossible. Conventional melt/fusion methods were not a viable option considering the amorphous nature of the polymer. Various methods were attempted, as described below. Solvent methods were modified in order to use water as a solvent. In the end, the IBU AGF microsphere solid dispersion (MSD) prepared by a modified water in oil emulsion solvent evaporation technique and solid dispersions prepared with modified solvent evaporation techniques (SDM) were found to be the best methods among the various solid dispersion techniques tested.

Microsphere Solid Dispersions (MSD)

IBU AGF microspheres solid dispersion (MSD) of 10%, 20% and 30% DL were prepared by a modified water-in-oil emulsion solvent evaporation technique. Briefly, IBU was dispersed in a 28-36% aqueous solution of AGF. This drug-polymer solution was heated just near the melting point of the drug (approximately 75° C.). This led to a viscous inner phase comprising molten drug. This thick inner viscous phase was then emulsified with 200 ml of safflower oil at room temperature while stirring using an overhead electronic stirrer equipped with an impeller (Heidolph Brinkmann Model #RZR 2051 40-2000 RPM). Stirring continued for 3 hours. After evaporation of the remaining water from the inner phase, solidified microspheres were obtained. After washing the microspheres with HPLC grade acetone, they were first air dried at room temperature followed by drying in an oven at 45° C. overnight. These microspheres were stored in an airtight container until further analysis. MSD batches with drug loading ranging from 10%-75% were prepared using this method.

MSD were also prepared using the control polymer HPMCK3. 10%, 20% and 30% IBU HPMCK3 MSD were prepared, but very low encapsulation efficiency was obtained.

Solid Dispersion with Modified Solvent Evaporation Method (SDM)

The modified solvent evaporation method described by Rane et al (2007) and Karavas et al (2001) was used to prepare IBU AGF SDM. Few modifications were made to the method. Drug was dissolved in ethanol using stirring until a clear solution was obtained (below saturation solubility). Polymer was placed in a round bottom flask. Sufficient nanopure water was added to the polymer (AGF or HPMCK3) to obtain a polymer wet mass. The drug-ethanol solution was added to the polymer wet mass at once. The AGF precipitated out due to the presence of ethanol. The entire solvent was evaporated at 70° C. under vacuum using a rotavap. It took 45 minutes to 2 hours to obtain a dried mass. To ensure complete drying, the flask was kept in an oven at 45° C. overnight. The prepared SDMs were stored in an airtight container.

Solvent Deposition (SOLVDEP)

The solvent deposition method of Williams et al., 2005, *Eur J Pharm Sci* 26(3-4):288-294, was followed with a few modifications to prepare IBU AGF SOLVDEP. 400 mg of IBU was dissolved in HPLC grade acetone. Accurately weighed AGF polymer was added to it and mixed using a stir rod. The stirring continued until the entire ethanol evaporated. The samples were completely dried by placing them in the oven at 40° C. overnight.

Physical Hot Mixes (HM)

The method of Williams et al., 2005, *Eur J Pharm Sci* 26(3-4):288-294, was followed with a few modifications. Accurately weighed IBU was placed in a glass beaker. The beaker was then heated in a silicone oil bath until the IBU melted completely. Then, accurately weighed AGF polymer was mixed with this molten IBU (using geometric dilution) with a stirring rod for 20 minutes. The resulting physical hot mixes were allowed to cool down at room temperature for 24 hours.

Solvent Evaporation Using Water as a Solvent (SEWS)

The method of Al-Hamidi et al., 2010, *Colloids Surf B Biointerfaces* 76(1):170-178, modified as follows, was used to prepare IBU AGF SEWS. 0.2 gram of IBU was dissolved in 10 ml of ethanol/acetone. 0.9 mg of AGF was dissolved in an equal volume of nanopure water. The drug solution was added to the polymer solution while stirring. After evaporation of the solvents at room temperature, dried solid dispersions were obtained.

Freeze Drying (FD)

IBU AGF freeze-dried SD samples with 10% DL, 20% DL and 30% DL were prepared as follows. 10 ml of nanopure water was heated at 90° C. Accurately weighed AGF polymer was added to the water and stirred using a magnetic stir bar. Accurately weighed IBU was added to this hot AGF polymer solution and stirred for 1 minute. The thin inner phase was immediately transferred into glass culture tubes. The culture tubes were immediately placed on dry ice until the IBU AGF polymer solution solidified completely. These samples were freeze-dried for 48 hours at −45° C. using Freezer drier (Freezone-1 Liter Benchtop, Labconco, Kansas City, Mo.).

Spray Drying (SPRDY)

Spray dried 10% IBU AG SD were prepared. 8.5 gm of AGF polymer was dissolved in nanopure water while stirring. 1 g of IBU was added to the aqueous polymer solution and stirring continued. Once the drug dispersed well into the solution, 0.5 g of Carbosil® thermoplastic silicone polycarbonate urethane was added. The spray drying was performed on a BUCHI minispray dryer B-290. The inlet temperature was set to 185° C. and the outlet temperature was set to 60° C. The aspirator volume was 85%, airflow rate was 40 mm and the feed rate was 9 ml/min. The spray dried SDs were separated using a high performance cyclone separator, collected and weighed. The yield for 10% IBU AG SD was 60%. This spray-dried SD was stored in desiccators (SPRDY 60° C.). Another batch of 10% IBU AG SD was prepared using an inlet temperature of 220° C., an outlet temperature of 83° C. with a feed rate of 6 ml/min (SPRDY 90° C.).

Inner Phase Solid Dispersion (IPSD)

The inner phase obtained by following the MSD preparation protocol was poured onto the liner and air dried for 1 hour, instead of emulsifying in oil phase. Later, this IPSD was dried completely in an oven at 45° C.

Physical Mixtures (PM)

Ibuprofen-arabinogalactan physical mixtures (PMs) were used as control formulations. 10%, 20% and 30% DL physical mixtures were prepared by triturating the drug and polymer in mortar and pestle with geometric dilution. An ibuprofen-HPMCK3 physical mixture with 10% DL was also prepared using the same technique.

Basket Method

The in vitro drug dissolution rates of the dosage forms listed in Table 4 below were determined by the USP basked method (270 mesh, 53 micron pore size). The Van Kel VK7010 dissolution system was employed. 900 ml of 0.1 N HCl at 37° C. was used as a dissolution medium. The media was selected to mimic gastric pH and to allow greater discrimination of ibuprofen dissolution profiles due to formulation and processing effects. The dissolution experiment was run at 100 rpm. Each sample contained a dosage form equivalent to 25 mg of ibuprofen to maintain the non sink conditions, i.e. to employ a volume of medium (900 ml in this case) that is less than the volume of medium required for sink conditions, which is three times that required in order to form a saturated solution of drug. In vitro dissolution of 25 mg of neat ibuprofen was used as a control. At appropriate time intervals, samples were collected and replaced by fresh media. Each sample was filtered and the drug was analyzed using Agilent/HP 8453 UV-Vis spectrophotometer ($\lambda$mx=222 nm). The experiment was conducted in triplicate. T50 (time for 50% drug release), T60 (time for 60% drug release), and T80 (time for 80% drug release) was recorded directly from the dissolution profiles.

Results

The results are summarized in Tables 3 and 4 below. It was found that the fastest dissolution rate of IBU correlated to amorphous IBU formation in solid dispersions and to the porous matrix structure of the solid dispersion. Formation of solid dispersions did not automatically result in enhancing IBU dissolution even in the presence of amorphous IBU due to loosely held amorphous IBU and AGF polymer. On the other hand, the structure of IPSDs and FRZD, which was not a porous matrix structure, did not enhance IBU dissolution either. The character of the MSDs and SDMs that was responsible for the decrease in ibuprofen crystallinity and the increase in ibuprofen dissolution was that both these solid dispersions comprise an arabinogalactan polymer matrix and ibuprofen uniformly dispersed in the matrix.

It was also evident that the amorphous IBU needs to be protected against precipitation once it is in the dissolution media.

TABLE 3

Characteristics of IBU AGF solid dispersions prepared by different techniques.

| Formulation | IBU DL | IBU form | IBU Melting | Hydrogen bonding |
|---|---|---|---|---|
| SOLV DEPO | 10% | Crystalline | 74.92 | Yes |
| HM | 10% | Crystalline | 74.50 | Yes |
| | 20% | Crystalline | — | — |
| | 30% | Crystalline | 74.31 | Yes |
| SEWS | 10% (ETHANOL) | Crystalline | 77.92 | No |
| | 10% (ACETONE) | Crystalline | 77.27 | No |
| FRZD | 10% | Amorphous | 0 | Yes |
| | 20% | Partially Crystalline | 71.17 | Yes |
| | 30% | Crystalline | 73.47 | Yes |
| | 10% HPMCK3 | Amorphous | 0 | — |
| SPRDY | 10% (60° C.) | Almost amorphous | 75.68 | Yes |
| | 10% (90° C.) | Amorphous | 0 | Yes |
| IPSD | 10% | Amorphous | 0 | No |
| | 20% | Partially Crystalline | 71.48 | No |
| | 30% | Crystalline | 72.24 | Yes |
| MSD | 10% | Amorphous | 0 | Yes |
| | 20% | Amorphous | 72.58 | Yes |
| | 30% | Almost amorphous | 72.93 | Yes |
| SDM | 10% | Amorphous | 0 | Yes |
| | 20% | Almost amorphous | 72.80 | Yes |
| | 30% | Partially crystalline | 74.02 | Yes |
| | 10% HPMCK3 | Amorphous | 0 | Yes |
| | 30% HPMCK3 | Partially Crystalline | 76.32 | Yes |
| PM | 10% | Crystalline | 73.48 | No |
| | 20% | Crystalline | 74.04 | No |
| | 30% | Crystalline | 74.57 | No |
| | 10% HPMCK3 | Crystalline | 74.14 | No |
| | 30% HPMCK3 | Crystalline | 75.42 | No |

TABLE 4

Dissolution at T50 (time for 50% drug release), T60 (time for 60% drug release), T80 (time for 80% drug release) of IBU AGF solid dispersions made by different techniques.

| Formulation | T50 | T60 | T80 |
|---|---|---|---|
| Neat IBU | 190 min | 300 min | Greater than 400 min |
| 10% IBU AGF SOLDEP | 92 min | 140 min | Greater than 300 min |
| 10% IBU AGF HM | 105 min | 150 min | 290 min |
| 10% IBU AGF FRZD | 38 min | 48 min | 90 min |
| 10% IBU AGF SPRYDRY | Max 8% at 5 min | — | — |
| 10% IBU AGF IPSD | 17 min | 30 min | 100 min |
| 10% IBU AGF MSD | 5 min | 6 min | 10 min |
| 10% IBU AGF SDM | 4 min | 5 min | 9 min |

Example 3. Encapsulation Efficiency of Ibuprofen-Loaded Arabinogalactan Microsphere Solid Dispersions Preparation of Ibuprofen-Loaded Arabinogalactan Microsphere Solid Dispersions Ibuprofen-loaded arabinogalactan microsphere solid dispersions (MSDs) of 10%, 20% and 30% drug load (DL) were prepared by a modified water in oil emulsion solvent evaporation technique as described above.

Scanning Electron Microscopy

The scanning electron microscope (SEM) photomicrographs were obtained using a FEI Quanta 600 FEG Mark II ESEM (Environmental Scanning Electron Microscope) located at University of Pennsylvania (Philadelphia, Pa.). The samples were coated with a thin gold-palladium layer by sputter coater unit Cressington Sputter Coater 108. SEM of SDM samples were obtained using Hitachi S-3500N SEM located at Penn State (Environmental Scanning Electron Microscope) (University Park, PA). The samples were mounted on aluminum samples holder with carbon tape and sputtered with thin film of gold. A few samples were gold coated and images were obtained by FEI Quanta 200 ESEM at Penn State (Environmental Scanning Electron Microscope) (University Park, PA).

Figure 3:
FIG. 3 shows scanning electron microscope (SEM) photomicrographs of neat ibuprofen (left panel) and pure arabinogalactan fibergrade (right panel).
Figure 4:
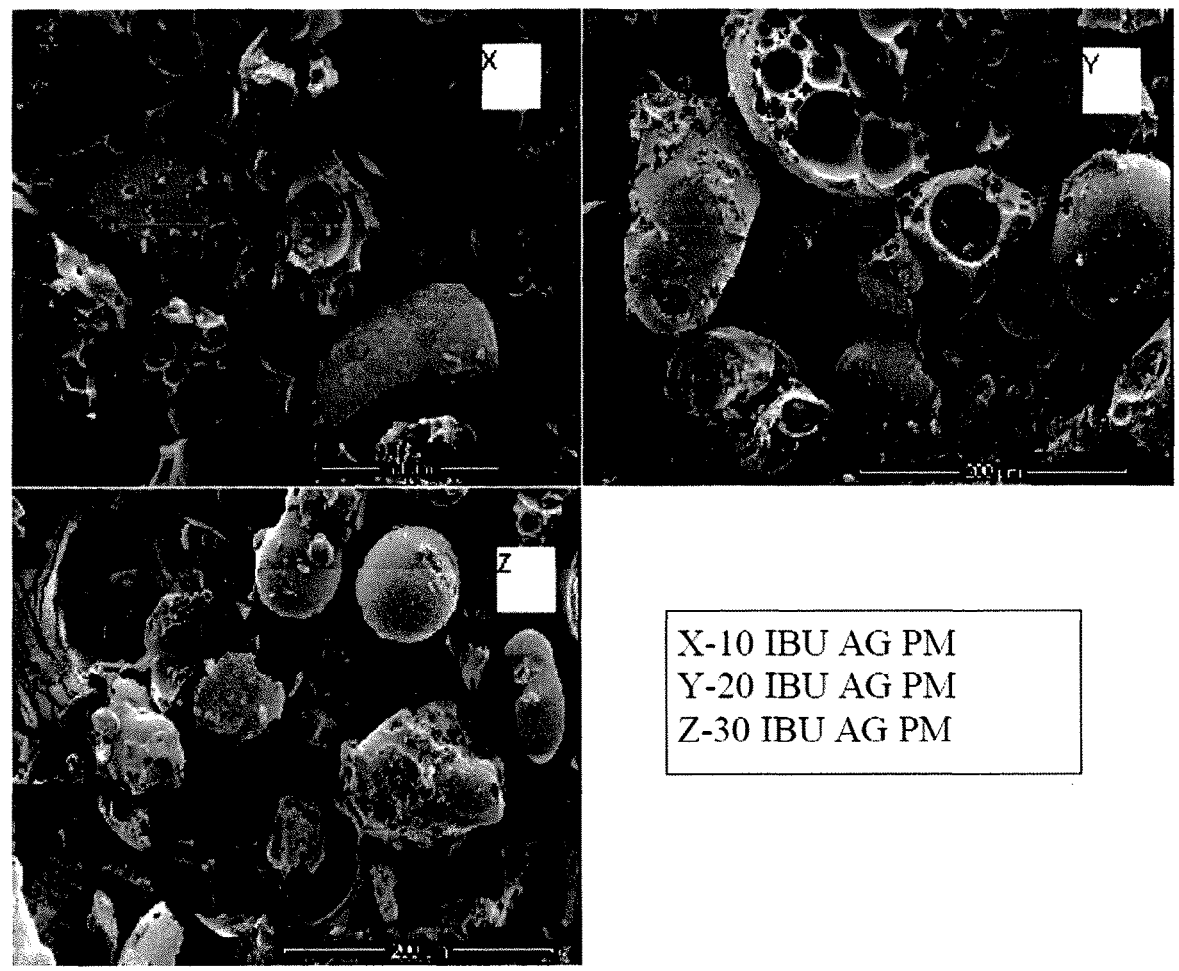
FIG. 4 shows SEM photomicrographs of ibuprofen-arabinogalactan physical mixtures (PMs). X: 10% drug load; Y: 20% DL; Z: 30% drug load.
Figure 5A:
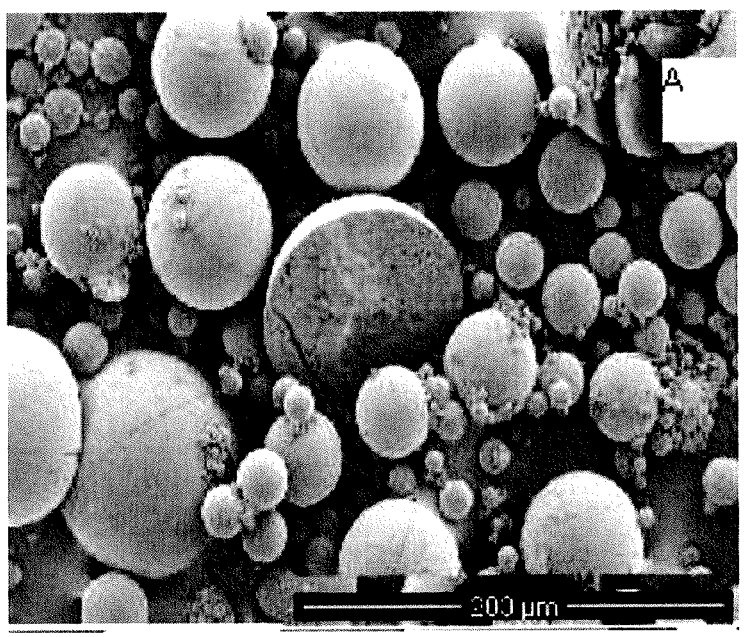
FIGS. 5A and 5B show SEM photomicrographs of ibuprofen-arabinogalactan microsphere solid dispersions (MSDs) at 10% drug load.
Figure 5B:
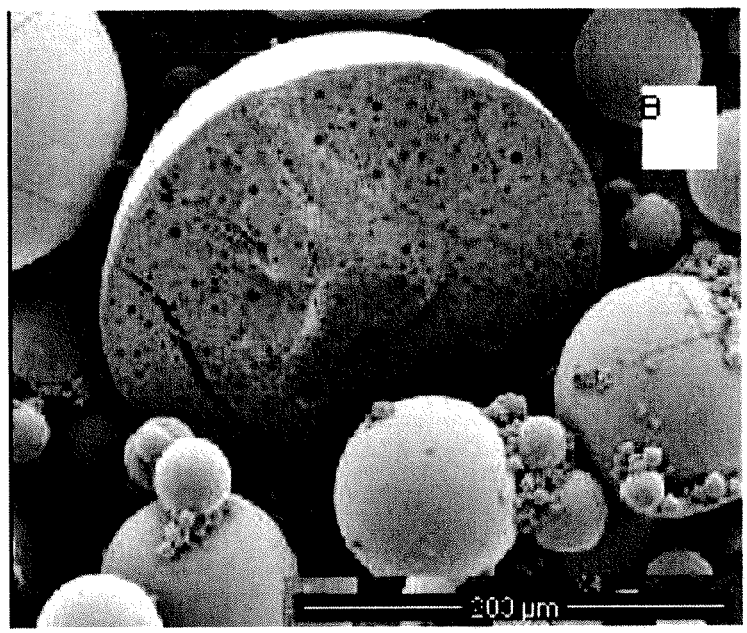
Figure 6A:
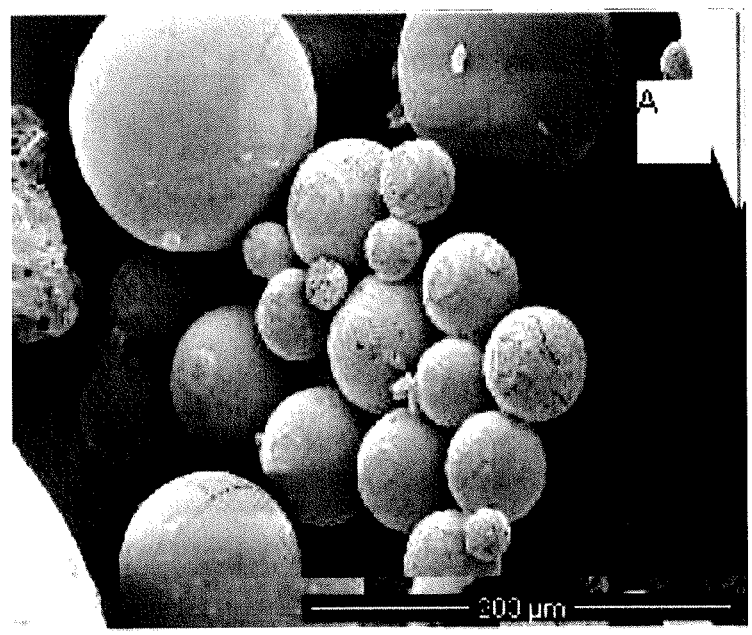
FIGS. 6A and 6B show SEM photomicrographs of ibuprofen-arabinogalactan MSDs at 20% drug load.
Figure 6B:
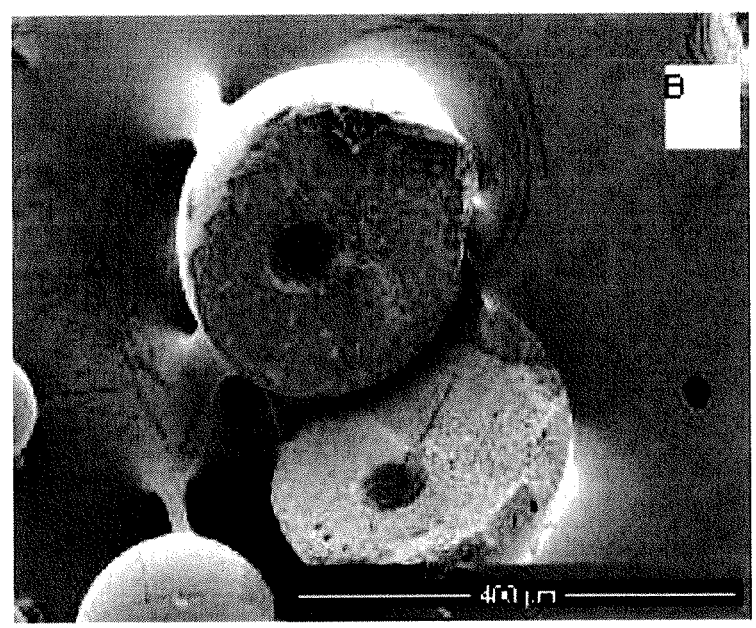
Figure 7A:
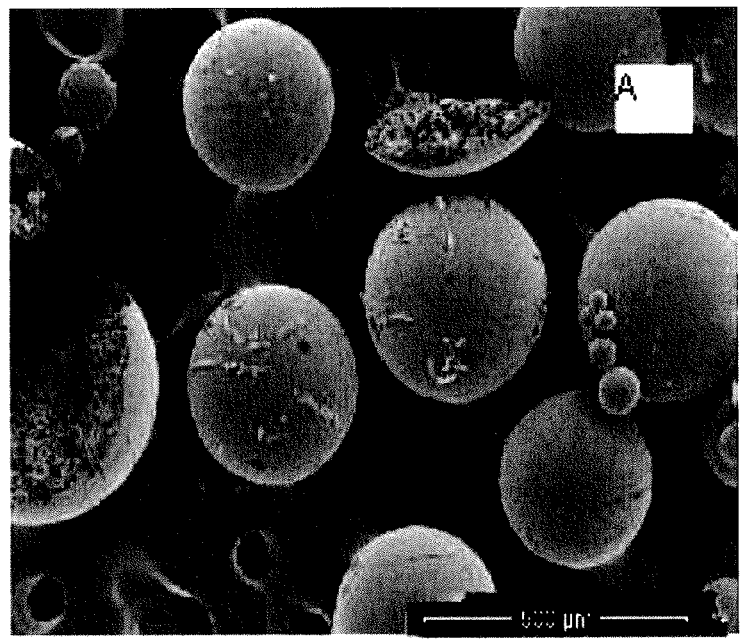
FIGS. 7A and 7B show SEM photomicrographs of ibuprofen-arabinogalactan MSDs at 30% drug load.
Figure 7B:
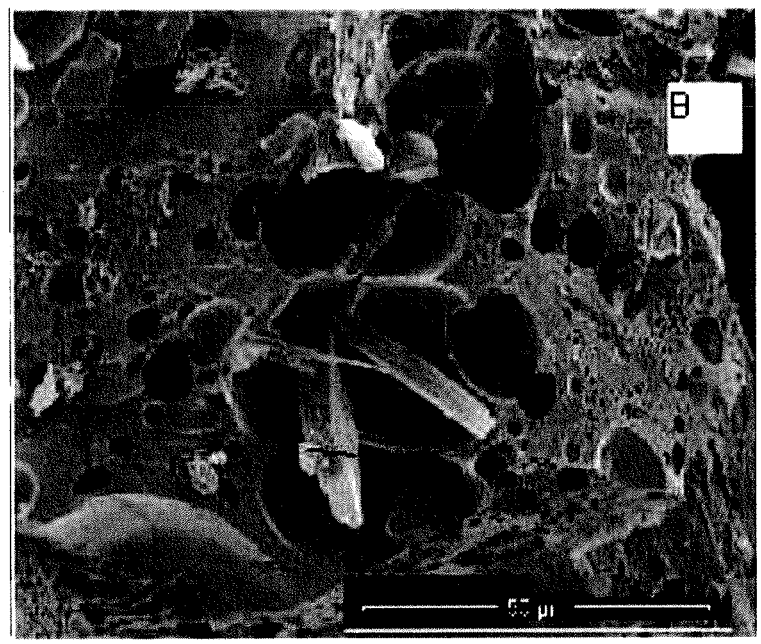

Free flowing, spherical ibuprofen-arabinogalactan microspheres were obtained as shown in the SEM micrograph in FIG. 3.

Ibuprofen Content Assay

The analysis of ibuprofen content in each batch (respective to the % drug loading) was carried out by dissolving crushed MSDs or physical mixtures (PMs) equivalent to 25 mg of ibuprofen in 250 ml of pH 7.2 phosphate buffer. This solution was stirred for 2 hours. The amount of drug was then determined by UV spectrophotometry at 222 nm (Agilent/HP 8453 UV-Vis spectrophotometer).

Estimation of Encapsulation Efficiency and Percent Yield

Percent encapsulation efficiency and % yield of ibuprofen-arabinogalactan MSDs were calculated as below % Encapsulation efficiency=(Actual drug loading/Theoretical drug loading)*100%

Yield=(Practical yield/Theoretical yield)*100

The results are shown in Table 5 below.

TABLE 5

% Encapsulation efficiency and % yield of ibuprofen-arabinogalactan microsphere solid dispersions (MSD).

| Ibuprofen-arabinogalactan MSD drug load (DL) | % Encapsulation efficiency | % Yield |
|---|---|---|
| 10% ibuprofen | 85.46 ± 5.56 | 67.00 ± 4.82 |
| 20% ibuprofen | 85.87 ± 3.04 | 58.83 ± 11.47 |
| 30% ibuprofen | 80.92 ± 7.33 | 62.00 ± 4.26 |

Additional ibuprofen-arabinogalactan MSDs with drug loads of 40%, 50% and 75% were prepared. Their respective encapsulation efficiencies were 53.18%, 48.29% and 30.97%.

Preparation of Ibuprofen Loaded HPMCK3 Microsphere Solid Dispersions

Free-flowing MSDs were also obtained with ibuprofen-HPMCK3. 10%, 20% and 30% ibuprofen DL HPMCK3 MSDs were prepared using the same emulsification solvent evaporation described above. A polymer concentration of 14%-18% was used because of the highly viscous and colloidal nature of the HPMCK3 polymer.

Ibuprofen-HPMCK3 MSDs with drug loads of 10% and 30% were prepared successfully but with very low respective encapsulation efficiencies of 2.48% and 4.32%. Repetitive batches prepared with 10% ibuprofen drug loading with HPMCK3 as the carrier did not result in an encapsulation efficiency higher than 7%. Thus, the carrier HPMCK3 did not result in the efficient incorporation of ibuprofen into the MSDs prepared by water in oil emulsion solvent evaporation method. HPMCK3 is insoluble in water. Therefore, it disperses out and does not form a thick viscous inner phase like that formed by arabinogalactan. Thus, the drug partitions into the outer oily phase resulting in a very low encapsulation efficiency.

Preparation of Ibuprofen-Araginogalactan Physical Mixtures

Ibuprofen-arabinogalactan/HPMCK3 physical mixtures (PMs) were prepared as described above.

The encapsulation efficiencies of PMs of 10%, 20% and 30% DL ibuprofen control formulations for both the carriers arabinogalactan and HPMCK3 were well above 80%.

Example 4. Characterization of Ibuprofen-Arabinogalactan MSDs and SDMs

Scanning Electron Microscopy (SEM)

To reveal the morphology of the ibuprofen-arabinogalactan MSDs, scanning electron micrographs of pure drug, ibuprofen-arabinogalactan MSD and ibuprofen-arabinogalactan physical mixtures were obtained using a FEI Quanta 600 FEG Mark II ESEM (Environmental Scanning Electron Microscope). The samples were coated with a thin gold-palladium layer by sputter coater unit Cressington Sputter Coater 108.

SEM photomicrographs of neat ibuprofen, pure arabinogalactan, physical mixtures and MSDs are shown in FIGS. 3-7. From these photomicrographs, it is clear that MSD resulted in spherical, free-flowing particles irrespective of drug loading. In 30% DL MSD, crystalline ibuprofen was present on the surface as well as inside the MSD as is evident from the cross-section of the MSD. However, for 20% DL MSD, micronized ibuprofen is present but in small amounts. In 10% DL MSD, absence of ibuprofen crystals suggests completely amorphized ibuprofen.

PMs irrespective of DL show presence of crystalline ibuprofen in micronized form. The SEM of a cross section of the MSD also shows the porous nature of the MSD, which results from the rapid evaporation of the solvent.

Differential Scanning Calorimetry

Differential Scanning calorimetry (DSC) was performed using a DSC Q 200 system operating with software TAQ Series Advantage Q Series Q200-1531 (DSC Q 200 @mfg.dsc). Approximately 4-5 mg of weighed sample were placed in a standard aluminum pan and sealed with a lid. A heating rate of 5° C./min was applied from 20° C. to 200° C.

Figure 8A:
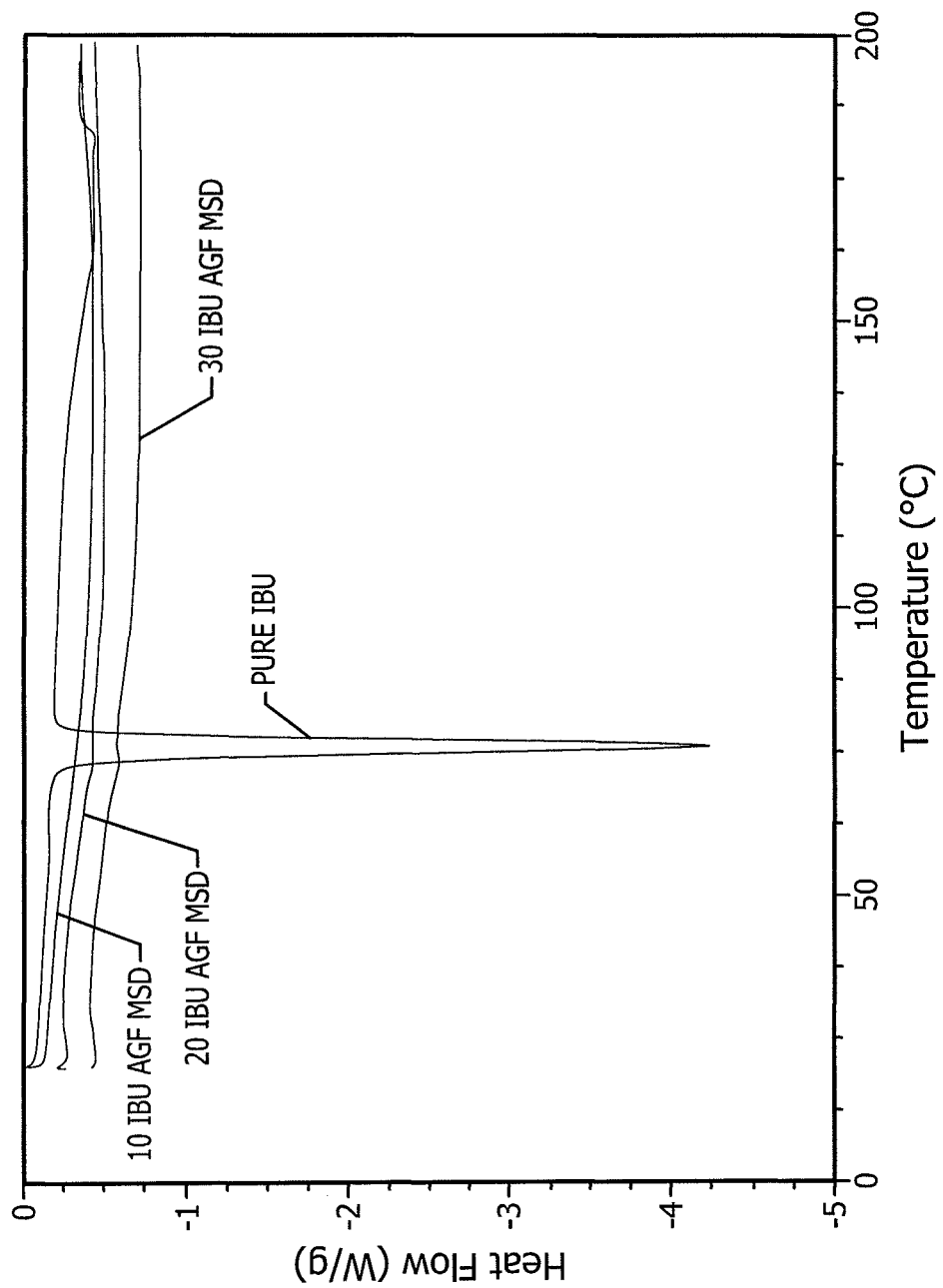
FIG. 8A shows differential scanning calorimetry (DSC) thermographs of ibuprofen-arabinogalactan MSDs at 10%, 20% and 30% drug loading. The plots shown from top to bottom as read at the 50° C. mark are: NEAT IBU, 10% IBU AGF MSD, 20% IBU AGF MSD, 30% IBU AGF MSD.

The DSC thermograms of neat ibuprofen and ibuprofen-arabinogalactan MSDs are shown in FIG. 8A. An apparent endothermic peak is shown at 76.56° C. representing melting of crystalline ibuprofen. This sharp ibuprofen peak was absent in 10% DL ibuprofen-arabinogalactan MSD and in 20% DL ibuprofen-arabinogalactan MSD, suggesting amorphization of ibuprofen in these MSDs. The 30% DL ibuprofen-arabinogalactan MSD endotherm in the figure showed a peak with a small intensity for the melting of ibuprofen. This indicated that a small amount of ibuprofen was present in crystalline form at this drug load.

Figure 8B:
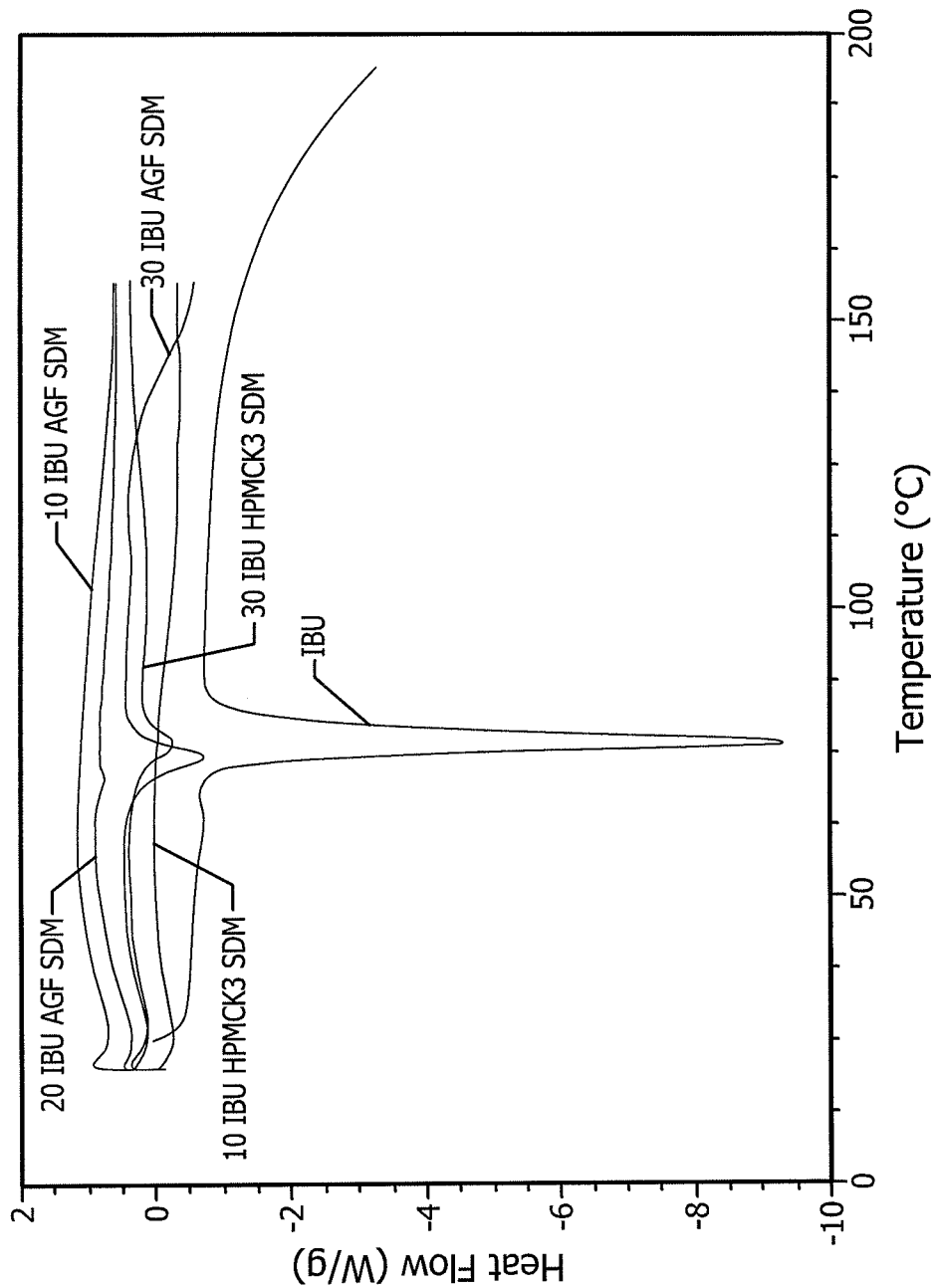
FIG. 8B shows DSC thermographs of ibuprofen-arabinogalactan SDM and ibuprofen-HPMCK3 SDM formulations at different drug loadings. The plots shown from top to bottom as read at the 50° C. mark are: 10% IBU AGF SDM, 20% IBU AGF SDM, 30% IBU AGF SDM, 30% IBU HPMCK3 SDM, 10% IBU HPMCK3 SDM and NEAT IBU.

Ibuprofen was completely amorphous in 10% SDM formulation, whereas a very minute intensity at 20% SDM formulations indicated almost complete amorphization of IBU in this formulation (FIG. 8B). The 30% SDM formulations, on the other hand, retained some of the IBU in crystalline form.

Figure 8C:
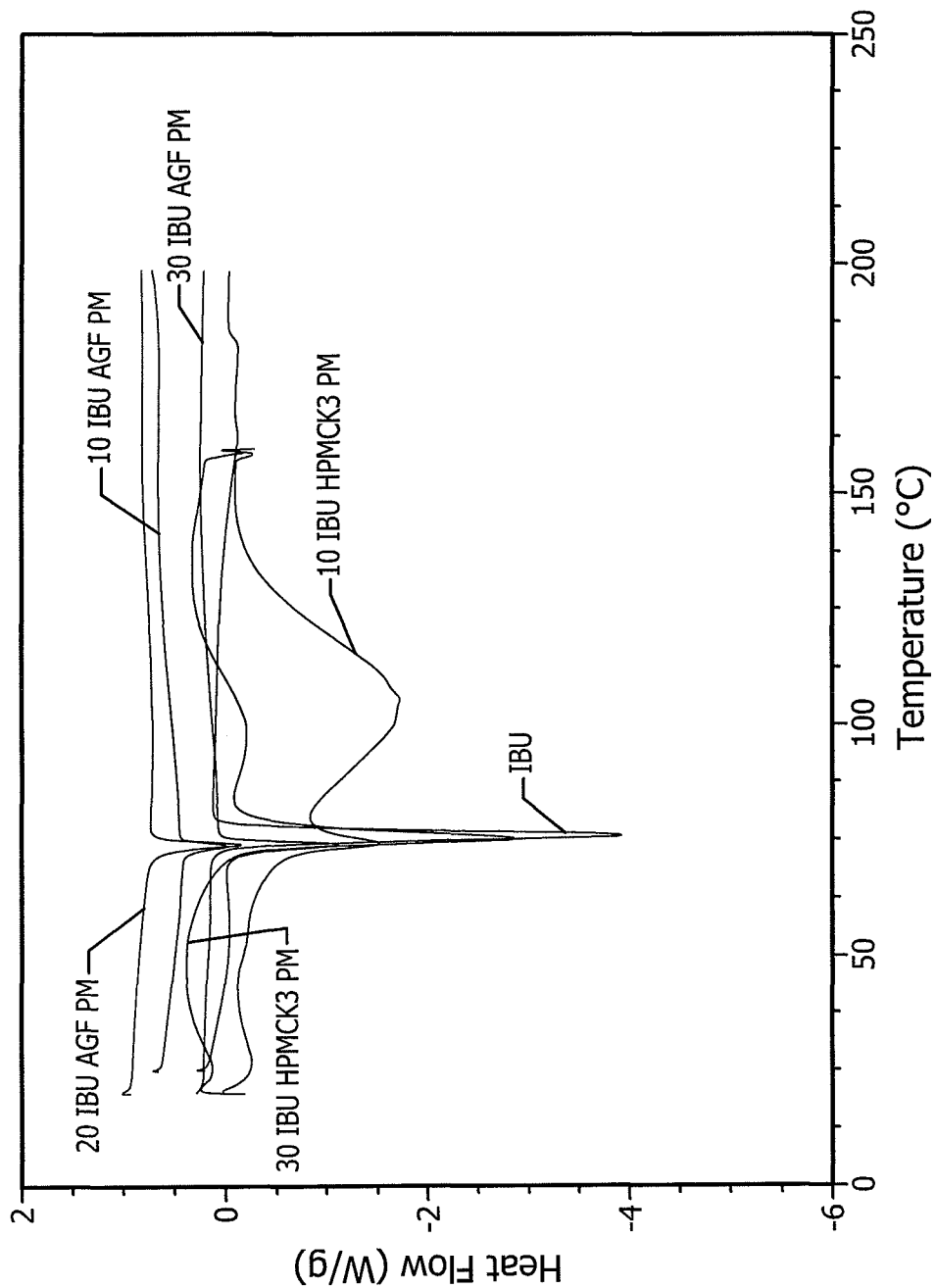
FIG. 8C shows DSC thermographs of ibuprofen-arabinogalactan PM and ibuprofen-HPMCK3 PM formulations at different drug loadings. The plots shown from top to bottom as read at the 50° C. mark are: 20% IBU AGF PM, 10% IBU AGF PM, 30% IBU HPMCK3 PM, NEAT IBU, 30% IBU AGF PM, 10% IBU HPMCK3 PM.

Physical mixtures of ibuprofen and arabinogalactan, or ibuprofen and HPMCK3 at various drug loads gave an endothermic peak at approximately 76° C. with intensity increasing with drug load (FIG. 8C). These results indicate that the PM of ibuprofen with arabinogalactan or HPMCK3 retained the ibuprofen in its crystalline form only.

Thus the decline in ibuprofen crystallinity in MSDs and SDMs made with arabinogalactan is due to the character of the MSDs and SDMs, and not merely due to the amorphous nature of the polymer. The character of the MSDs and SDMs that was responsible for the decrease in ibuprofen crystallinity was that both these solid dispersions comprise an arabinogalactan polymer matrix and ibuprofen uniformly dispersed in the matrix.

Powder X-Ray Diffraction

Powder X-ray diffraction of the ibuprofen-arabinogalactan MSDs was carried out to determine the crystallinity of the ibuprofen. Powder samples (150 µg-250 µg) were placed on a sample holder and the diffractograms were collected using a Bruker D8 diffractometer (Madison, Wis.) with Cu Kα radiation. The voltage of 40 kV was used and the current was 40 mA. The samples were scanned from 2 θ to 40 θ at a rate of 2 θ/minute. The data analysis was done using Bruker-AXs EVA software (version 15.0).

Figure 9A:
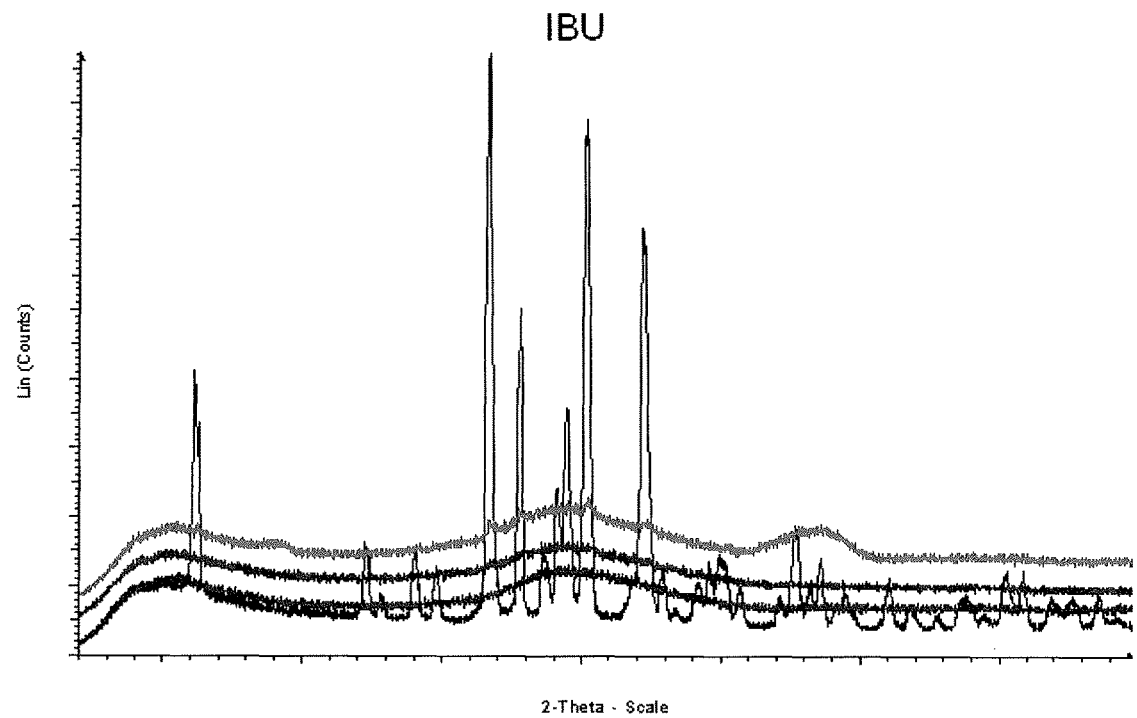
FIG. 9A shows X-ray powder diffractograms (XRPD) of IBU AG MSD formulations of 10%, 20% and 30% drug loading at 2 θ/min from 2 θ to 40 θ. From bottom to top at the 10 Two-Theta mark are shown: NEAT IBU, 10% IBU AG MSD, 20% IBU AG MSD and 30% IBU AG MSD.
Figure 9B:
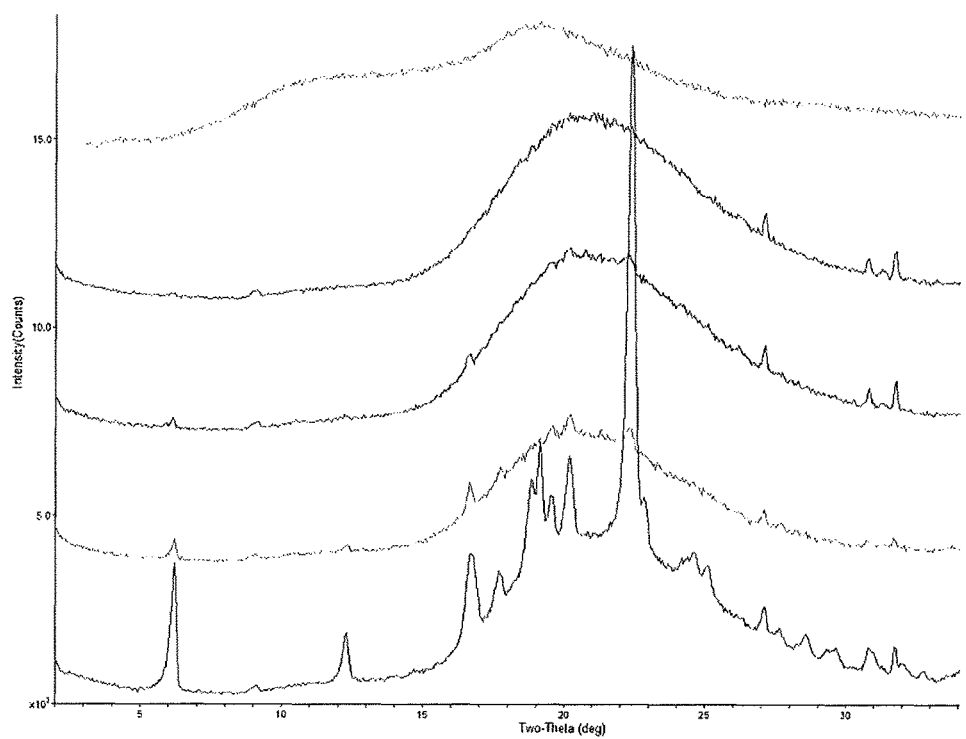
FIG. 9B shows XRPD diffractograms of IBU AG SDM formulations at 2 θ/min from 2 θ to 40 θ. From bottom to top at the 10 Two-Theta mark are shown: NEAT IBU, 30% IBU AG SDM, 20% IBU AG SDM, 10% IBU AG SDM and NEAT AG.
Figure 9C:
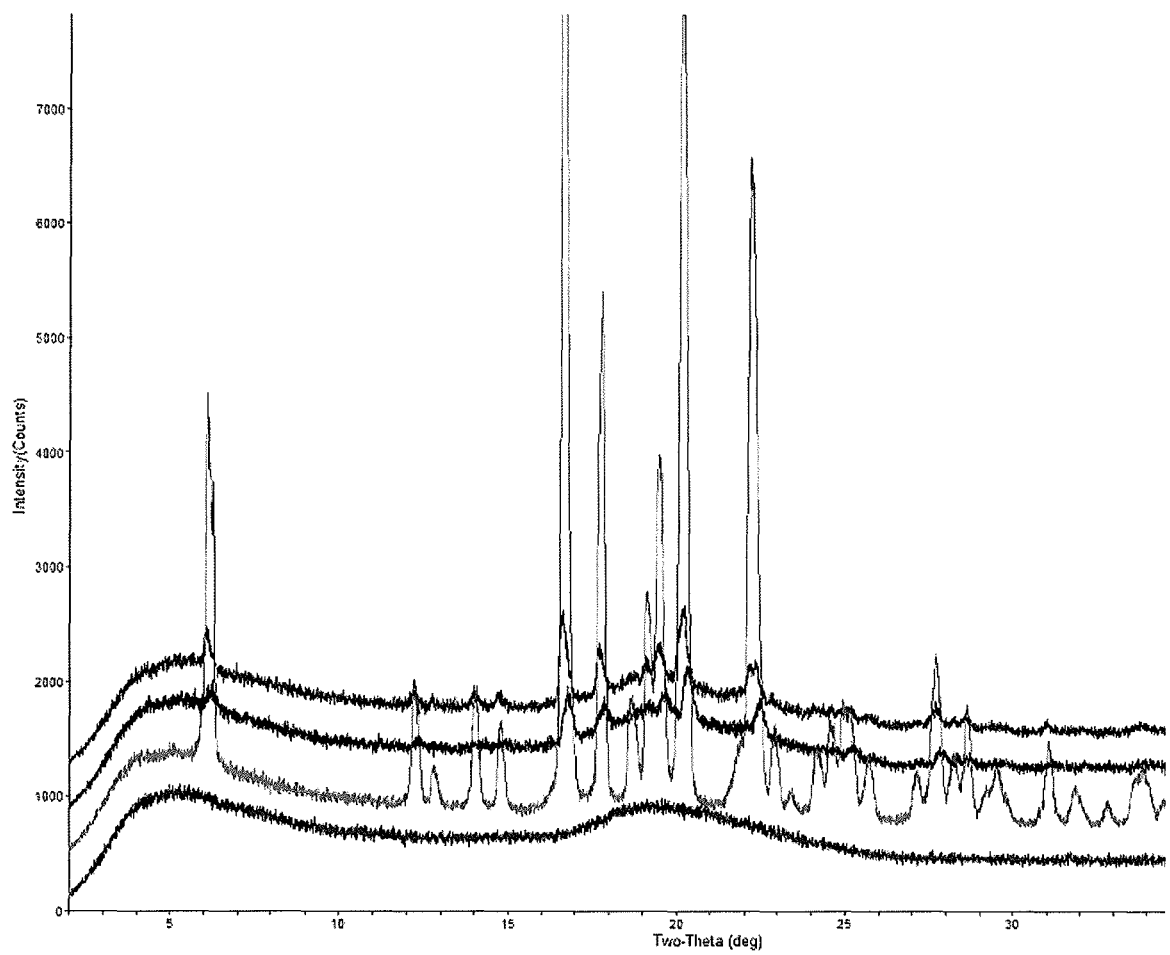
FIG. 9C shows XRPD diffractograms of IBU AG PMs at 2 θ/min from 2 θ to 40 θ. From bottom to top at the 10 Two-Theta mark are shown: NEAT AG, NEAT IBU, 10% IBU AG PM and 20% IBU AG PM.
Figure 10:
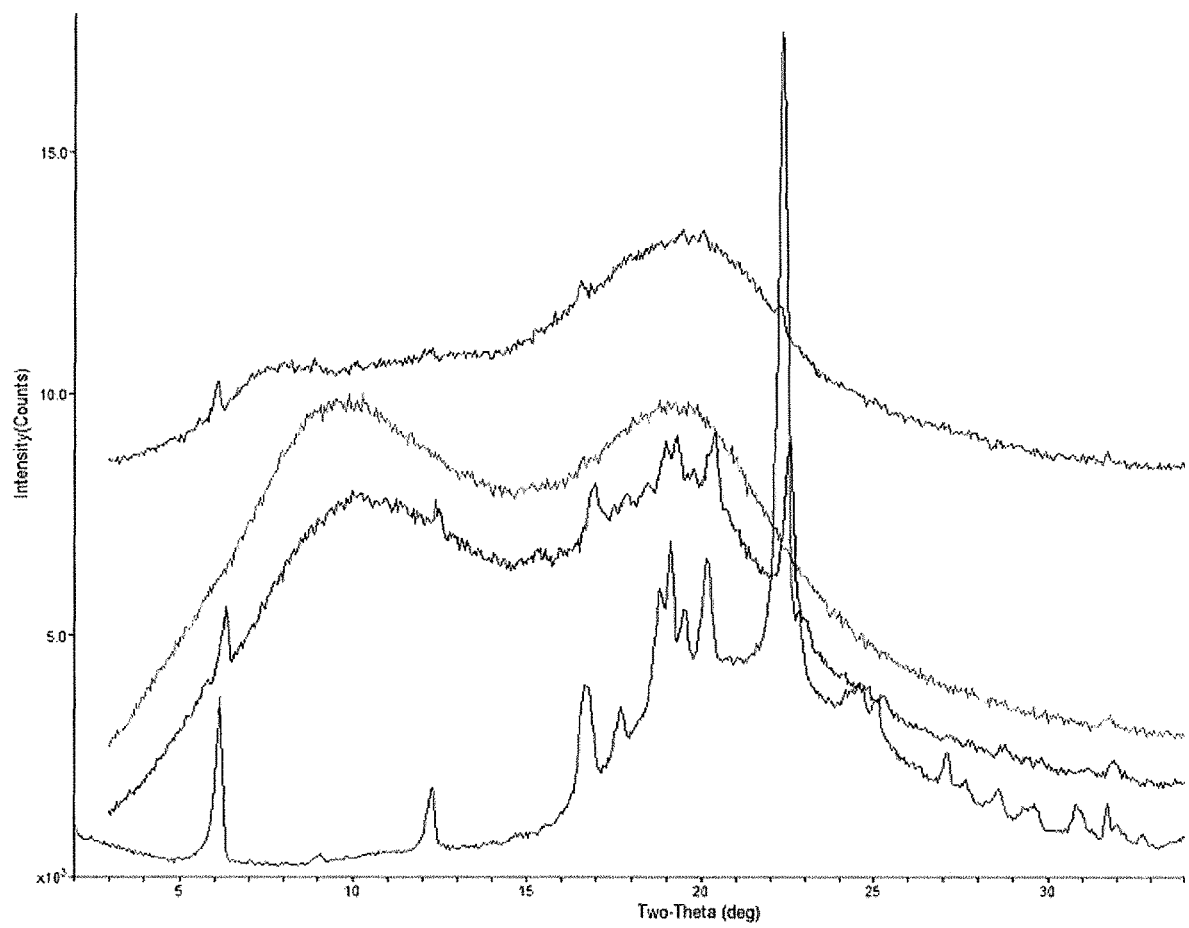
FIG. 10 shows XRPD diffractograms of IBU HPMCK3 formulations at 2 θ/min from 2 θ to 40 θ. From bottom to top at the 10 Two-Theta mark are shown: NEAT IBU, 10% HPMCK3 PM, NEAT HPMCK3 and 10% IBU HPMCK3 SDM.

X-ray diffractograms of IBU AGF MSD, IBU AGF SDM and IBU AGF PM are shown in FIGS. 9A-C. The X-ray diffraction pattern of neat ibuprofen revealed high intensity peaks at 6.1°, 12.2°, 16.7°, 17.8°, 19°, 22.3° (2 θ). These diffraction peaks attributed to ibuprofen crystallinity are present in all IBU AGF PMs, which confirmed the presence of crystalline ibuprofen in these formulations. Formulations 10% IBU AGF MSD, 10% IBU AGF SDM were XRPD amorphous. IBU crystallinity peaks were present with much attenuated intensity suggesting almost complete amorphization of IBU in 20% IBU AGF MSD and 20% IBU AGF SDM. Partial amorphization of IBU took place in 30% IBU AGF MSD and 30% IBU AGF SDM as may be seen from the diffractograms. 10% IBU HPMCK3 SDM formulation was found to be XRPD amorphous as well as shown in FIG. 10

Fourier Transform Infrared (FT-IR) Spectroscopy

FT-IR spectroscopy was carried out on IBU AGF SDM, IBU AGF MSD and IBU AGF PM formulations in order to study the molecular interaction between the drug and the carrier. The infrared spectra were analyzed with a Nicolet Magna-IR™ system 500 (Nicolet Instrument, Madison, Wis.). Approximately 2-3 mg of powdered samples were placed on the crystal. The swing arm was placed above the sample and the pressure knob was turned clockwise until the force gauge displayed a pressure of 60. Scans were obtained at a resolution of 2 $cm^{-1}$, from 4000 to 650 $cm^{-1}$ at 64 scans per second. The scanning spectrum was analyzed using Omni™ software (West Covina, Calif.).

Figure 11:
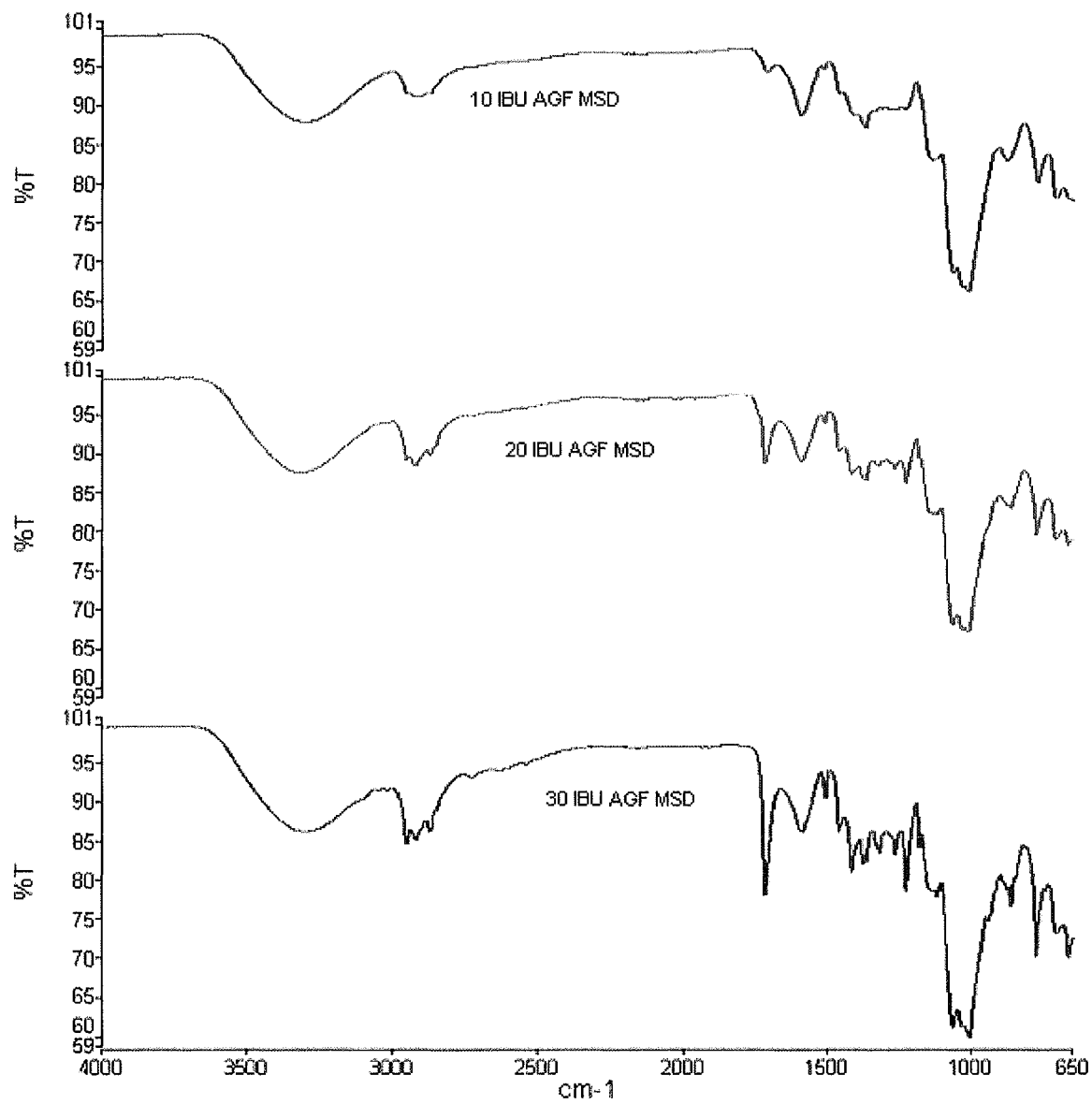
FIG. 11A shows the Fourier transform infrared (FTIR) spectra of IBU AGF MSD formulations.
FIG. 11B shows FTIR spectra of IBU AGF SDM formulations.
FIG. 11C shows FTIR spectra of IBU AGF PM formulations.
FIG. 11D shows FTIR spectra of NEAT IBU and NEAT AGF polymer.
FIG. 11E shows the FTIR spectra of IBU HPMCK3 SDM and IBU HPMCK3 PMs.
Figure 11:
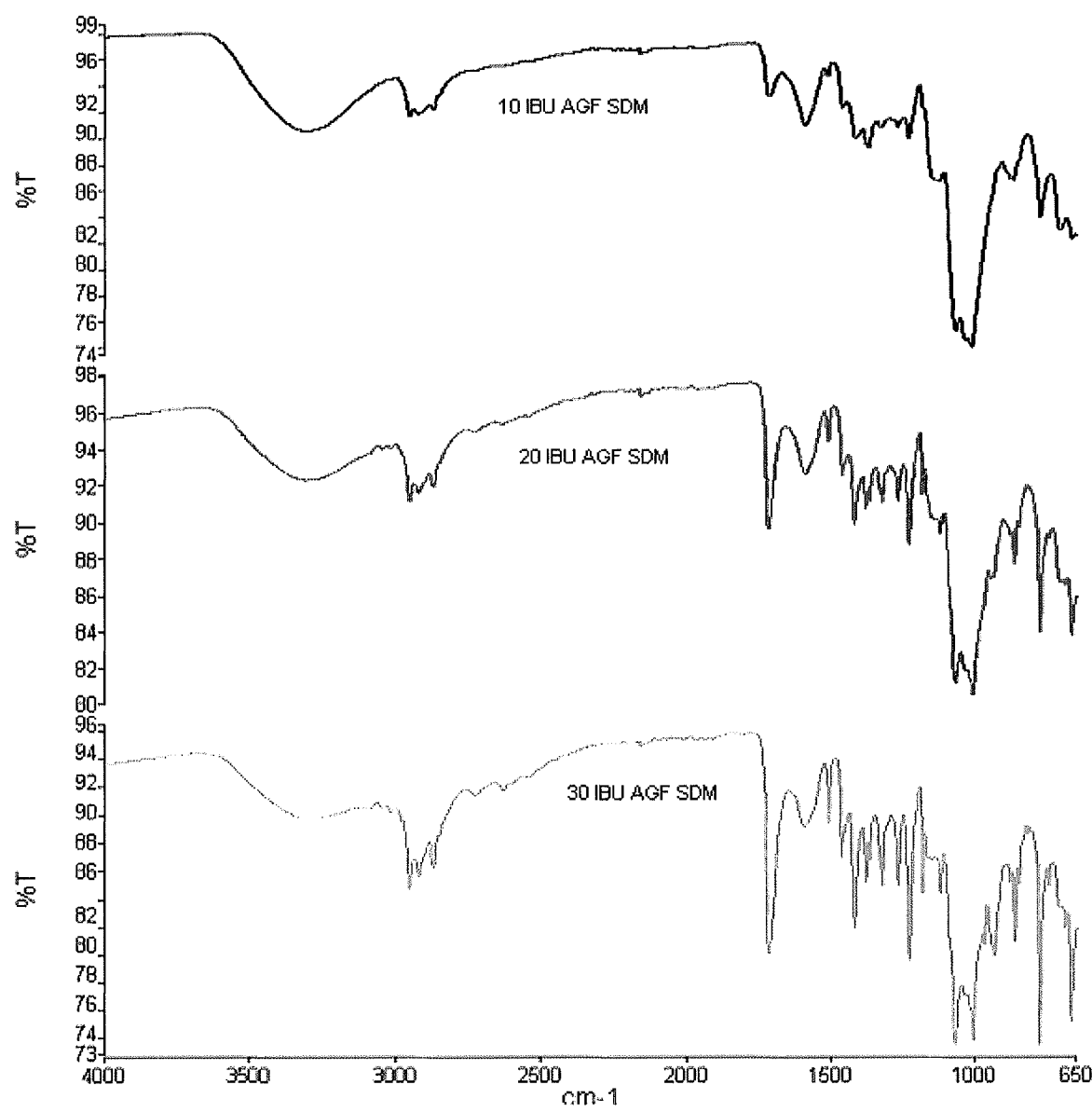
Figure 11C:
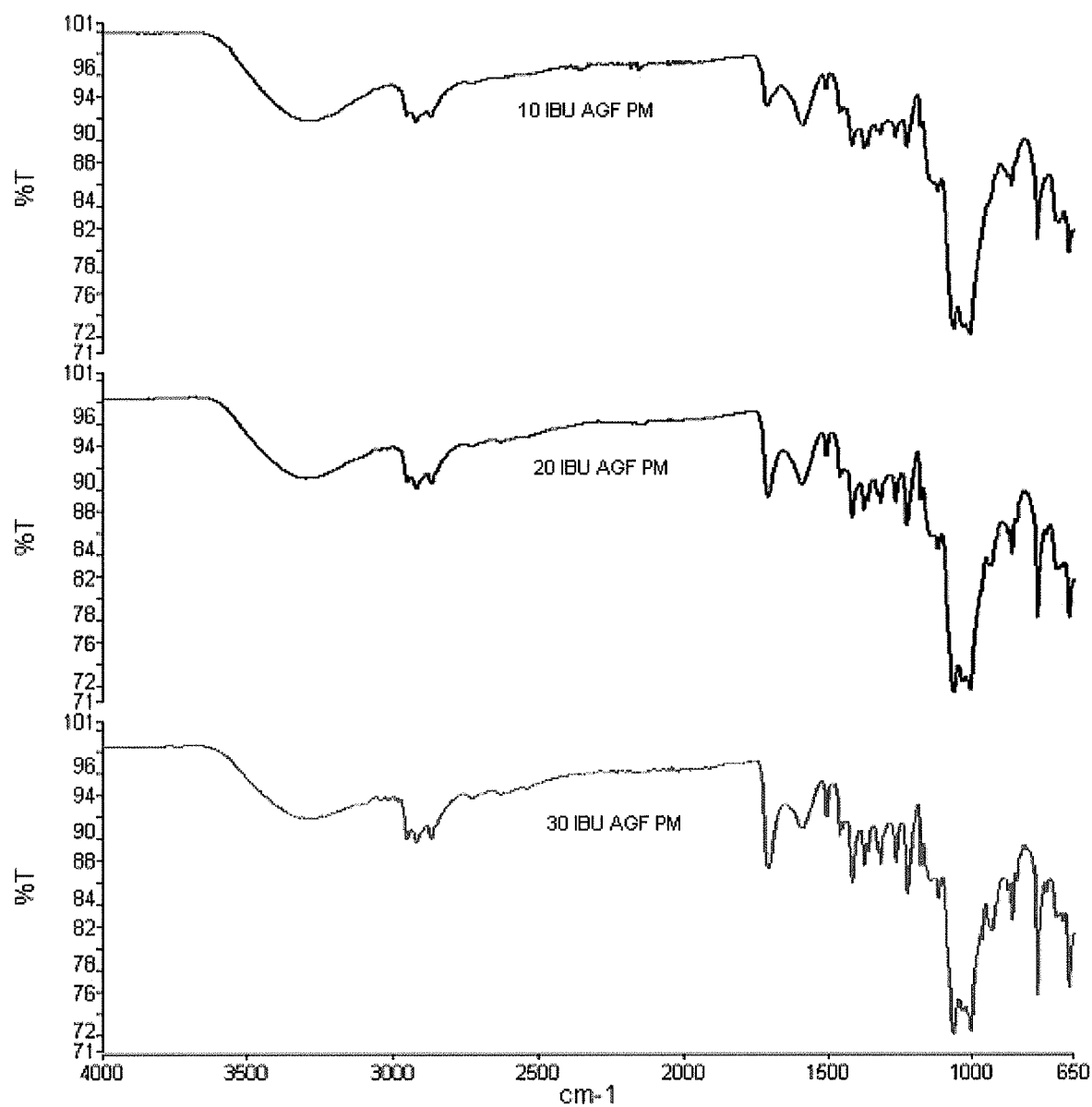
Figure 11D:
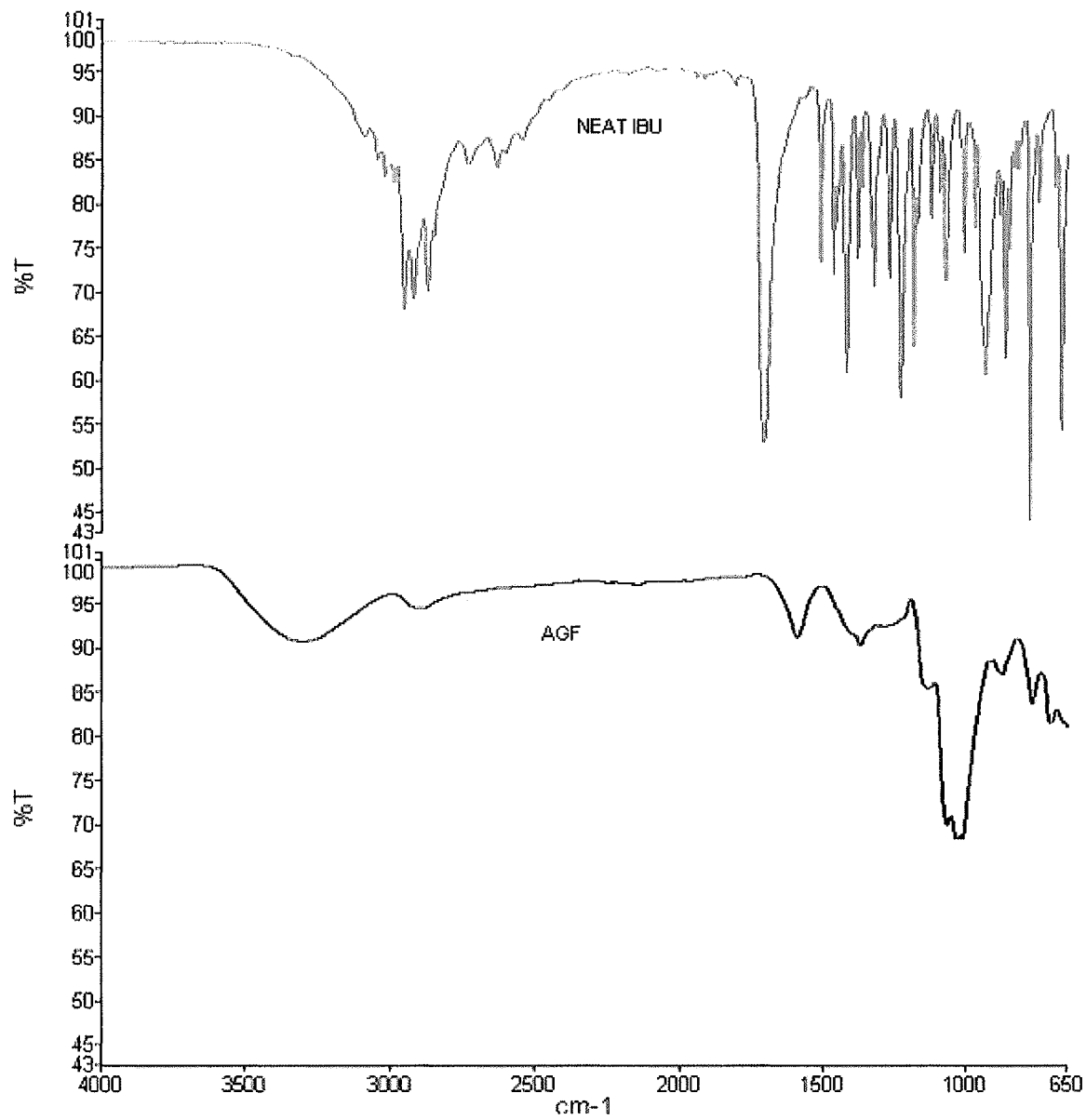
Figure 11E:
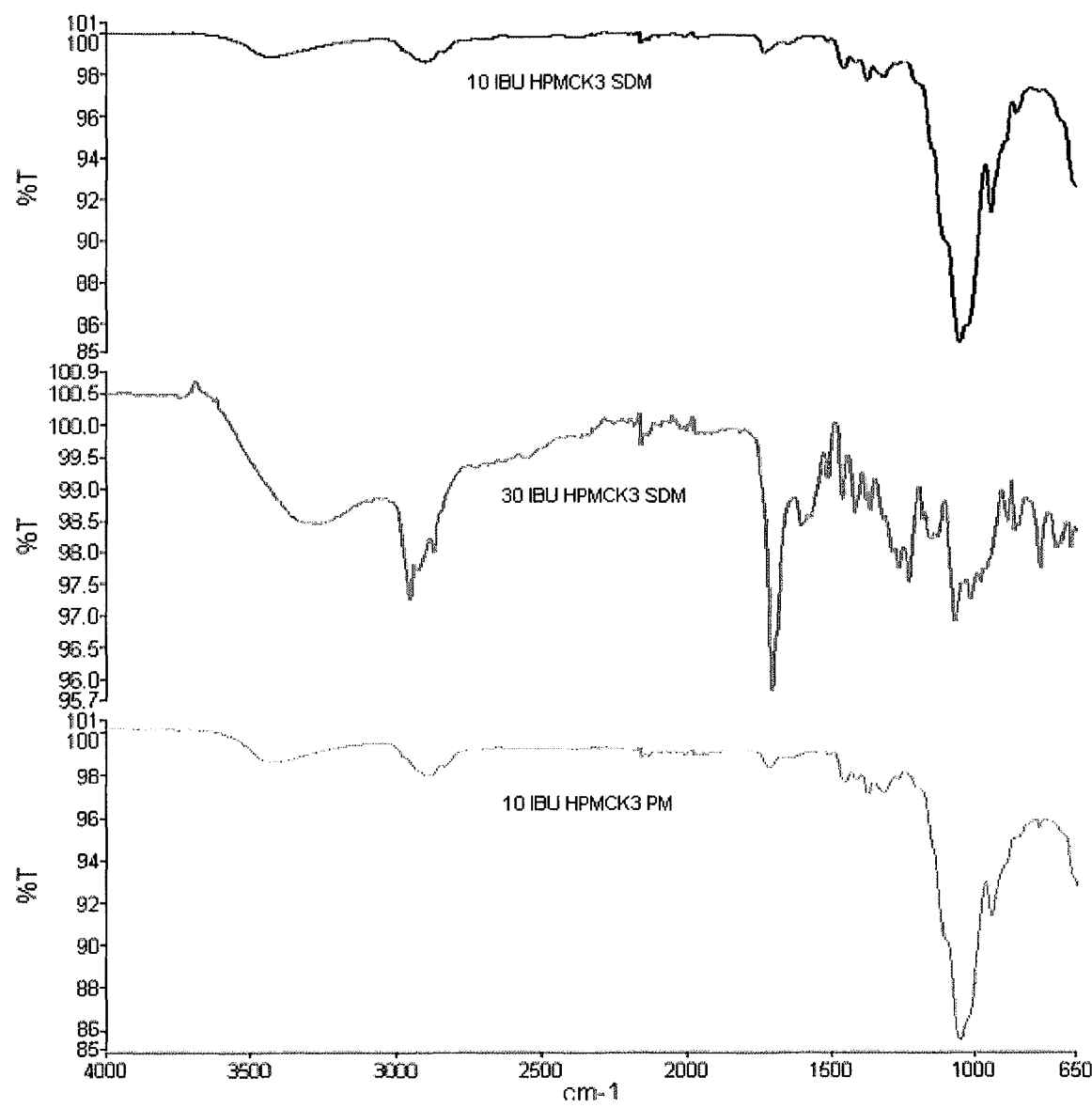

The FTIR spectra are shown in FIGS. 11A-E. NEAT IBU showed a sharp band associated with carboxylic acid stretching of dimeric IBU at 1708.7 $cm^{-1}$ and another band at 2954 $cm^{-1}$ associated with OH stretching. Dimeric IBU showed IR spectra at 1710 $cm^{-1}$. The major IR bands characteristic of AGF were 3300-3500 cm-1 associated with OH stretching, 2891.31 $cm^{-1}$ associated with C—H stretching in CH2 and CH3, and 1590 $cm^{-1}$ due to carboxylate stretch were present in NEAT AGF FTIR spectra. No covalent bonding between the therapeutic agent and the arabinogalactan is detected in the FTIR data for the IBU AGF MSD formulations (FIG. 11A), the IBU AGF SDM formulations (FIG. 11B), or the IBU AGF PM formulations (FIG. 11C).

In the present investigation, the IR spectrum of PM formulations was found to be the algebraic sum of the IR spectra of pure drug and of pure polymer with no significant shifts in the major IBU IR bands. In fact, the IR band at around 1710 cm$^{-1}$ was present in PM formulation suggesting dimeric IBU.

The C=O stretching band of IBU was shifted to a higher wave number in SDM, MSD at least by a value of 4 cm$^{-1}$-10 cm$^{-1}$. On the other hand, the IR band of OH group of AGF polymer showed apparent shifts in MSD and SDM formulations as well. Thus, the blue shift in C=O of IBU and the shift in the OH of AGF were associated with hydrogen bonding between those two groups.

The corresponding shift or absence (20% SDM and 30% SDM) in the IR band at 3308 cm-1 due to OH stretching of the AGF was observed, suggesting hydrogen bonding between the C=O of IBU and the OH of AGF polymer. However, no specific trend i.e. blue or red shift with the formulation or with different drug polymer ratios was observed with this OH group.

There was no significant shift in the IR band at 2954 cm$^{-1}$ due to OH stretching of IBU in any of the formulations, suggesting that this group may not take part in hydrogen bonding extensively between the IBU and AGF.

The carboxylate stretching band of AGF (1590 cm$^{-1}$) was shifted in SDM, MSD and PM formulation indicating modified environment due to hydrogen bonding. Thus, hydrogen bonding between IBU C=O and AGF OH was extensive.

The presence of hydrogen bonding in IBU AGF SD but not in PM formulation confirmed the melting point depression observed in DSC scans of these solid dispersions. The results further emphasized that the presence of hydrogen bonding in IBU AGF SD was associated with amorphization of IBU in these formulations.

Thermomechanical Analysis (TMA)

TMA was carried out on SDM and PM formulations. TMA measurements were performed on a Q400 TMA equipped with a penetration proble (TA Instruments, New Castle, Del.). Approximately 5 mg of sample was compacted into a disc using a sample press (TA Instruments, New Castle, Del.) and then placed on a glass stage for analysis. The protocol included a heating rate of 10 C/min up to 160 C and applied a force of 0.02N. The thickness of the compact was 1.4 to 2 mm. Nitrogen at a rate of 200 ml/min was used as a washing gas. Universal Analysis 2000 software (TA Instruments, New Castle, Del.) was used to acquire and analyze the data.

TMA was used to measure the glass transition temperature (Tg). TMA measures the dimensional changes as a function of temperature. TMA is based on the principle that at the Tg of a polymer, the polymer chains are moving and their inter and intra segmental bonds are strongly reduced. Thus, free volume increases and so does the flexibility and penetrability of the polymer. Therefore at Tg there is a minimum resistance to penetration.

Figure 12:
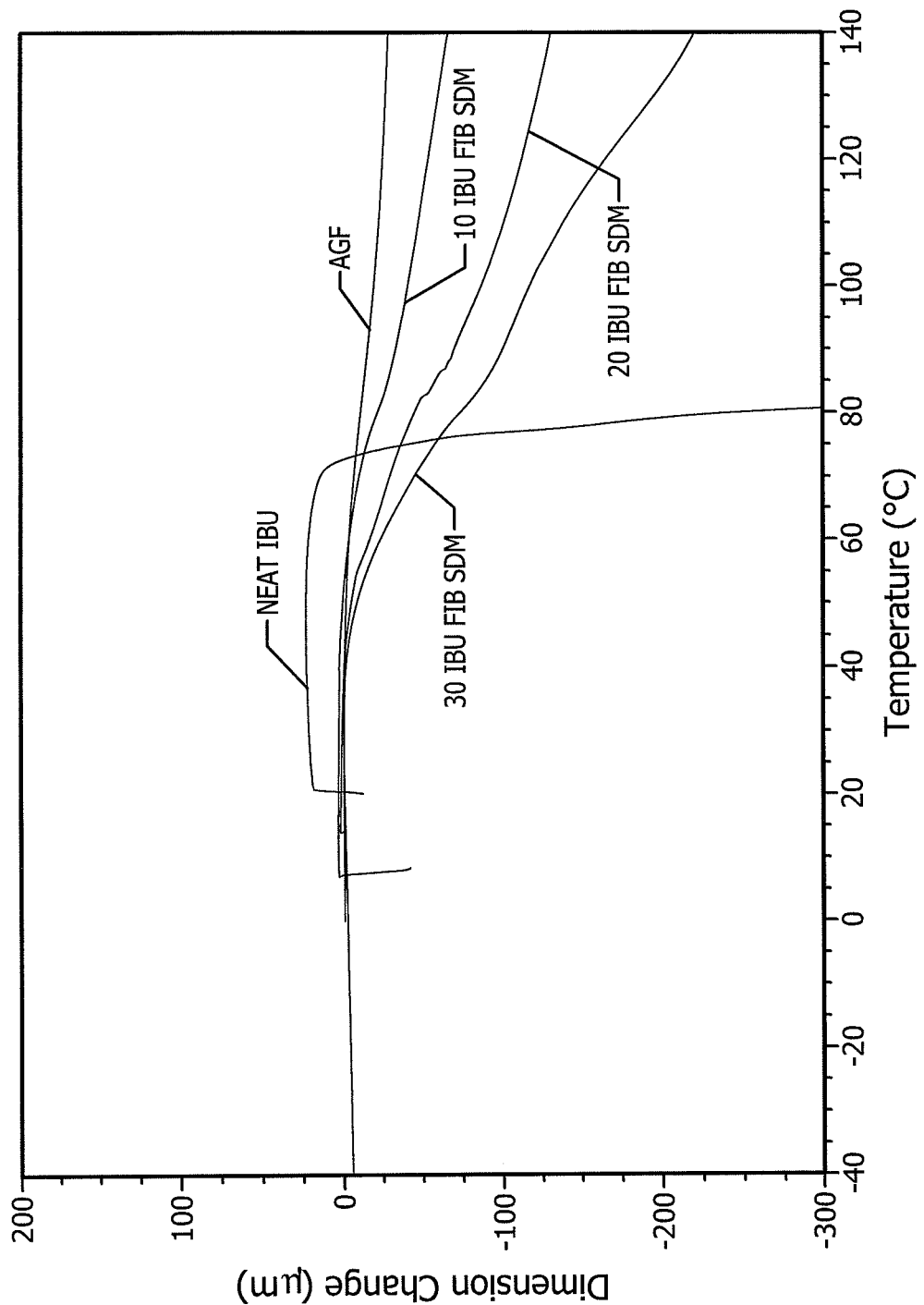
FIG. 12 shows the Thermomechanical Analysis (TMA) scan of IBU AGF ("FIB" on the graph) SDM formulations at various drug loads. From bottom to top at the 81° C. mark are shown: NEAT IBU, 30% IBU AGF SDM, 20% IBU AGF SDM, 10% IBU AGF SDM and AGF.

TMA was carried out for ibuprofen-AGF SDM formulations at drug loads of 10%, 20% and 30% (FIG. 12). The 10% IBU AGF SDM formulation showed one Tg (78.14 θC) demonstrating that IBU and AGF are miscible and homogeneously mixed at the molecular level. The TMA scan of 20% IBU AGF SDM showed two thermal events (58.03 θC and 83.88 θC). The first one was the melting of crystalline IBU and the second one was the Tg of the binary suspension where the drug was molecularly dispersed into the amorphous AGF matrix. Three transitions were observed for 30% IBU AGF SDM, at 58.38 θC, 79.22 θC and 117.82 θC. The first transition was the melting of the crystalline IBU which was also observed in the 20% IBU AGF SDM formulations. The second and third transitions were the Tg's of the IBU AGF dispersion. Thus, multiple phases were present at 20% and 30% drug load. However, the ibuprofen was completely amorphous at 10% drug load in the IBU AGF SDM formulation.

TABLE 6

Experimental and theoretical Tg of IBU AGF formulations.

| Formulations | Experimental Tg/ Thermal Transition (° C.) | Predicted Tg (° C.) (Fox's Equation) | Predicted Tg) (° C.) (Couchman-Karasz equation) |
|---|---|---|---|
| NEAT IBU | −45 (Tg) and 78.09 (Tm) | — | — |
| 10% IBU AGF SDM | 78.14 (Tg) | 58.38 | 72.67 |
| 20% IBU AGF SDM | 58.03 (Tm); 83.88 (Tg) | 46.26 | 63.92 |
| 30% IBU AGF SDM | 63.67 (Tm); 79.54 (TgI); 124.49(TgII) | 31.02 | 52.52 |
| AGF | 82 (Tg) | — | — |

Example 5. In Vitro Drug Dissolution Studies

Basket Method

The in vitro drug dissolution rates of PMs and MSDs made with ibuprofen and AGF or HPMCK3 were determined by the USP basked method (270 mesh, 53 micron pore size). The Van Kel VK7010 dissolution system was employed. 900 ml of 0.1 N HCl at 37° C. was used as a dissolution medium. The media was selected to mimic gastric pH and to allow greater discrimination of ibuprofen dissolution profiles due to formulation and processing effects. The dissolution experiment was run at 100 rpm. Each sample contained an MSD or a PM equivalent to 25 mg of ibuprofen to maintain the non sink conditions, i.e. to employ a volume of medium (900 ml in this case) that is less than the volume of medium required for sink conditions, which is three times that required in order to form a saturated solution of drug. In vitro dissolution of 25 mg of neat ibuprofen was used as a control. At appropriate time intervals, samples were collected and replaced by fresh media. Each sample was filtered and the drug was analyzed using Agilent/HP 8453 UV-Vis spectrophotometer (λmx=222 nm). The experiment was conducted in triplicate. T50 (time for 50% drug release), T60 (time for 60% drug release), and T80 (time for 80% drug release) was recorded directly from the dissolution profiles. See Table 7 below.

TABLE 7

T50 (time for 50% drug release), T60 (time for 60% drug release), and T80 (time for 80% drug release) for IBU AGF SD and IBU AGF PM formulations.

| Formulation | T50 | T60 | T80 |
|---|---|---|---|
| Neat IBU | 19 min | 300 min | Greater than 400 min |
| 10% IBU AGF MSD | 5 min | 6 min | 10 min |
| 20% IBU AGF MSD | 7 min | 9 min | 25 min |
| 30% IBU AGF MSD | 7 min | 10 min | 50 min |
| 10% IBU AGF SDM | 4 min | 5 min | 9 min |
| 20% IBU AGF SDM | 8 min | 12 min | 55 min |
| 30% IBU AGF SDM | 140 min | Greater than 150 min | Greater than 150 min |
| 10% IBU HPMCK3 SDM | 12 min | 15 min | 35 min |
| 30% IBU HPMCK3 SDM | 25 min | 36 min | 72 min |
| 10% IBU AGF PM | 11 min | 40 min | 170 min |
| 20% IBU AGF PM | 72 min | 105 min | 250 min |
| 30% IBU AGF PM | 95 min | 150 min | 320 min |

TABLE 7-continued

T50 (time for 50% drug release), T60 (time for 60% drug release), and T80 (time for 80% drug release) for IBU AGF SD and IBU AGF PM formulations.

| Formulation | T50 | T60 | T80 |
|---|---|---|---|
| 10% IBU HPMCK3 PM | 52 min | 62 min | 100 min |
| 30% IBU HPMCK3 PM | 70 min | 100 min | 220 min |

Figure 13:
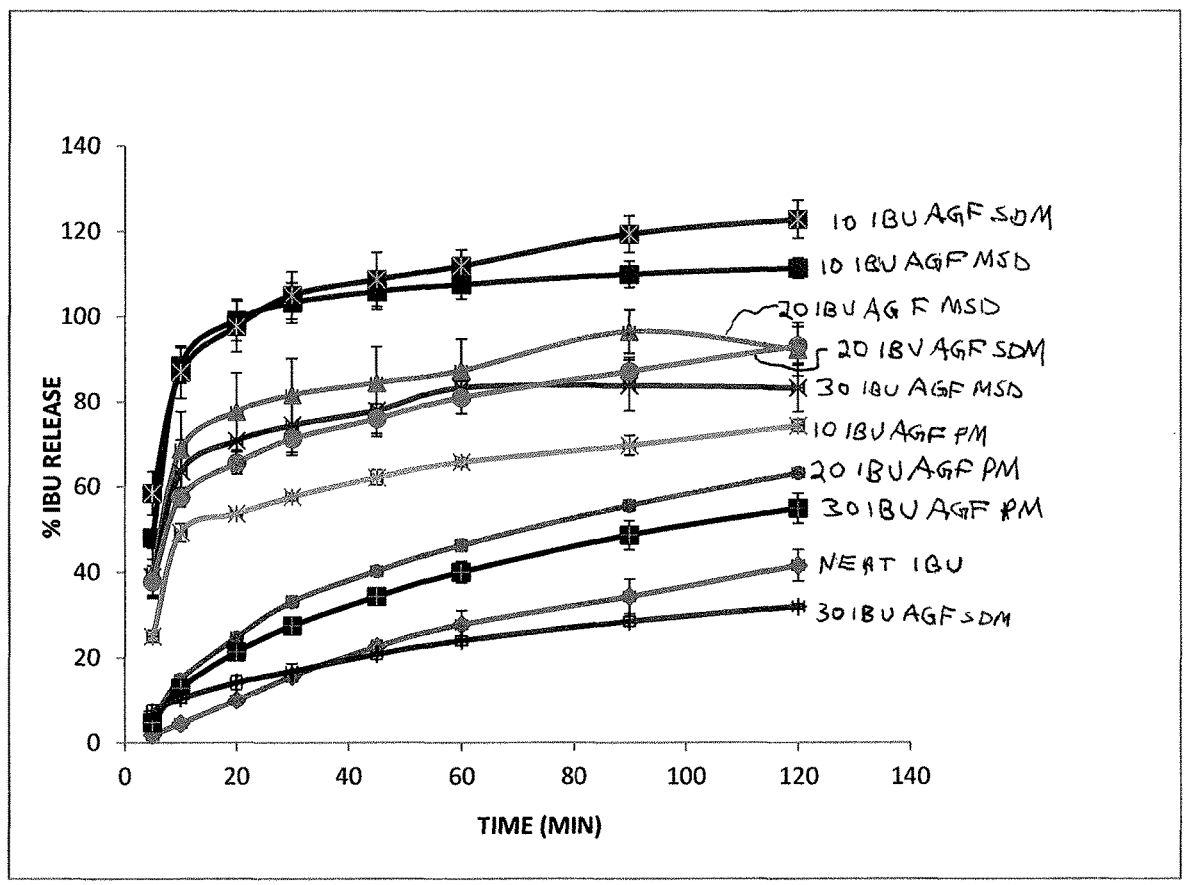
FIG. 13 shows the dissolution profiles of IBU AGF MSD, IBU AGF SDM and IBU AGF PM in 0.1 N HCl.

The mean (n=3) dissolution profiles of the IBU AGF MSD and IBU AGF SDM are shown in FIG. 13. Statistical analysis of the dissolution data showed significantly faster dissolution for MSD, 10% SDM, 20% SDM and 10% PM formulation compared to the NEAT IBU. The differences between the dissolution profiles of MSD formulation, 10% SDM and 20% SDM formulations were not statistically significant from each other. 10% MSD formulations resulted in significantly greater dissolution than all PM formulations and than 30 SDM formulation. The dissolution profiles of each 20% MSD and 30% MSD formulation were statistically equivalent to the dissolution profiles of 10% PM but were significantly greater than the individual dissolution profiles of 20% PM and 30% PM formulation. The dissolution of 10% SDM and 20% SDM formulation was significantly greater than that of 30% SDM formulation. In general, the IBU release was greater for MSDs/SDMs than for PMs. However, there was no significant difference between 20% SDM and 30% SDM. The dissolution profiles of PM formulations were statistically equivalent. Thus, IBU release with respect to the DL was in the order: 10% DL>20% DL>30% DL for MSD, for SDM as well as for PM formulations.

The relative standard deviation (RSD) values were 11-14% at the early time point and ranged from 3% to 8% at the later time points for MSD formulations. For the SDM formulation initial time point % RSD was found to be 8-18% and less than 7% at later time points. For PM formulations, initial time point % RSD values were 11% (20% PM) and 19% (30% PM) and were below 7% at the latter time points.

The enhanced dissolution of IBU from MSD and SDM formulations can be ascribed to drug amorphization, hydrogen bonding and solution state complex formation as is evident from solid state and solution state studies. The solubilization effect of AGF also contributes to the observed dissolution enhancement. Particle size reduction, the wetting effect of the carrier and the surface tension lowering effect of the carrier were other auxiliary factors that led to dissolution enhancement.

Figure 14A:
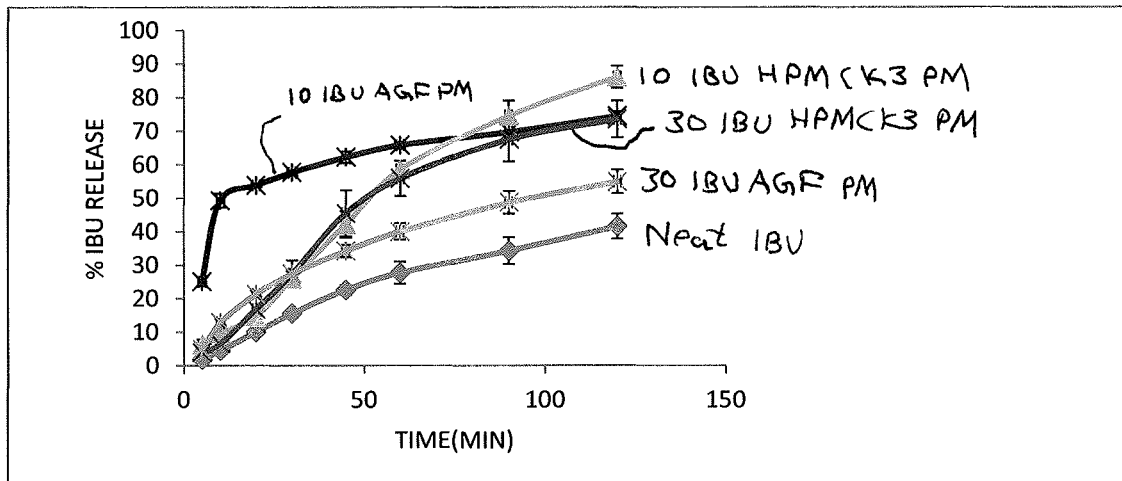
FIG. 14A shows the dissolution profiles of IBU AGF PM and IBU HPMCK3 PM in 0.1 N HCl.
Figure 14B:
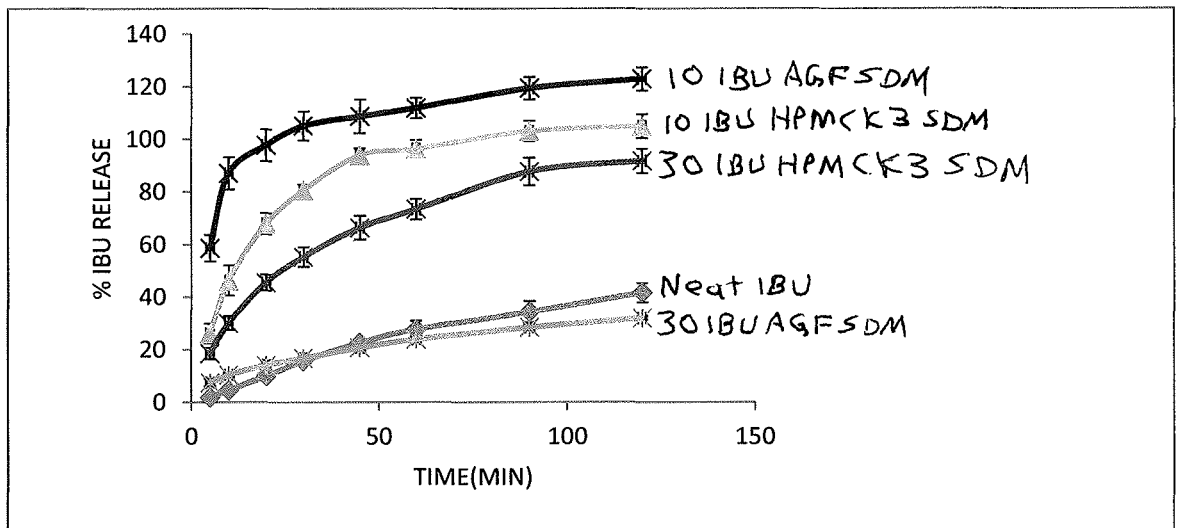
FIG. 14B shows the dissolution profiles of IBU AGF SDM and IBU HPMCK3 SDM in 0.1 N HCl.

The in vitro dissolution profiles of IBU PM (FIG. 14A) and IBU SDM (FIG. 14B) prepared with AGF and HPMCK3 polymer were compared to gain insight into the dissolution enhancement potential of the two carriers. 10% DL and 30% DL were chosen as the lowest and the highest DLs.

Dissolution of 10% AGF PM was found to be significantly higher compared to that of NEAT IBU, however there was no difference in the dissolution of NEAT IBU and 30% AGF PM, 10% HPMCK3 or 30% HPMCK3 PM. The dissolution of all physical mixture formulations was statistically equivalent. However, after the statistical analysis of the dissolution data up to 30 minutes, 10% IBU AGF PM showed a faster initial dissolution rate compared to the 10% IBU HPMCK3 PM. After 40 minutes, although increased IBU dissolution was observed for 10% IBU HPMCK3 PM compared to the NEAT IBU, it was constantly slow compared to the 10% IBU AGF PM.

As the DL increased to 30%, the dissolution profiles of physical mixtures of AGF and HPMCK3 were comparable. In fact, after 30 minutes the 30% IBU HPMCK3 PM showed a higher dissolution rate, although it was not statistically significant compared to 30% IBU AGF PM. The reduced HPMCK3 content reduced the viscosity and gel forming ability of the carrier resulting in enhanced dissolution. It was evident that at the polymer load of 30%, it took 30 minutes for the HPMCK to get into the solution and to exert its solubilization and surfactant effect to enhance drug dissolution.

Statistically faster dissolution rates were observed for 10% IBU AGF SDM, 10% IBU HPMCK3 SDM, 30% IBU HPMCK3 SDM compared to the dissolution of neat IBU. The dissolution profiles of 10% IBU AGF SDM and 10% IBU HPMCK3 SDM were statistically equivalent. However, the order of dissolution was 10% IBU AGF SDM>10% IBU HPMCK3 SDM. 10% IBU AGF SDM had a significant dissolution enhancement compared to 30% IBU AGF SDM and 30% IBU HPMCK3 SDM.

HPMCK3 enhances dissolution probably via its surfactant activity and possibly by its precipitation inhibition activity only when the viscosity barriers are crossed at and above 30% DL. Thus, below 30% DL, AGF polymer was found to better enhance the dissolution of model drug IBU than HPMCK3.

Overall, the AGF solid dispersions were superior in terms of porosity, pulverability and dissolution enhancing power to the HPMCK3 solid dispersions, up to 20% drug load.

Example 6. Characterization of Ketoprofen-Arabinogalactan and Itraconazole-Arabinogalactan Solid Dispersions Preparation of ITRA AGF and KETO AGF Solid Dispersions by Modified Solvent Evaporation Method (SDM)

The method was as described in Example 2 and was revised as follows. This method may be used for drugs such as ITRA and KETO for which a saturated solution could not be obtained with a workable ethanol volume.

A physical mixture of AGF with itraconazole (ITRA) or ketoprofen (KETO) was placed in a round bottom flask. Nanopure water was added to the physical mixture to obtain a wet mass. 5-7 ml of ethanol was added at once to this polymer mass. The entire solvent was removed using rotovap evaporation at 70° C. under vacuum. It took 45 minutes to 2 hours (depending on the drug load) to obtain the desired SDM mass. To ensure complete drying, the SDM samples were kept in oven at 45° C. overnight. The prepared SDM samples were stored in an airtight container until further analysis.

Equilibrium Solubility-Method

An equilibrium solubility study of ITRA and KETO was carried out in the presence of various concentrations of AGF (in 0.1N HCl) according to the Higuchi and Connors (1965) Adv. Anal. Chem. Instrum. 4(117): 212, method with a few modifications. An excess of IBU (200 mg) was added to 10 ml of polymer solution in 0.1N HCl in a stoppered glass vial and was bath sonicated for 30 minutes. The polymer concentrations ranged from 0% to 3% (0 mg/ml to 30 mg/ml). The vials were kept in a shaking water bath at 37 C and at 50 rpm for 72 hours to obtain equilibrium. After 72 hours the shaker was turned off and the samples were kept at a standstill at 37 C for 3 hours to settle the undissolved drug at the bottom of the glass vials. The supernatant was filtered using a 0.45 micron filter.

For an equilibrium study of itraconazole, 50 mg itraconazole (ITRA) was added to 20 ml of AGF polymer solution in 0.1 N HCl. The ITRA content was assayed using UV absorption at 257 nm (Agilent/HP 8453 UV-Vis spectrophotometer) after suitable dilution.

For an equilibrium study of ketoconazole, 400 mg of ketoconazole (KETO) was added to 10 ml of arabinogalactan polymer solution in 0.1 N HCl. KETO content was assayed using UV absorption at 260 nm (Agilent/HP 8453 UV-Vis spectrophotometer) after suitable dilution.

Equilibrium Solubility-Results

Figure 15:
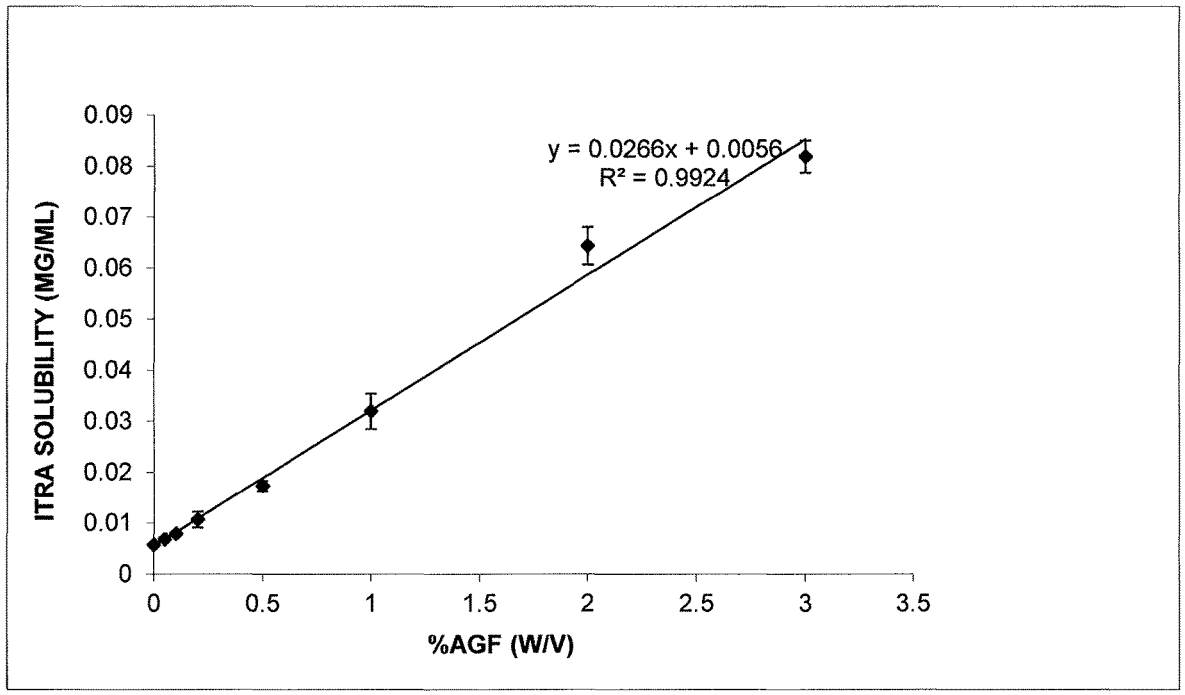
FIG. 15 shows the equilibrium solubility of itraconazole (ITRA) in the presence of AGF polymer solution in 0.1N HCl.

The solubility of neat ITRA was found to be 5.72 mg/ml (FIG. 15). A linear increase in solubility was observed with an increase in arabinogalactan concentration up to 3% (w/v). At 3% arabinogalactan concentration a 16-fold increase in ITRA solubility was observed.

Figure 16:
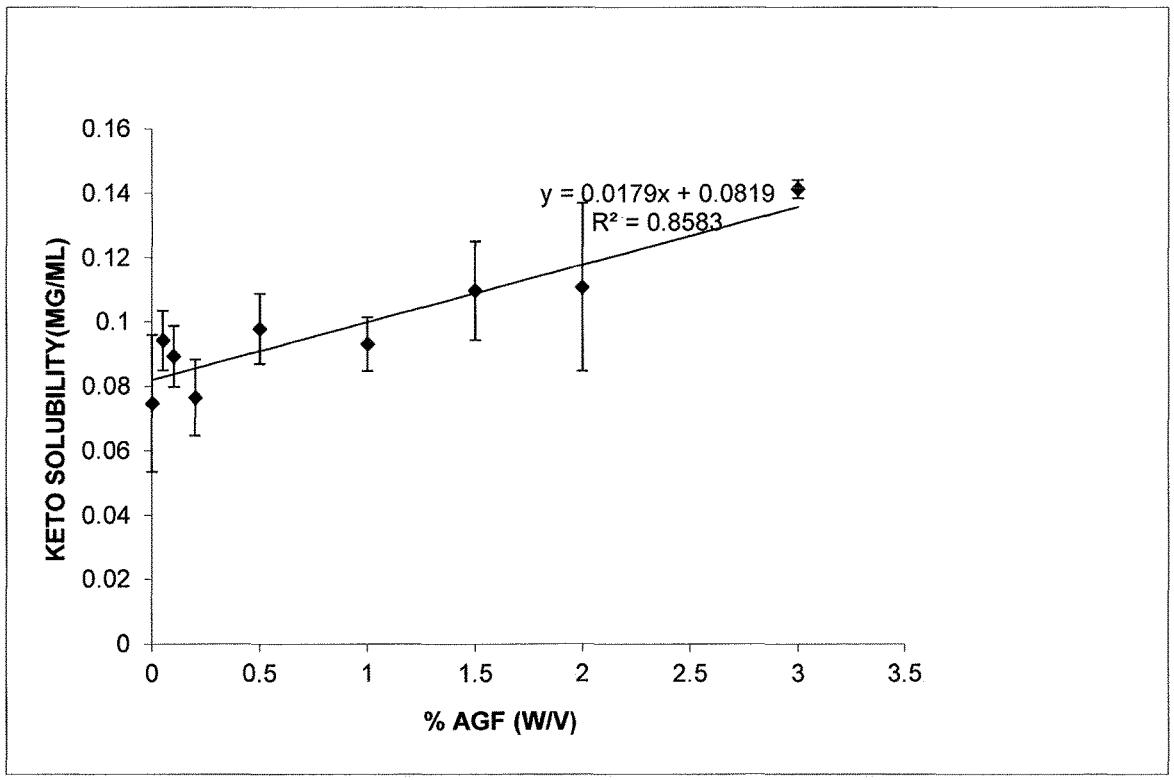
FIG. 16 shows the equilibrium solubility of ketoprofen (KETO) in the presence of AGF polymer solution in 0.1N HCl.

The equilibrium solubility of neat KETO was found to be 0.074 mg/ml (FIG. 16). The solubility of KETO increased linearly as a function of AGF concentration (AGF range of 0.05% to 3%). At AGF concentration of 3%, a 2-fold increase in solubility was observed. Thus, AGF exerted a solubilizing effect on KETO.

Conventional Differential Scanning Calorimetry (DSC)

DSC was carried out on SDM and PM formulations as described in Example 2.

Figure 17:
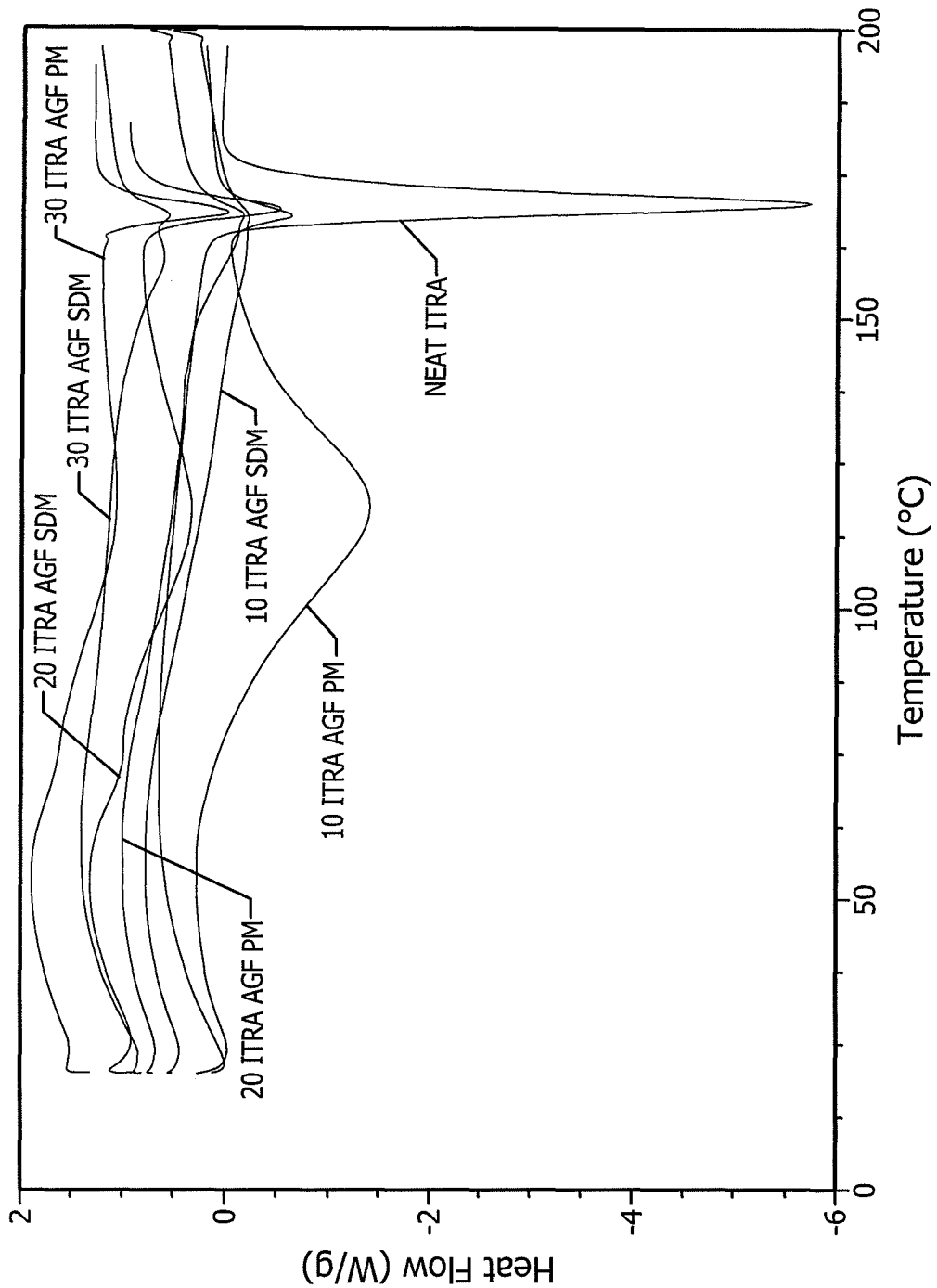
FIG. 17 shows DSC thermographs of ITRA AGF formulations. From bottom to top (at the 50° C. mark) are shown: 10% ITRA AGF PM, NEAT ITRA, 10% ITRA AGF SDM, 20% ITRA AGF PM, 20% ITRA AGF SDM, 30% ITRA AGF SDM, 30% ITRA AGF PM.

Almost complete amorphization of ITRA took place in AGF SDM formulations for up to 30% drug load (FIG. 17). The loss in crystallinity was associated with melting point depression in SDM formulations (Table 8). The DSC thermograms of ITRA formulations did not show an endotherem at about 70° C. and about 90° C. indicative of ITRA nematic mesophase (glassy ITRA). This suggests that ITRA was either molecularly dispersed in the AGF or was present in separate crystalline form in physical mixtures.

TABLE 8

DSC melting point depression in DRUG AGF formulations.

| FORMULATIONS | DSC Melting point ITRA AGF formulations | DSC Melting point KETO AGF formulations | DSC Melting point IBU AGF formulations |
|---|---|---|---|
| NEAT DRUG | 169.92 | 96.53 | 76.56 |
| 10% AGF SDM | 167.79 | 0 | 0 |
| 20% AGF SDM | 167.66 | 0 | 72.80 |
| 30% AGF SDM | 167.49 | 0 | 74.02 |
| 10% AGF PM | 169.49 | 0 | 73.48 |
| 20% AGF PM | 168.78 | 85.96 | 74.04 |
| 30% AGF PM | 168.52 | 83.88 | 74.57 |

Figure 18:
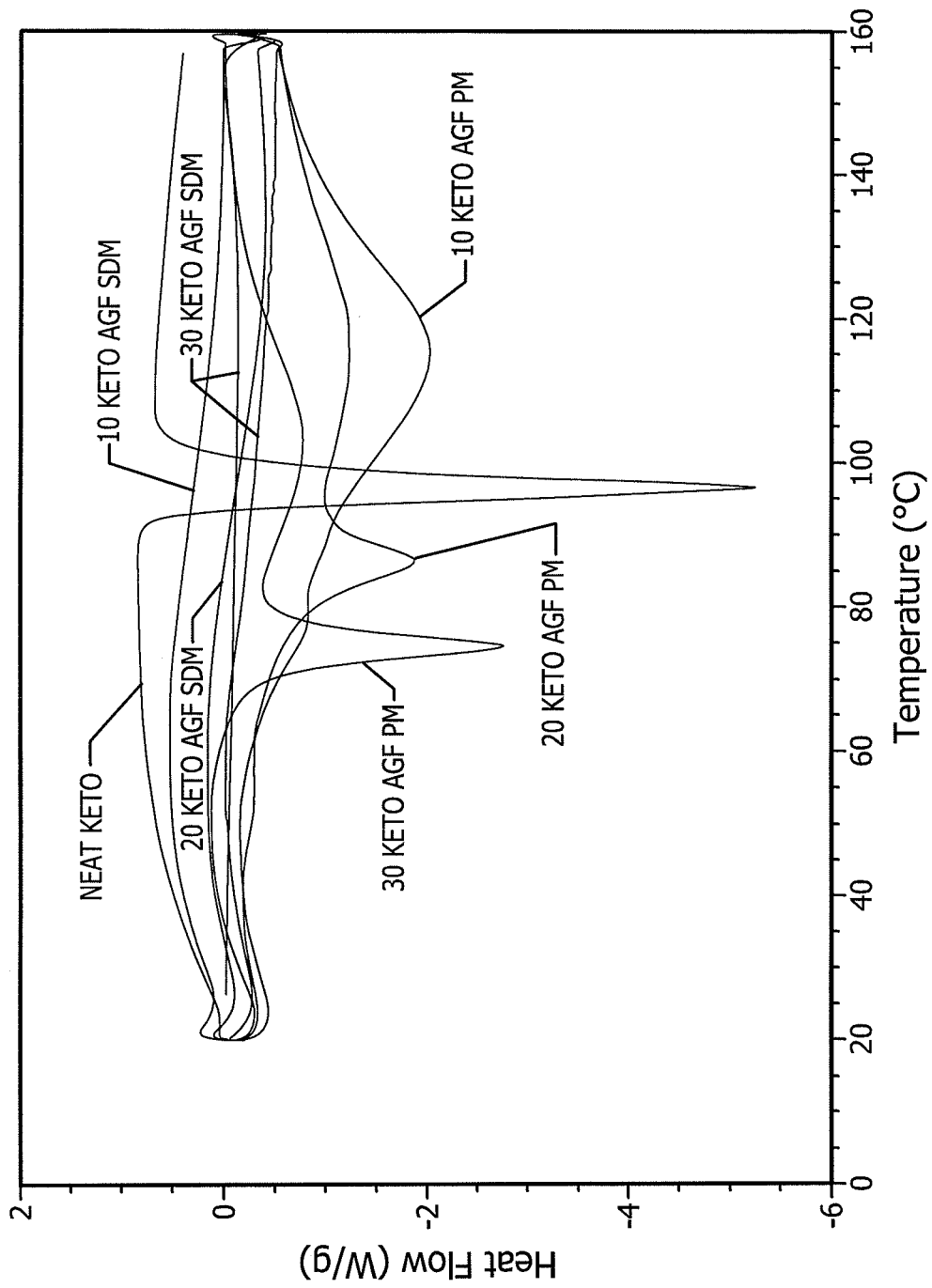
FIG. 18 shows DSC thermographs of KETO AGF formulations. From bottom to top (at the 110° C. mark) are shown: 10% KETO AGF PM, 20% KETO AGF PM, 30% KETO AGF PM, 30% KETO AGF SDM, 20% KETO AGF SDM, 10% KETO AGF SDM, NEAT KETO.

KETO was found to be fully amorphous up to 30% DL in AGF solid dispersion formulation (FIG. 18). Complete loss of KETO crystallinity was also found in 10% KETO AGF PM formulation. Broadening of the endotherm with melting point depression was observed for 20% KETO AGF PM formulations suggesting disorder in these formulations as well.

Powder X-Ray Diffraction (XRPD)

XRPD were collected using Rigaku D-Max B X-ray Diffractometer (Tokyo, Japan). The powder sample size of 0.5 gram was used and samples were run at 35 kV at 15 mA and 0.9 W. JADE software (version 9) was used to process, acquire and analyze the data.

Figure 19:
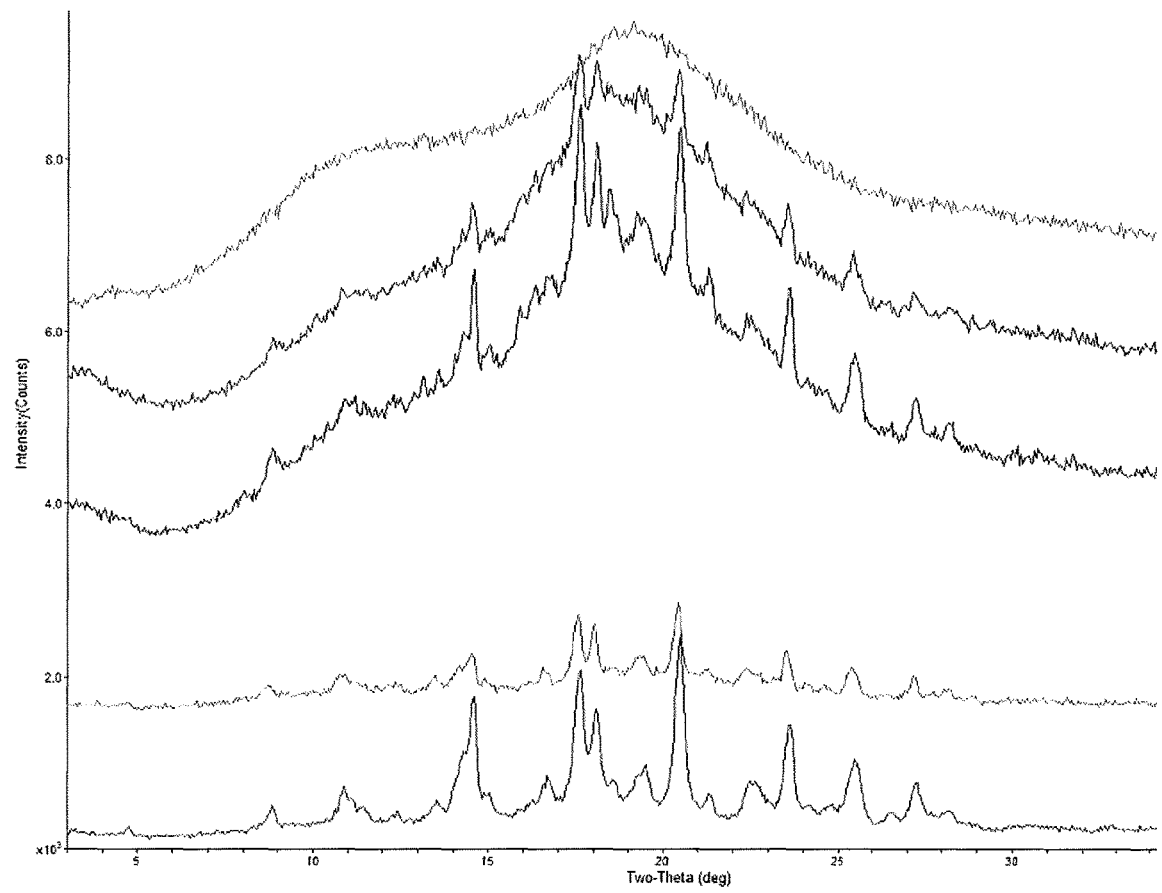
FIG. 19 shows an XRPD overlay of ITRA AGF PM formulations. From bottom to top at the 10 Two-Theta mark are shown: NEAT ITRA, 30% ITRA AGF PM, 20% ITRA AGF PM, 10% ITRA AGF PM, NEAT AGF.

The distinct peaks corresponding to ITRA crystallinity were present at 14.59°, 17.64°, 20.49°, 23.60°, 25.50° and 27.25° at 2θ (FIG. 19). Disappearance of some XRPD peaks and significant reduction in the remaining XRPD peaks were observed for SDM formulations especially for 10% and 20% ITRA SDM formulations. However, shifts in the XRPD peaks associated with reduction in intensity were observed for 30% ITRA SDM formulations which confirmed the DSC findings of presence of crystalline ITRA in this formulation. Minute amounts of crystalline ITRA were present in SDM formulations. However, physical mixtures retained ITRA in completely crystalline form.

Figure 20:
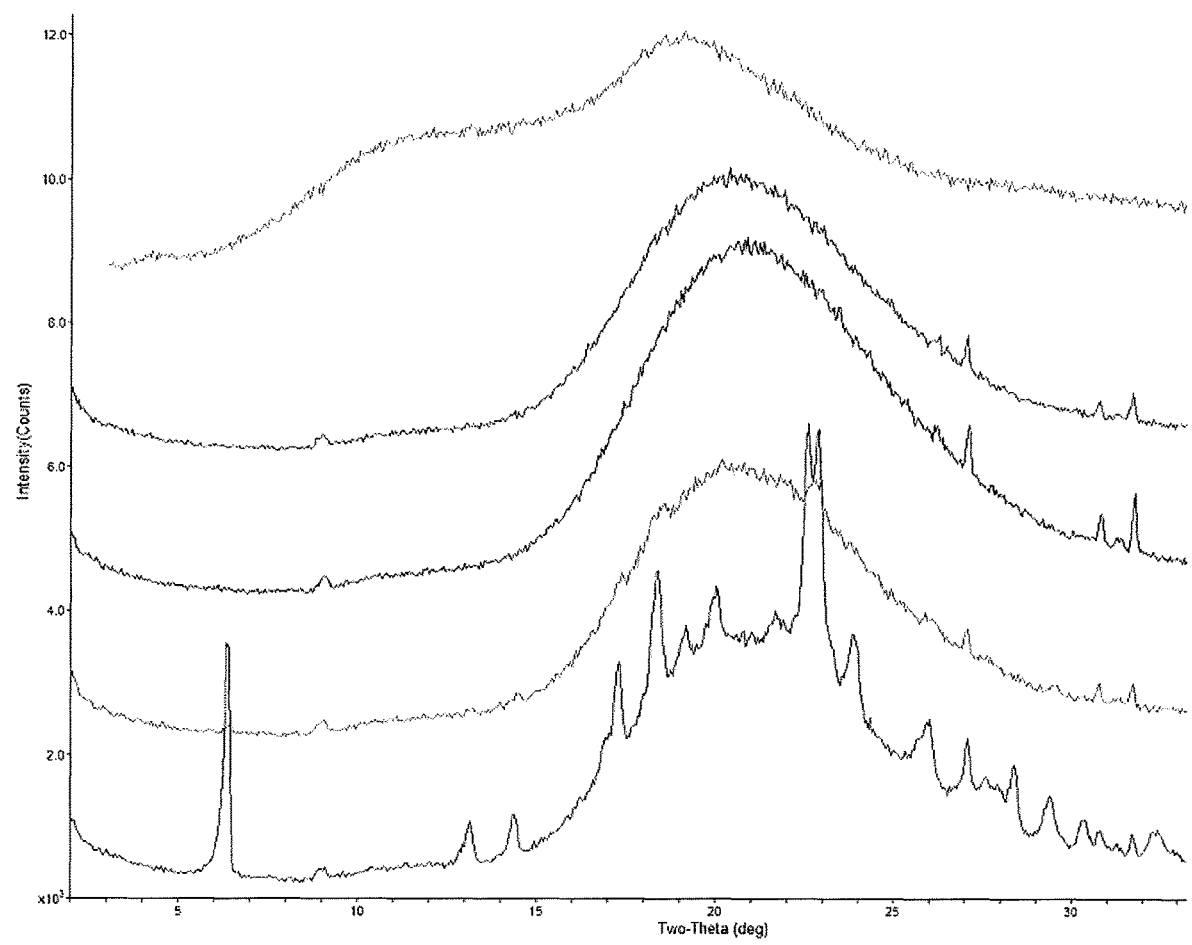
FIG. 20 shows the XRPD overlay of KETO AGF SDM formulations. From bottom to top at the 10 Two-Theta mark are shown: NEAT KETO, 30% KETO AGF SDM, 20% KETO AGF SDM, 10% KETO AGF SDM, NEAT AGF.

FIG. 20 shows the overlay of the XRPDs of the KETO AGF SDM formulations. The high intensity diffraction peaks at 6.3°, 13.14°, 17.3°, 18.3°, 20.04°, 22.6° and 23.85° are attributed to KETO crystallinity. The XRPD spectra of NEAT KETO matches to the literature results (Manna et al., 2007, *J Supercritical Fluids* 42(3):378-384). The crystalline peak of KETO shifted from 22.6 to 22.9 in the KETO AGF formulations. This could be due to crystalline transformation of the KETO due to processing in the presence of AGF either at room temperature (physical mixtures) or at high temperature (SDM formulations). The KETO crystallinity peaks completely disappeared in 10% SDM, 20% SDM and 10% PM formulations and the remaining peaks were present with reduced intensity. The XRPD peak at 22.6° (2θ) was present with very low intensity in 30% SDM.

SEM

SEM was conducted on SDM and PM formulations as described in Example 2.

Figure 21:
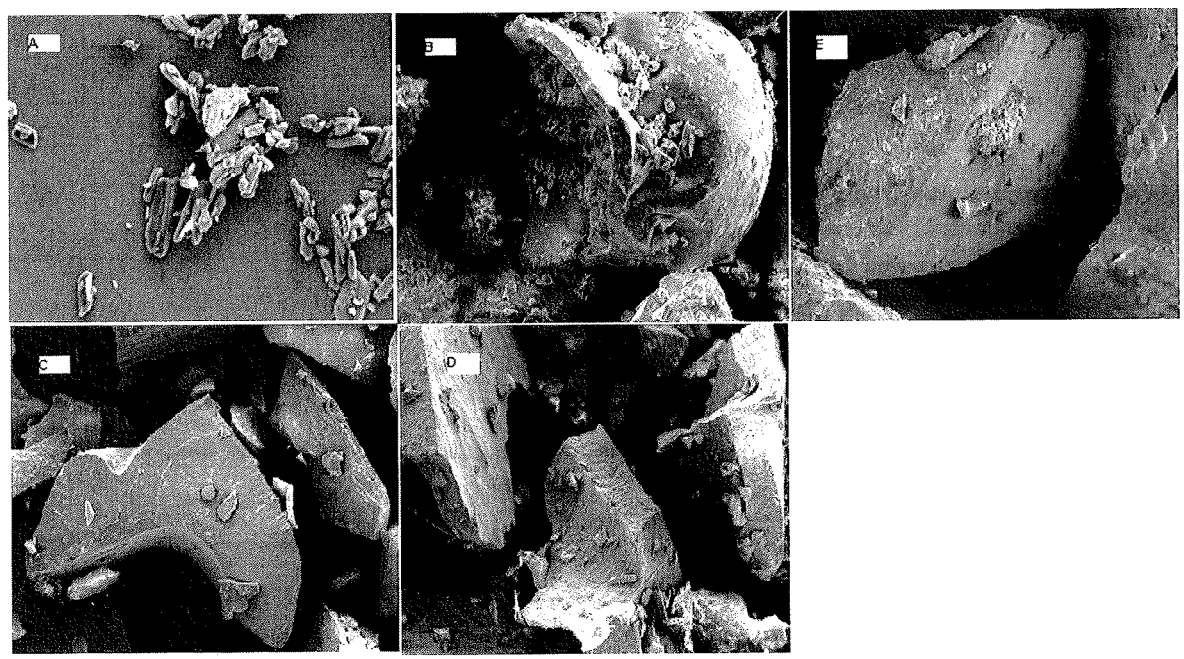
FIG. 21 shows scanning electron micrographs of ITRA AGF formulations. A: Neat ITRA, B: 10% ITRA AGF PM, C: 10% ITRA AGF SDM, D: 20% ITRA AGF SDM, E: 30% ITRA AGF SDM.

FIG. 21 clearly shows the presence of crystalline ITRA in 10% PM formulation and absence of crystalline drug in up to 20% drug load SDM formulations. Very low amounts of crystalline ITRA were observed in 30% drug load SDM formulations.

Figure 22:
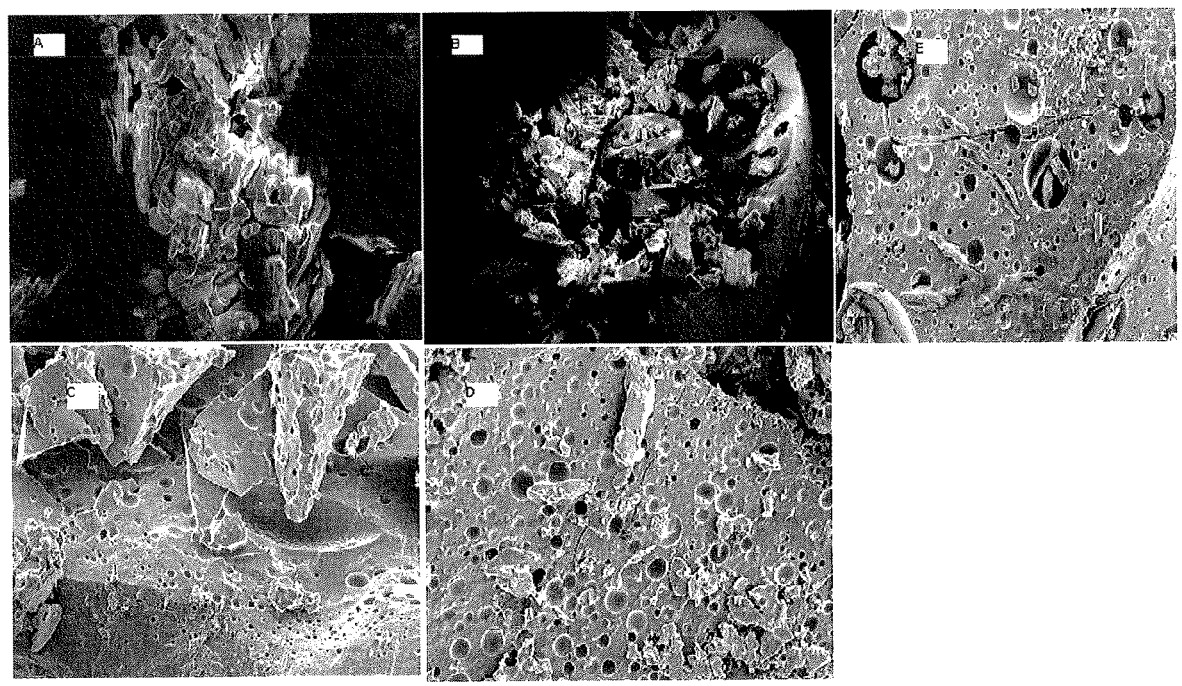
FIG. 22 shows scanning electron micrographs of KETO AGF formulations. A: Neat KETO, B: 10% KETO AGF PM, C: 10% KETO AGF SDM, D: 20% KETO AGF SDM, E: 30% KETO AGF SDM.

FIG. 22 also shows crystalline KETO in 10% PM formulation and absence of crystalline KETO in up to 20% drug load SDM formulations. FIG. 22 clearly shows that a very low amount of crystalline KETO was present in 30% SDM formulations.

Together, these results suggest the formation of amorphous ITRA and KETO arabinogalactan SDM formulations of almost up to 30%. The results also indicate that the SDMs comprise an arabinogalactan polymer matrix and a therapeutic agent uniformly dispersed in the matrix. At drug loads of up to 20%, the drug is not confined or concentrated in channels or pores of the matrix.

FTIR

Figure 23A:
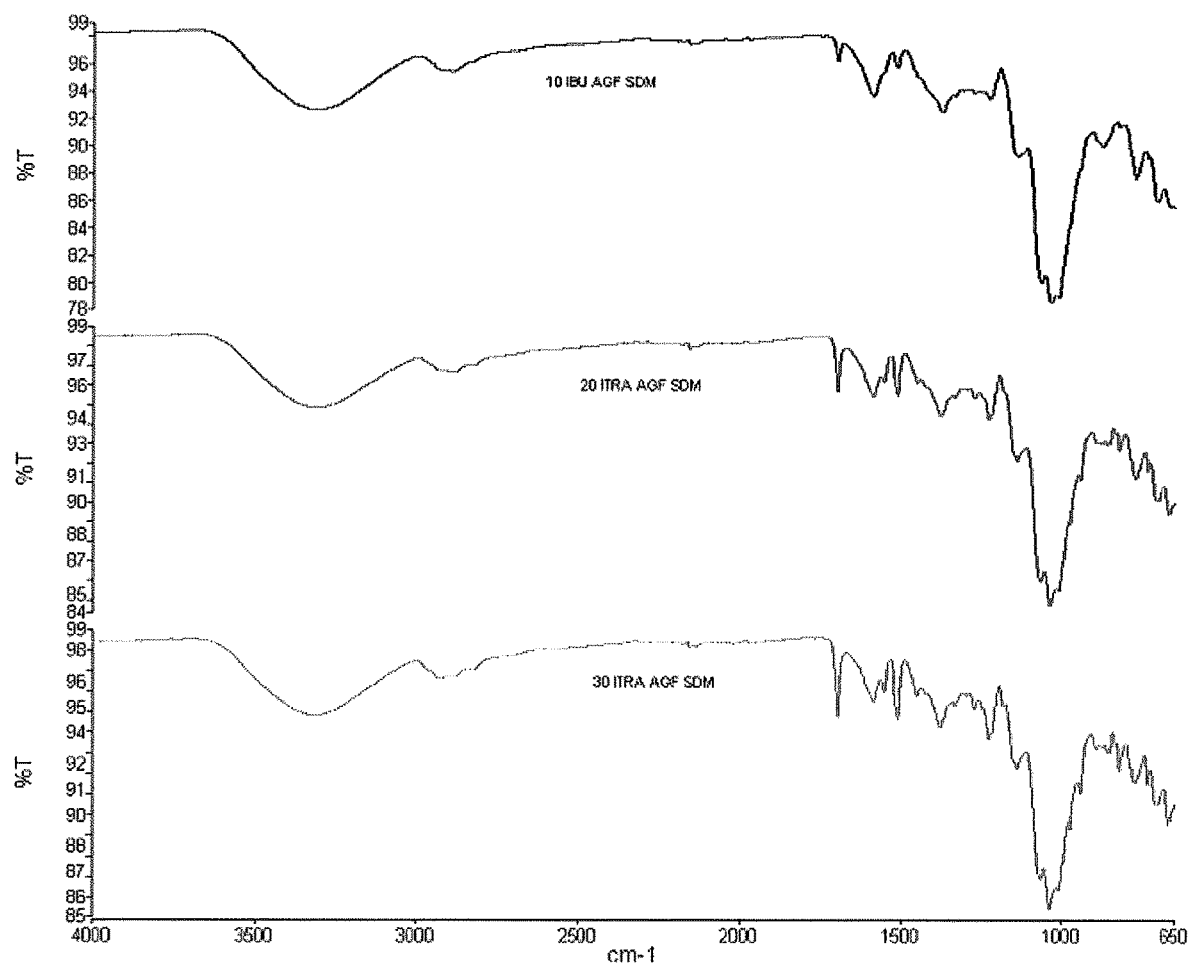
FIG. 23A shows FTIR spectra of ITRA AGF SDM formulations.
Figure 23B:
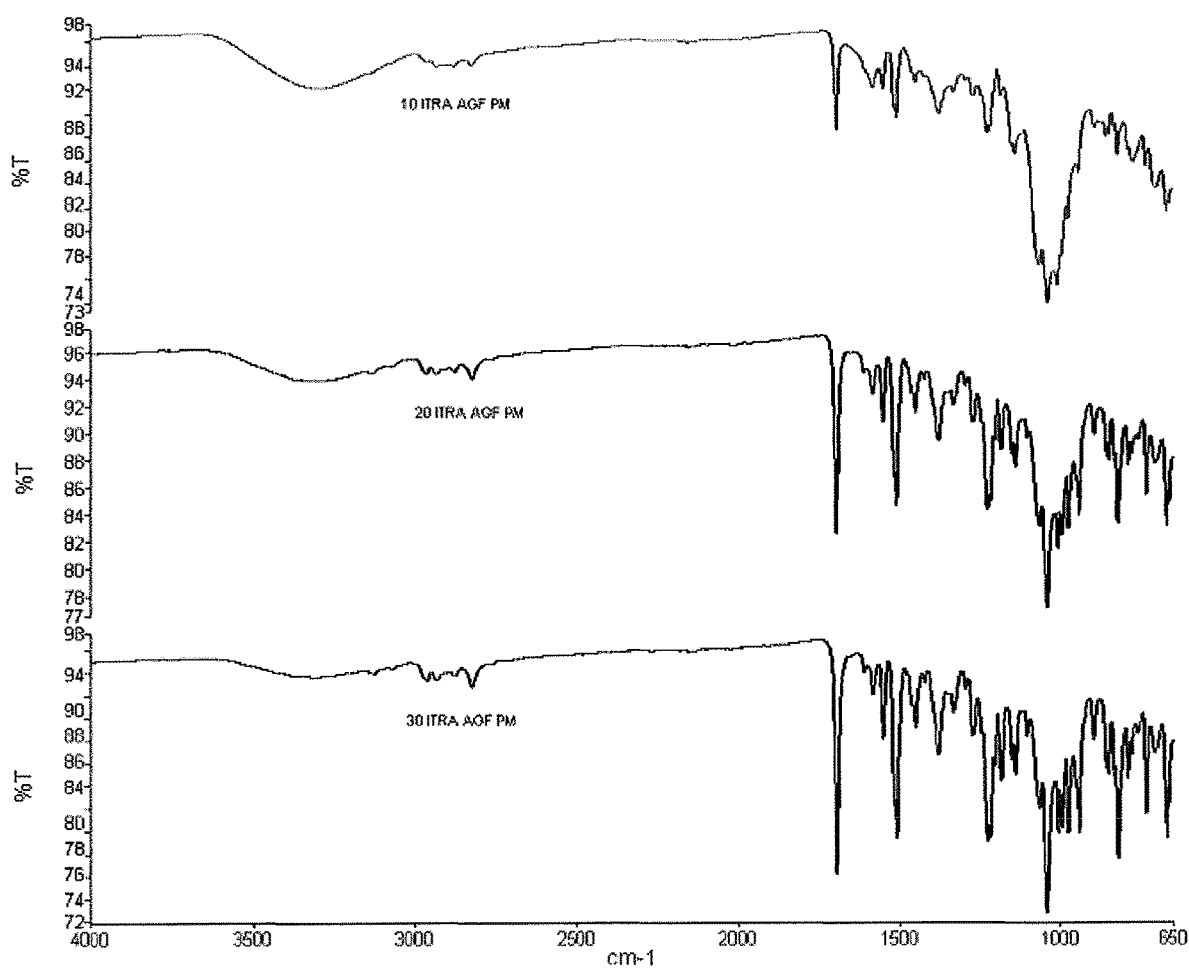
FIG. 23B shows spectra of ITRA AGF PM formulations.
Figure 23C:
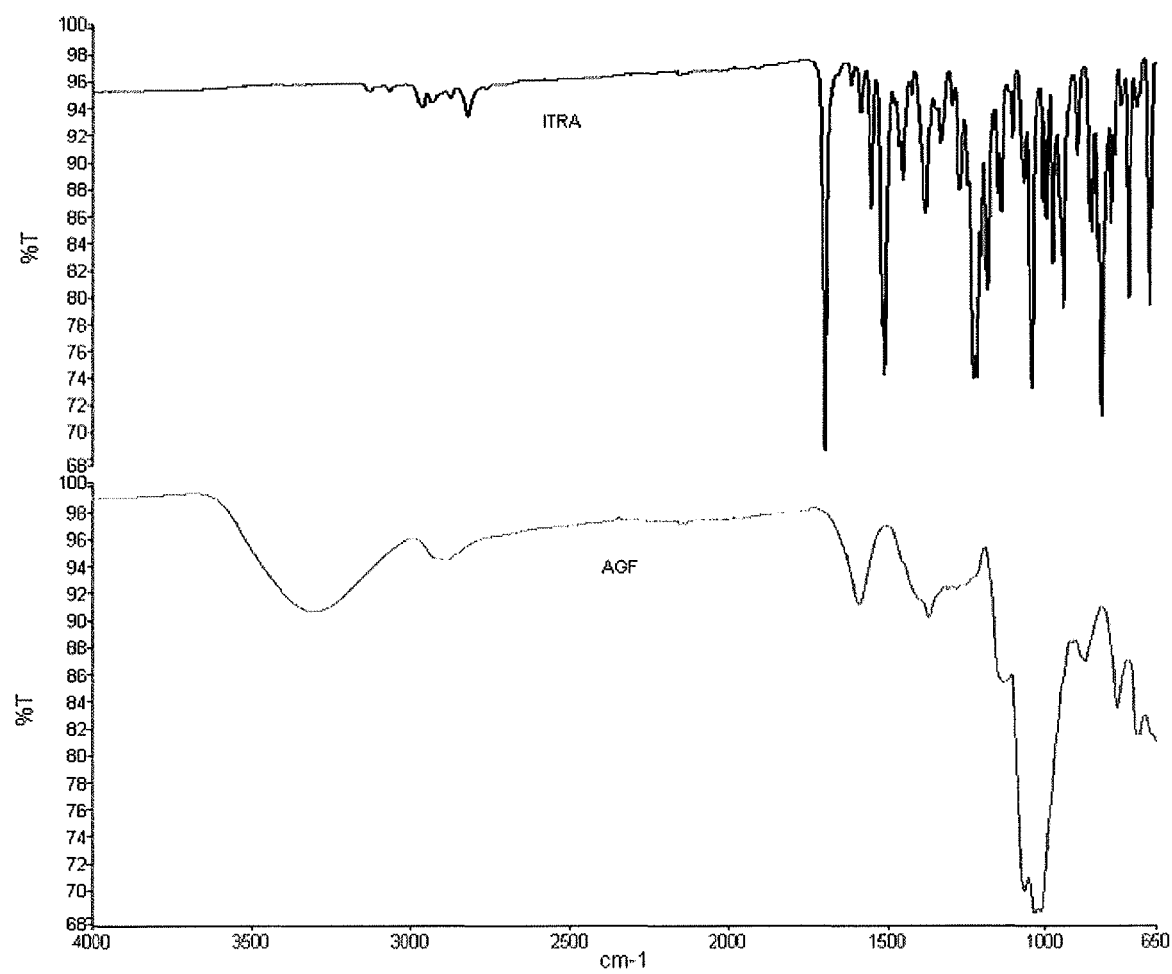
FIG. 23C shows spectra of NEAT AGF polymer and NEAT ITRA.

FTIR was conducted on SDM and PM formulations as described in Example 2. The FTIR spectra of NEAT ITRA showed characteristic peaks at 3382.8 $cm^{-1}$, 3128 $cm^{-1}$, 3069 $cm^{-1}$, 2962 $cm^{-1}$, 1698.03 $cm^{-1}$, 1509.8 $cm^{-1}$, 1609 $cm^{-1}$, 1451.46 $cm^{-1}$ and 1425 $cm^{-1}$ (FIG. 23C). The IR band at 1698.03 $cm^{-1}$ due to C=O stretch did not show any change in shift and intensity in SDM and PM formulations. In fact, the IR spectra of the SDM formulations at all drug loads were found to be equivalent to the sum of the IR spectra of pure AGF polymer and neat ITRA (FIGS. 23A and 23B and Table 9). This indicates that there was no hydrogen bonding between the carbonyl group of ITRA and the OH group of AGF. There is a possibility that stearic hindrances of the surrounding aromatic rings precluded the formation of these hydrogen bonds in ITRA AGF formulations. No covalent bonding between the therapeutic agent and the arabinogalactan is detected in the FTIR data for the SDM formulations (FIG. 23A), or the PM formulations (FIG. 23B).

TABLE 9

Shifts in the major IR bands of ITRA and AGF in ITRA AGF formulations.

| SAMPLE | ITRA 3138 cm$^{-1}$ | ITRA 1698 cm$^{-1}$ (C=O stretch) |
|---|---|---|
| NEAT ITRA | 3138.6 LESS INTENSE | 1698.03 |
| 10% ITRA AGF SDM | NO BAND | 1698.07 |
| 20% ITRA AGF SDM | NO BAND | 1698.48 |
| 30% ITRA AGF SDM | NO BAND | 1698.48 |
| 10% ITRA AGF PM | NO BAND | 1698.47 |
| 20% ITRA AGF PM | 3128.8 LESS INTENSE | 1698.21 |
| 30% ITRA AGF PM | 3128.8 LESS INTENSE | 1698.07 |

Figure 24A:
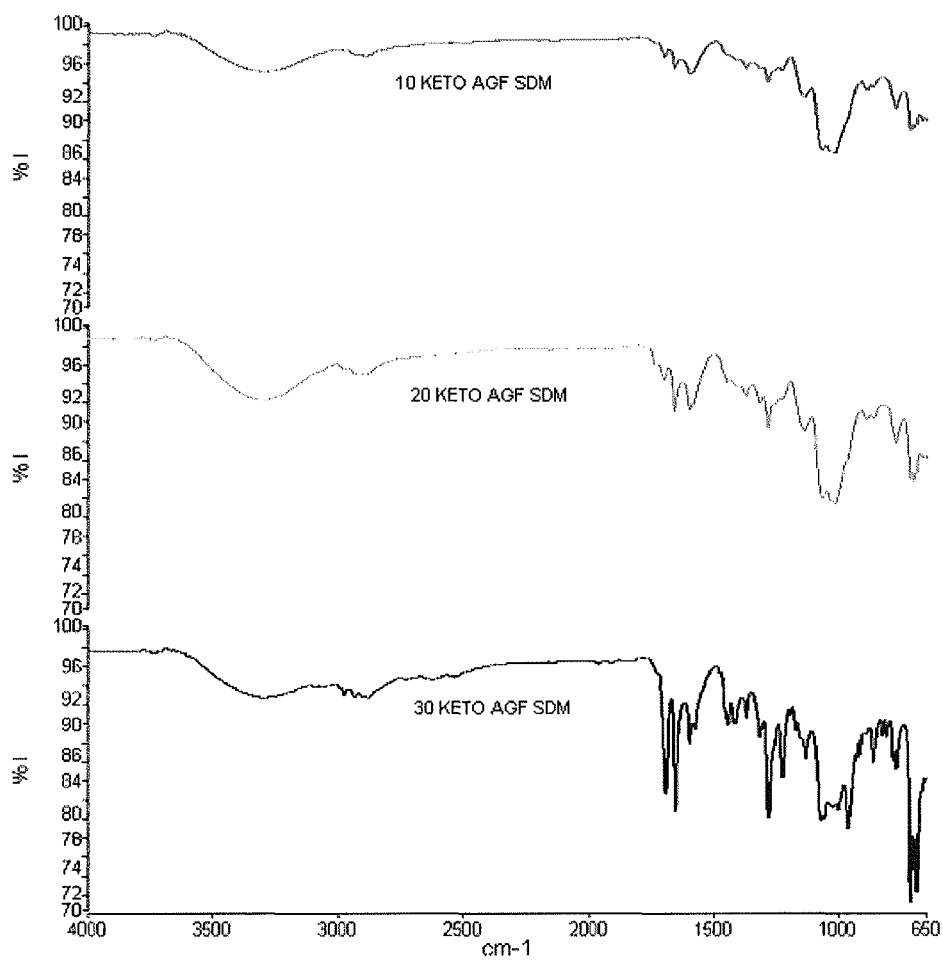
FIG. 24A shows FTIR spectra of KETO AGF SDM formulations.
Figure 24B:
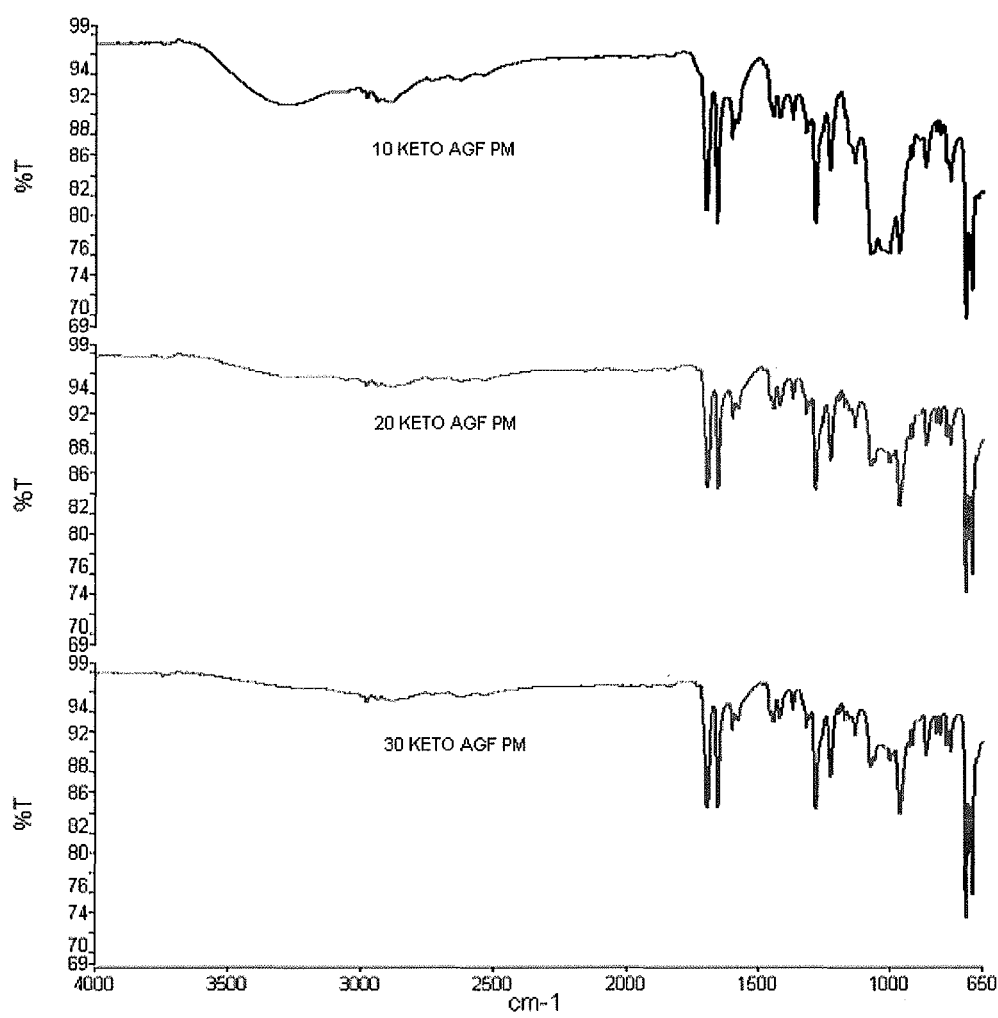
FIG. 24B shows spectra of KETO AGF PM formulations.
Figure 24C:
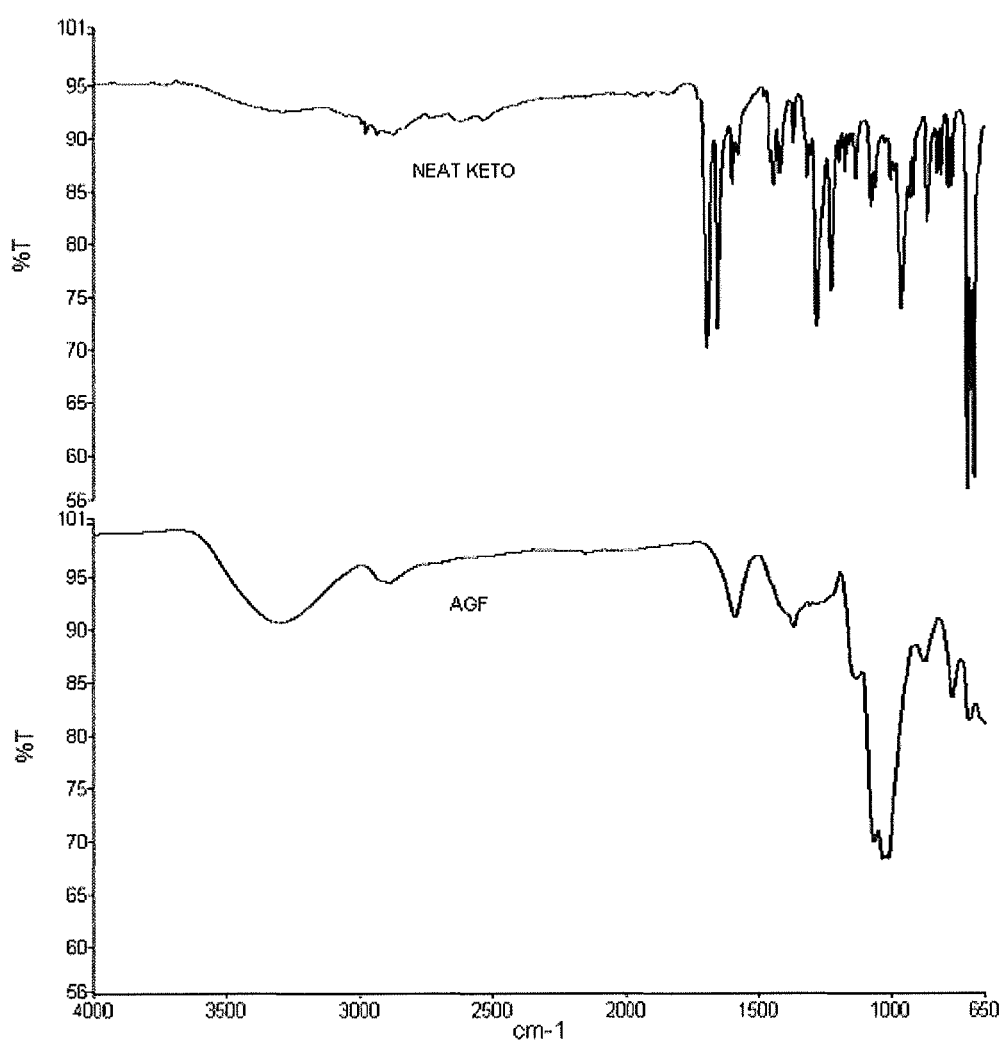
FIG. 24C shows spectra of NEAT AGF polymer and NEAT KETO.

KETO exists in dimer form (Vueba et al., 2006, *Int J Pharm*, Jan. 3, 307(1):56-65; Manna et al., 2007, *J Supercritical Fluids*, 42(3):378-384). The IR spectra of NEAT KETO showed two major IR bands. The first one at about 1694 cm$^{-1}$ was due to carbonyl stretch of dimeric carboxylic acid group and the second at 1654 cm$^{-1}$ was due to carbonyl stretch in the ketonic group (FIG. 24C). Both of these IR bands were shifted to a higher wave number in 10% KETO AGF SDM and 20% KETO AGF SDM and in 10% KETO AGF PM indicating the presence of hydrogen bonded monomeric KETO. In fact the carboxylic acid rather than the ketonic carbonyl group was found to be predominantly involved in the hydrogen bonding. However, in 30% KETO AGF SDM formulations, the shift in these IR bands was minute, indicating the presence of dimeric unbounded KETO in this formulation with weak interactions. Hydrogen bonding was absent in 20% KETO AGF PM and 30% KETO AGF PM. The presence of hydrogen bonding in 10% KETO AGF PM formulation was detected (FIGS. 24A and 24B and Table 10).

TABLE 10

Shift in the major IR band of KETO and AGF in KETO AGF formulations.

| SAMPLE | KETO 1654 cm$^{-1}$ (C=O stretch in ketonic group) | KETO 1694 cm$^{-1}$ (C=O Strech dimeric carboxylic acid) |
|---|---|---|
| KETOPROFEN | 1654.25 | 1694.45 |
| 10% KETO AGF SDM | 1655 | 1698.5 |
| 20% KETO AGF SDM | 1655.54 | 1698.7 |
| 30% KETO AGF SDM | 1655.01 | 1694.7 |
| 10% KETO AGF PM | 1655.12 | 1696.72 |
| 20% KETO AGF PM | 1654.62 | 1694.96 |
| 30% KETO AGF PM | 1654.72 | 1695.11 |

Thus, the carboxylic C=O of KETO and the OH of AGF polymer were found to be involved in hydrogen bonding in KETO AGF SDM.

Thermomechanical Analysis (TMA)

TMA was carried out as described above in Example 4.

Figure 25A:
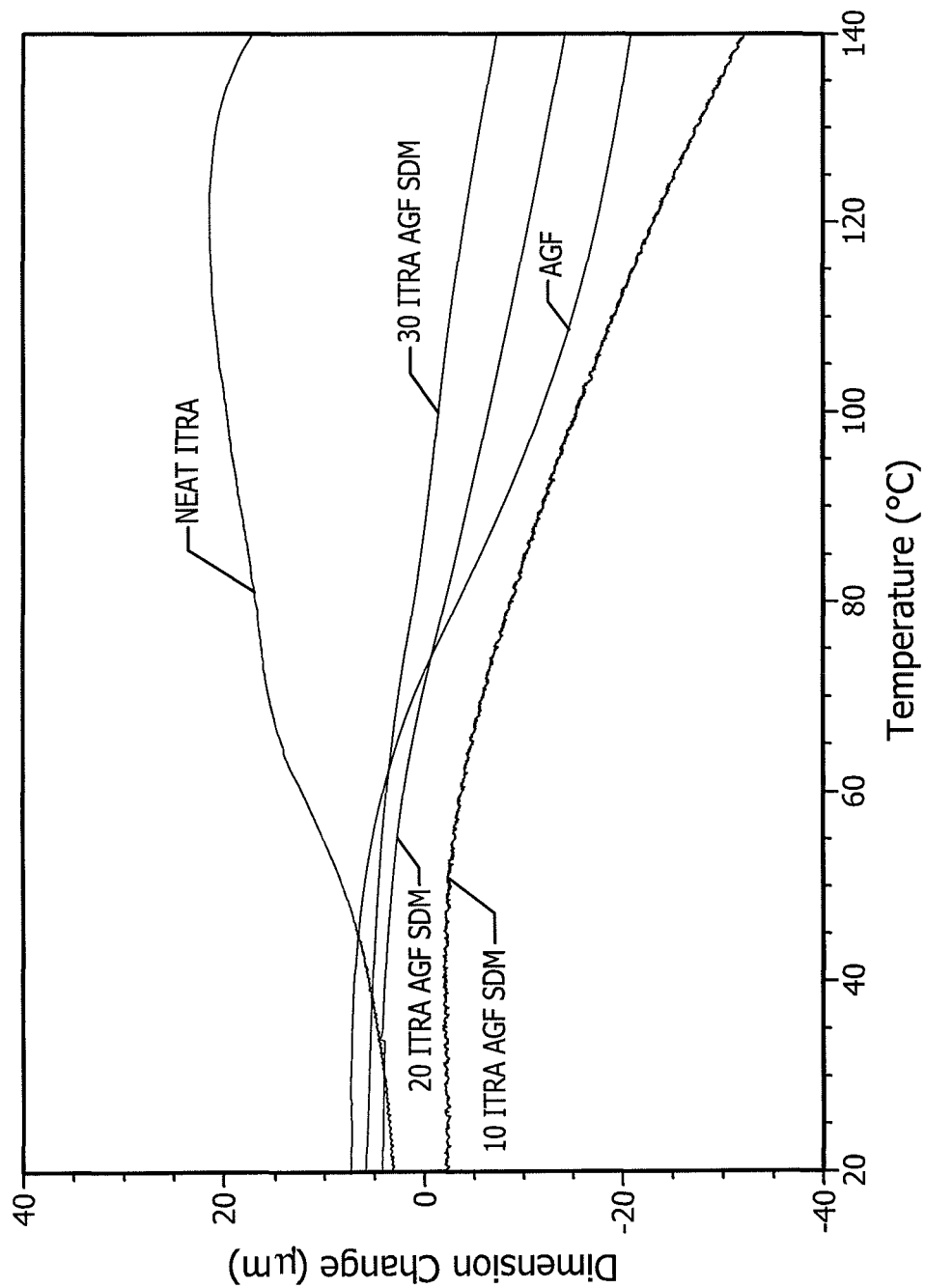
FIG. 25A shows TMA scans of NEAT ITRA, NEAT AGF and ITRA AGF SDM formulations for temperatures up to 140° C. From bottom to top (at the 100° C. mark) are shown: 10% ITRA AGF SDM, NEAT AGF, 20% ITRA AGF SDM, 30% ITRA AGF SDM and NEAT ITRA.
Figure 25B:
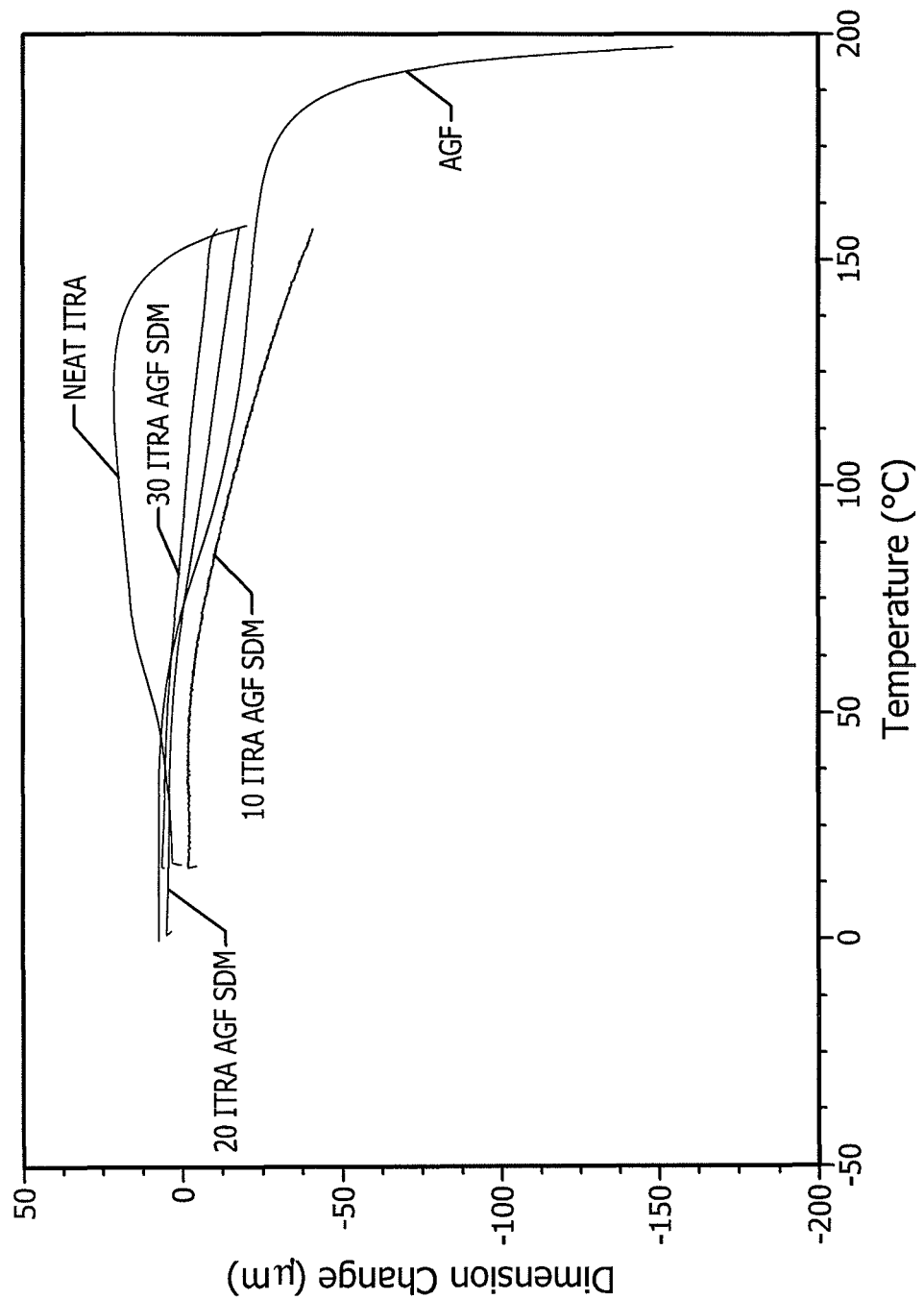
FIG. 25B shows TMA scans of NEAT ITRA, NEAT AGF and ITRA AGF SDM formulations for temperatures up to 200° C. From bottom to top (at the 150° C. mark) are shown: 10% ITRA AGF SDM, NEAT AGF, 20% ITRA AGF SDM, 30% ITRA AGF SDM and NEAT ITRA.

The Tg values of the ITRA AGF SDM formulation obtained from TMA analysis are listed in Table 11 and the TMA scans of ITRA AGF SDM formulations are shown in FIGS. 25A and 25B. 10% ITRA SDM and 20% ITRA SDM have shown single Tg indicating ITRA and AGF were molecularly dispersed for up to 20% DL. The 30% ITRA SDM formulation showed two thermal transitions, the first one was the Tg of the system and the second one could be melting of the drug as 30% ITRA SDM contained scarce amounts of crystalline ITRA as confirmed by DSC, XRPD and SEM. In the presence of AGF polymer the melting depression of ITRA was expected. Thus 30% ITRA AGF SDM formulations consisted of drug polymer dispersion rich domain and crystalline drug domain. Negative deviation to the predicted Tg value from Fox's equation was observed, indicating a lack of hydrogen bonding between the drug and the polymer.

TABLE 11

Comparison of experimental Tg and predicted Tg by Fox's equation.

| Formulation | Experimental Tg (θ C.)/ Thermal transition | Predicted Tg (θ C.) (Fox Eqn) |
|---|---|---|
| NEAT ITRA | 58.23 (Tg) | — |
| 10% ITRA AGF SDM | 67.30 (Tg) | 79.29 |
| 20% ITRA AGF SDM | 64.18 (Tg) | 76.77 |
| 30% ITRA AGF SDM | 72.56 (Tg); 133 (Tm or Tg) | 74.26 |
| AGF | ~82 | — |

Figure 26:
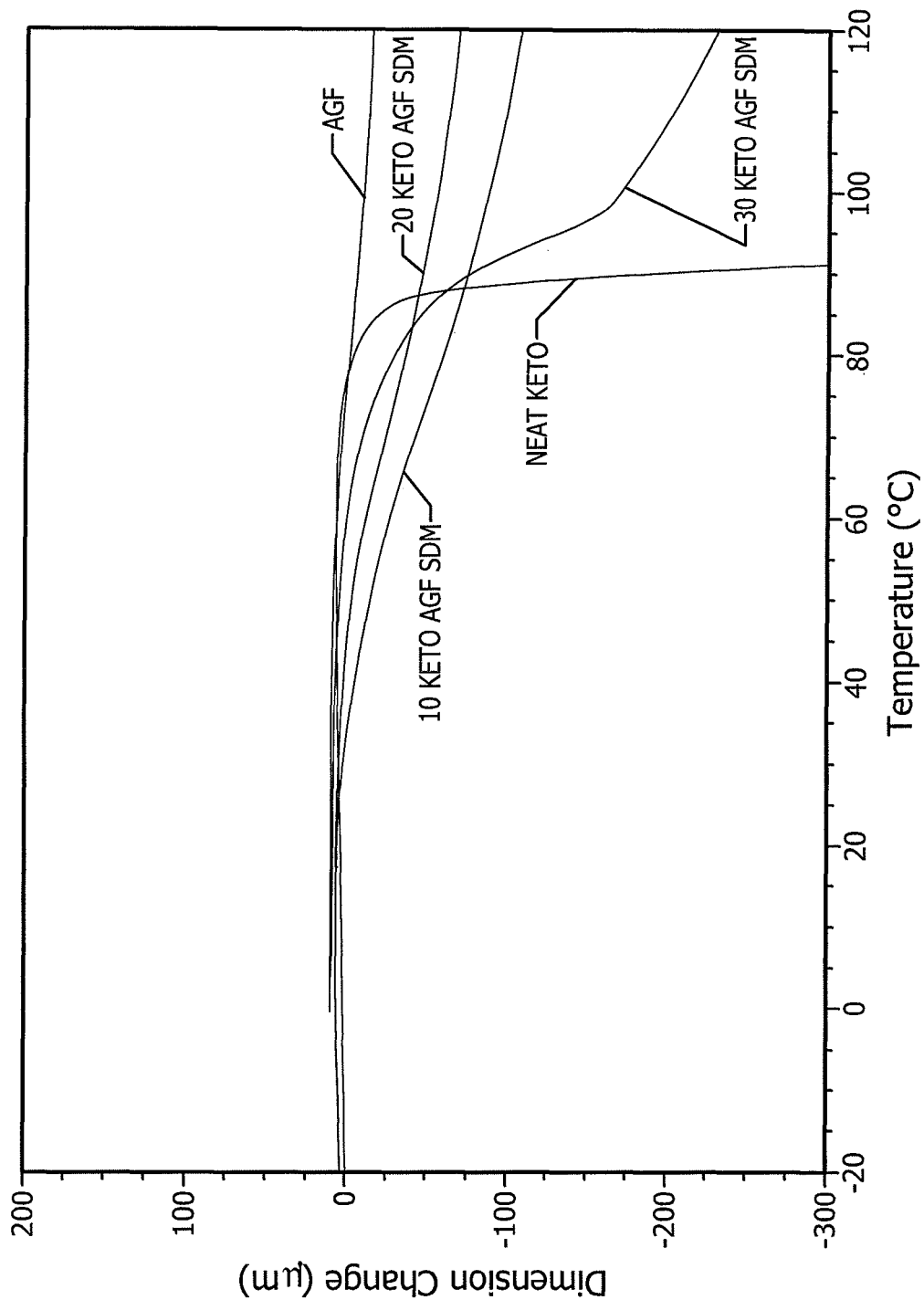
FIG. 26 shows TMA scans of NEAT KETO, NEAT AGF and KETO AGF SDM formulations. From bottom to top (sweeping from left to right after the 90° C. mark) are shown: NEAT KETO, 30% KETO AGF SDM, 10% KETO AGF SDM, 20% KETO AGF SDM and NEAT AGF.

The experimental Tg values for KETO AGF SDM formulations, compared with theoretical Tg values, are summarized in Table 12. KETO and AGF were completely miscible for up to 20% DL as is obvious from the single Tg for 10% KETO AGF SDM and 20% KETO AGF SDM formulation (FIG. 26). However, the presence of crystalline KETO in 30% KETO AGF SDM formulation resulted in a melting transition at 71.91° C. Positive deviation in the experimental Tg value compared to the predicted value by the Fox equation was observed, which suggests stronger KETO AGF interactions. Thus, the formation of multiple hydrogen bonds was associated with a positive deviation to the theoretical Tg by the Fox Equation in the current KETO AGF SDM system.

TABLE 12

Experimental and theoretical Tg of KETO AGF SDM formulations.

| Formulation | Experimental Tg/Thermal Transition (θ C.) | Predicted Tg (θ C.) (Fox Eqn) |
|---|---|---|
| NEAT KETO | -3.15 (Di Martino et al., 2004) | — |
| 10% KETO AGF SDM | 77.11 (Tg) | 71.01 |
| 20% KETO AGF SDM | 75.33 (Tg) | 61.98 |
| 30% KETO AGF SDM | 71.91 (Tg); 91.44 (Tm) | 55.21 |
| AGF | ~82 (Tg) | — |

In Vitro Basket Dissolution-Methods

In vitro basket dissolution was carried out on SDM and PM formulations as described in Example 3. Each sample of ITRA AGF SDM contained an amount equivalent to 25 mg of ITRA to maintain the non sink conditions. ITRA was analyzed using an Agilent/HP 8453 UV-Vis spectrophotometer (λmax=257 nm).

For KETO in vitro dissolution, the changes made to the protocol were that the volume of the dissolution media was 450 ml, and that each sample contained the equivalent of 50 mg of KETO to maintain non sink conditions. UV analysis was conducted at λmax=260 nm.

The degree of similarity between the dissolution profiles was calculated using the following equation from Moore and Flanner, 1996, *Pharm. Tech.* 20:64-74, and using data points up to 85% drug release (Shah et al., 1998, *Pharm. Res.* 15:889-896):

$$f_2 = 50 \log\left\{100\left[1 + \left(\frac{1}{n}\right)\sum (R_t - T_t)^2\right]^{-0.5}\right\}$$

$R_t$-reference assay at time point t
$T_t$-test assay at time point t

Two dissolution profiles would be deemed similar if the average difference between the reference and the test assay at the same time point were less than 10%. The similarity factor value would then not be less than 50%.

Statistical Analysis

Minitab 16.0 (Minitab Inc.) software was used for statistical analyses. The statistical analysis of solubility and dissolution data was carried out using ANOVA (one way analysis of variance) with pair wise multiple comparison procedures. Differences were considered significant when p<0.05. Tukey's test for multiple comparisons was used to calculate the significance differences among the different dissolution profiles.

In Vitro Basket Dissolution-Results

Figure 27:
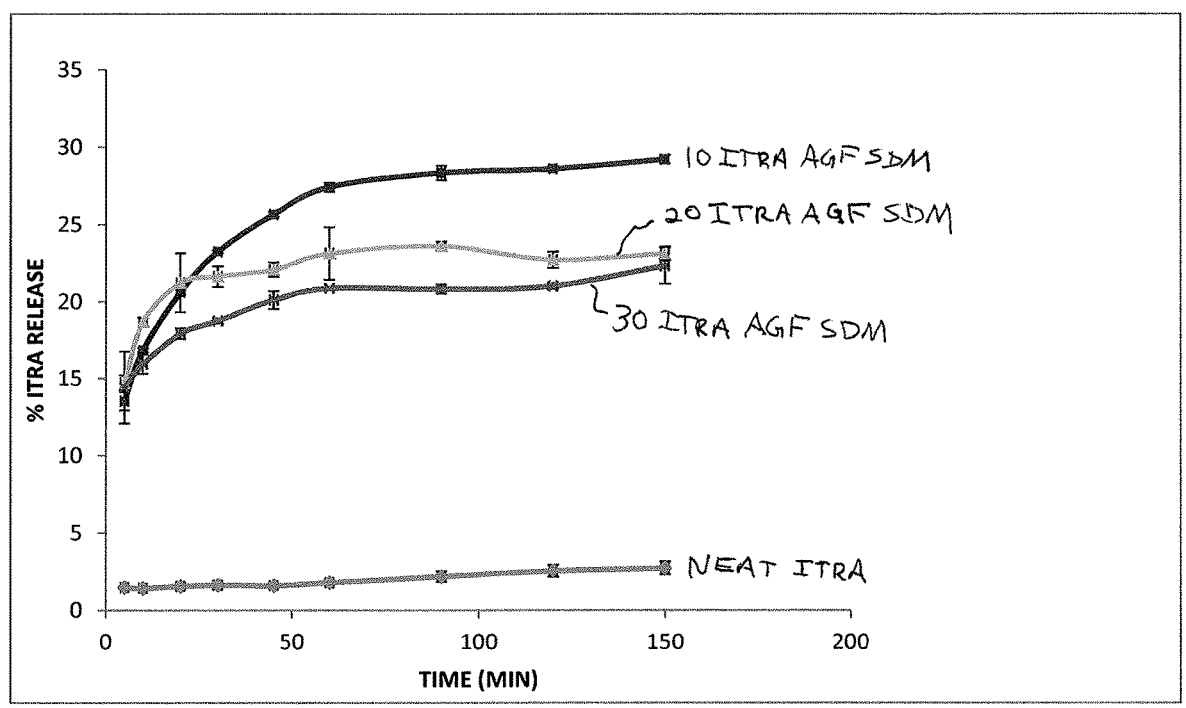
FIG. 27 shows the mean dissolution profiles of ITRA AGF formulations in 0.1N HCl.

FIG. 27 shows the mean dissolution profiles of ITRA SDM formulations. The dissolution of PM was not conducted owing to the presence of crystalline ITRA in these formulations. As can be seen in the figure, the SDM formulations showed faster initial dissolution compared to neat ITRA. % relative standard deviation (RSD) values were within 10% except % RSD values of 16% was observed for initial time point for dissolution profile of 30% ITRA SDM.

The values of similarity factor between the dissolution profiles for ITRA SDM expressed in % are listed in Table 13. The similarity factor value between 50-100% indicates that the dissolution profiles are similar. The dissolution profiles of ITRA AGF SDM (all drug loads) were not similar to that of neat ITRA. However, the dissolution profiles of the SDM formulations were similar to each other irrespective of the drug load.

TABLE 13

Similarity factors (f2) for dissolution profiles ITRA AGF SDM

|  | Neat ITRA | 20 SDM | 30 SDM |
|---|---|---|---|
| 10% SDM | 41.680 | 78.237 | 72.628 |
| 20% SDM | 46.515 | — | 89.232 |
| 30% SDM | 48.776 | — | — |

The results of the statistical analysis of the dissolution data showed a significant increase in the dissolution with SDM formulations compared to neat ITRA. The 10% ITRA SDM dissolution profile was statistically significantly higher that of the 30% ITRA SDM dissolution profile. No significant differences were found in the dissolution profile of the 10% SDM and the dissolution profile of the 20% SDM, or between the dissolution profiles of the 20% SDM and the 30% SDM. The dissolution enhancement for SDM formulations was in the order of 10% DL>20% DL>30% DL. The significant dissolution enhancement in SDM formulations can be attributed to the presence of amorphous ITRA.

Figure 28:
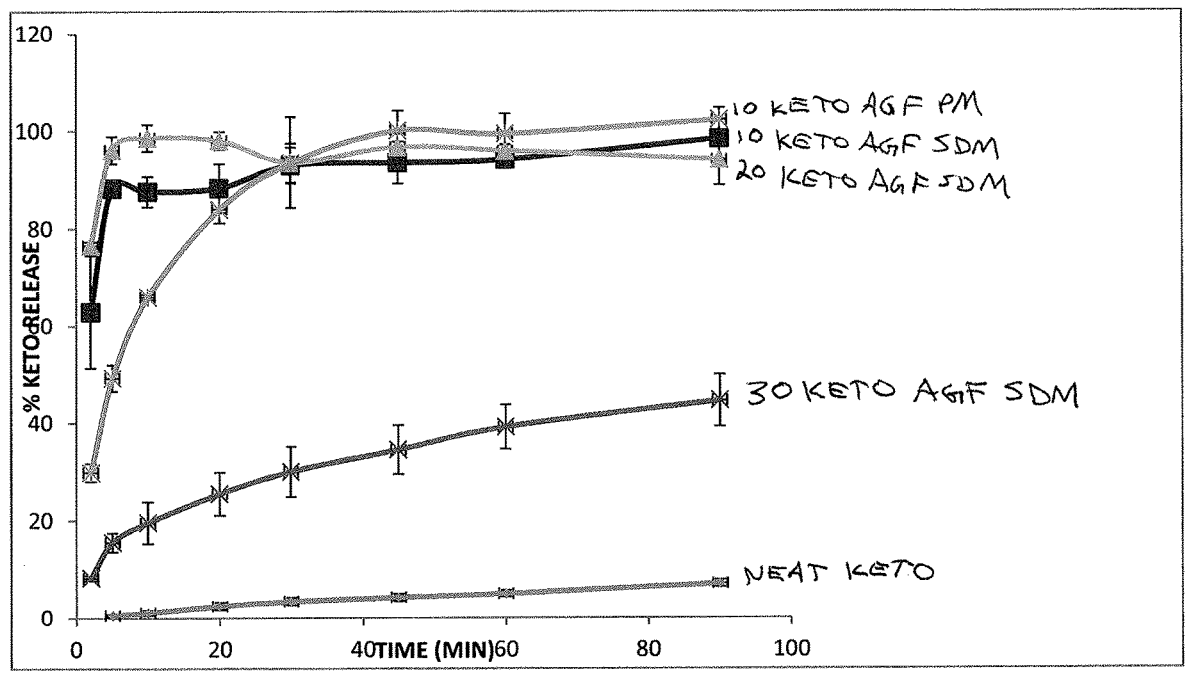
FIG. 28 shows the mean dissolution profiles of KETO AGF formulations in 0.1N HCl.

FIG. 28 shows the mean dissolution profiles of KETO SDM formulations. Statistical analysis of the dissolution data showed a significantly greater dissolution rate for KETO formulations of 10% KETO SDM, 20% KETO SDM and 10% KETO PM, compared to 30% KETO SDM. FIG. 27 also shows that the initial % KETO release was higher for 10% KETO SDM and 20% KETO SDM than for 10% KETO PM. Surprisingly, 20% KETO SDM showed higher initial % KETO release than 10% KETO SDM.

Figure 29:
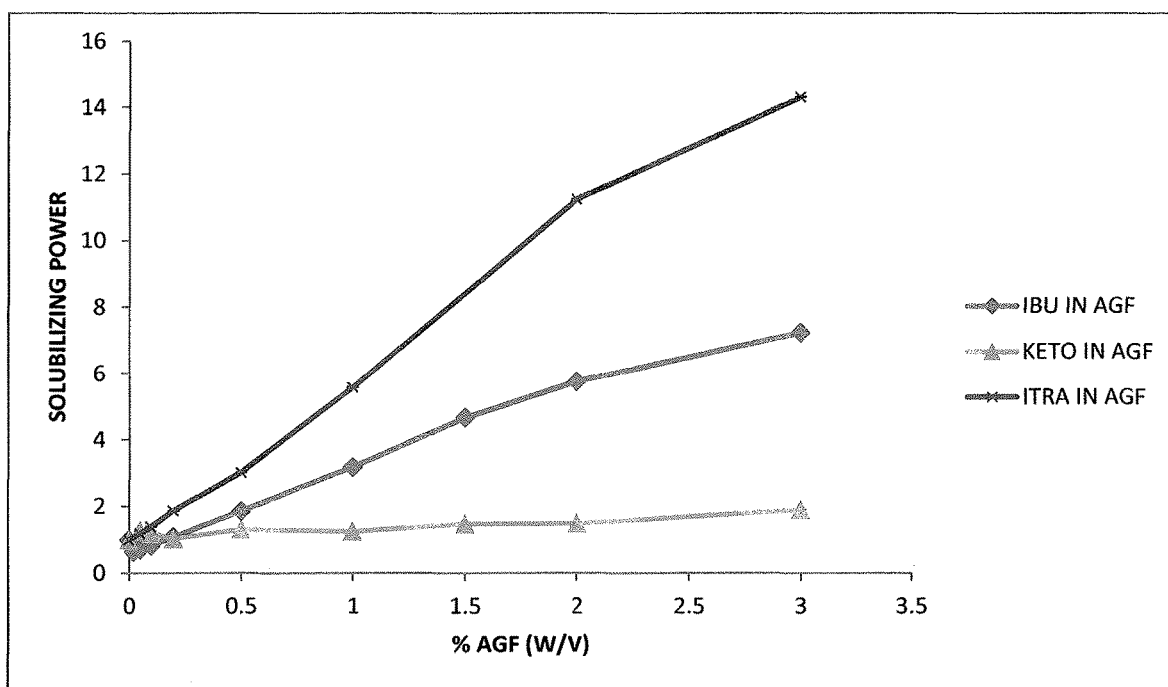
FIG. 29 shows the solubilizing power of AGF polymer for different drugs in 0.1N HCl.

Example 7. Comparison of Solubility Enhancement Potential of AGF for IBU, KETO and ITRA The solubilizing power of AGF polymer for IBU, KETO and ITRA is shown in FIG. 29. Solubility enhancement due to AGF polymer was in the following order: ITRA>IBU>KETO. Statistical analysis of solubilizing power data and the equilibrium solubility data for IBU, ITRA, KETO did not show significant differences in solubility in the presence of AGF polymer at the respective concentrations. In the presence of AGF an about 1.2- to 14.3-fold increase in solubility was observed for various crystalline drugs at 1:10 and 1:20 mass ratio (without any treatment) Table 14.

TABLE 14

Fold increase in solubility in the presence of AGF polymer

|  | Physical mix | Planetary mill | Rotary ball mill |
|---|---|---|---|
| Diazepam:AG (1:10) | 1.2 | 2.4 | 48.2 |
| Indomethacin:AG | 1.1 | 9.9 | 39.7 |
| Mezapam | 4.9 | 19.1 | 140.6 |
| Clozapine | 4.4 | 20.5 | 107.9 |
| Nifedipine | — | 6.9 | |
| Dihydroquercitin (1:10) | | | 5.9 |
| DQ (1:20) | 3 | — | 38 |
| DQ (1:10) | — | — | 10 |
| Quercitin | | 11.6 | |
| Ibuprofen | 1.2 | | 28.4 |
| Beta-Carotene (1:40) | — | 2000 | — |
| Warfarin (1:40) | — | 5.3 | — |
| Albendazol (1:10) | — | 8.0 | 58.0 |
| Carbenazim (1:10) | — | — | 16.2 |
| Simvastatin (1:10) | — | 36.7 | — |
| Azaleptin (1:10) | 12.4 | 20.5 | — |
| Azaleptin (1:20) | 14.3 | 38.8 | — |
| Mezapam (1:10) | 6.9 | 19.1 | — |
| Mezapam (1:20) | 10.8 | 46.8 | — |
| Sibazon (1:10) | 1.7 | 2.4 | — |
| Sibazon (1:10) | 2 | 3 | — |
| Indometacin (1:10) | 1.2 | 9.9 | — |
| Indometacin (1:20) | 1.7 | 16.6 | — |

Figure 30A:
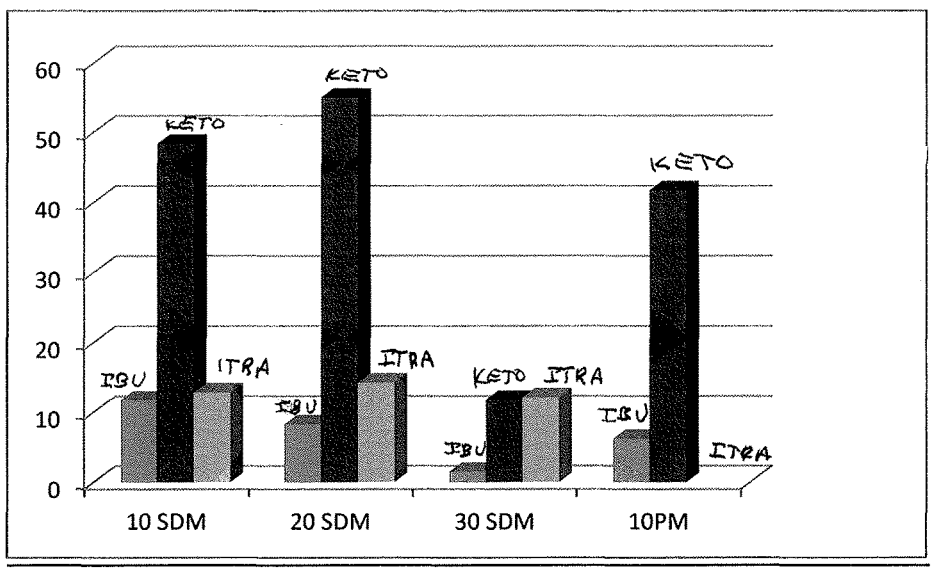
FIG. 30A shows the fold increase in dissolution of SDM and PM formulations of 10%, 20% or 30% IBU, KETO or ITRA with respect to the corresponding neat drug at % DR 15 min (% drug release at 15 minutes).
Figure 30B:
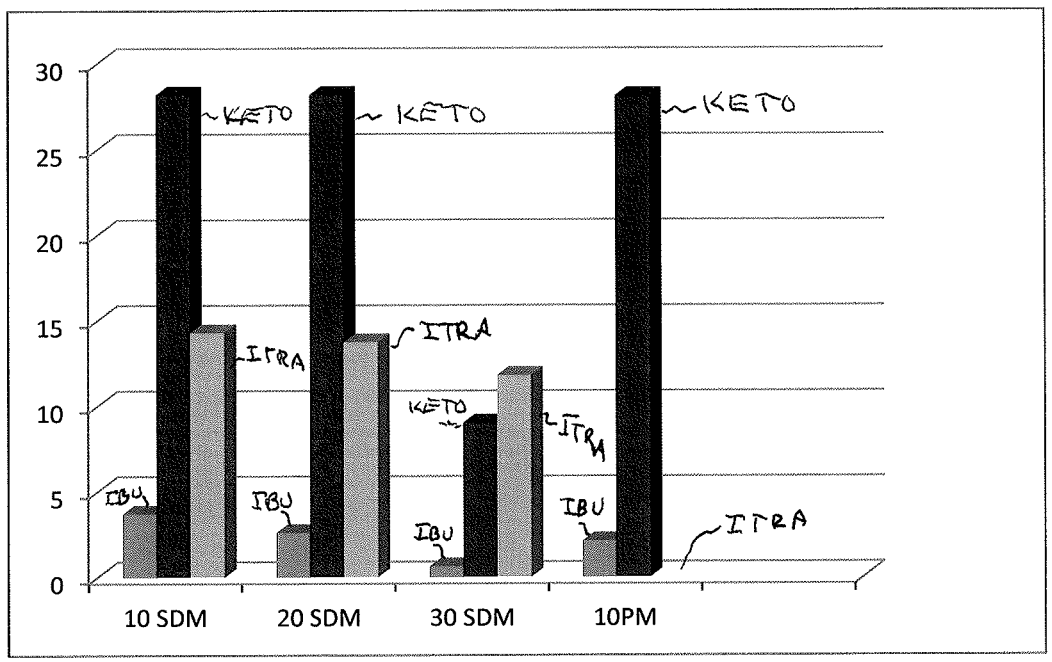
FIG. 30B shows the fold increase in dissolution of SDM and PM formulations of 10%, 20% or 30% IBU, KETO or ITRA with respect to the corresponding neat drug at % DR 30 min (% drug release at 30 minutes).
Figure 30C:
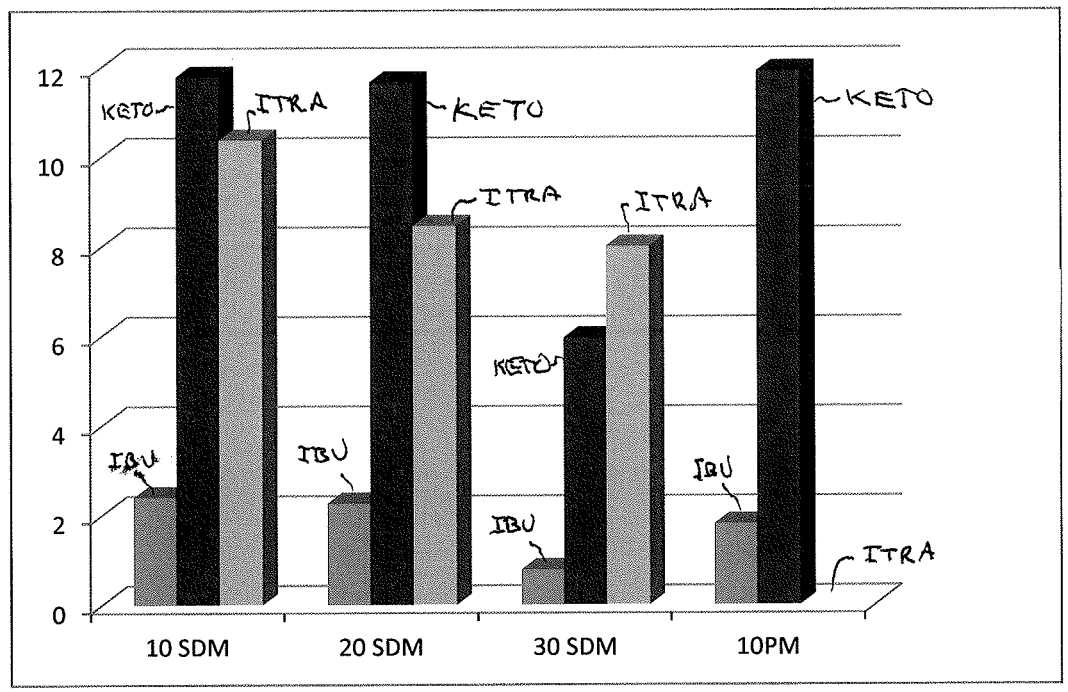
FIG. 30C shows the fold increase in dissolution of SDM and PM formulations of 10%, 20% or 30% IBU, KETO or ITRA with respect to the corresponding neat drug at % DR 120 min (% drug release at 120 minutes).

The extent of dissolution enhancement for IBU, ITRA and KETO in terms of % DR 15 min, % DR 30 min and % DR 120 min are shown in FIG. 30A-C. See Tables 15, 16 and 17. The observed dissolution enhancement was in the following order: KETO>ITRA>IBU at 15 min, 30 min and at 120 min.

TABLE 15

DR10 min (% drug release at 15 minutes) from AGF formulations.

|  | IBU | KETO | ITRA |
|---|---|---|---|
| NEAT DRUG | 8 | 1.8 | 1.4 |
| 10% SDM | 94 (11.75) | 87 (48.33) | 18 (12.87) |
| 20% SDM | 66 (8.25) | 99 (55) | 20 (14.28) |
| 30% SDM | 12 (1.5) | 23 (12.77) | 17 (12.14) |
| 10% PM | 52 (6.5) | 75 (41.66) | |

TABLE 16

DR30 min (% drug release at 30 minutes) from AGF formulations.

|  | IBU | KETO | ITRA |
|---|---|---|---|
| NEAT DRUG | 27 | 3.3 | 1.6 |
| 10% SDM | 100 (3.7) | 93 (28.18) | 23 (14.3) |
| 20% SDM | 71 (2.6) | 93 (28.18) | 22 (13.75) |
| 30% SDM | 17 (0.62) | 30 (9) | 19 (11.8) |
| 10% PM | 57 (2.1) | 93 (28.1) |  |

TABLE 17

DR120 min (% drug release at 120 minutes) from AGF formulations.

|  | IBU | KETO | ITRA |
|---|---|---|---|
| NEAT DRUG | 41 | 8.4 | 2.6 |
| 10% SDM | 100 (2.4) | 99 (11.78) | 27 (10.38) |
| 20% SDM | 93 (2.26) | 98 (11.66) | 23 (8.46) |
| 30% SDM | 32 (0.78) | 50 (5.95) | 21 (8) |
| 10% PM | 74 (1.8) | 100 (11.90) |  |

Although the solubilizing power was in the following order: ITRA>IBU>KETO, the observed dissolution enhancement was in the following order of KETO>ITRA>IBU. This was unexpected because when comparing IBU AGF SDM, ITRA AGF SDM and KETO AGF SDM, one would expect the dissolution enhancement to be in the same order as the solubilizing power. However, solubilization and dissolution enhancement are two different phenomena. Solubilization is only one of the factors that governs dissolution. The amorphous state of the respective drugs led to the dissolution enhancement in these amorphous solid dispersions. Additionally, hydrogen bonding, solution state interaction and AGF's ability to maintain supersaturation upon dissolution all varied for these various systems and therefore the observed dissolution enhancement was in a different order.

Example 8. Evaluation of Drug Crystallization Inhibition Potential of AGF Polymer in DRUG AGF Solid Dispersions (SDs)

Ritonavir (RITO)

Figure 31A:
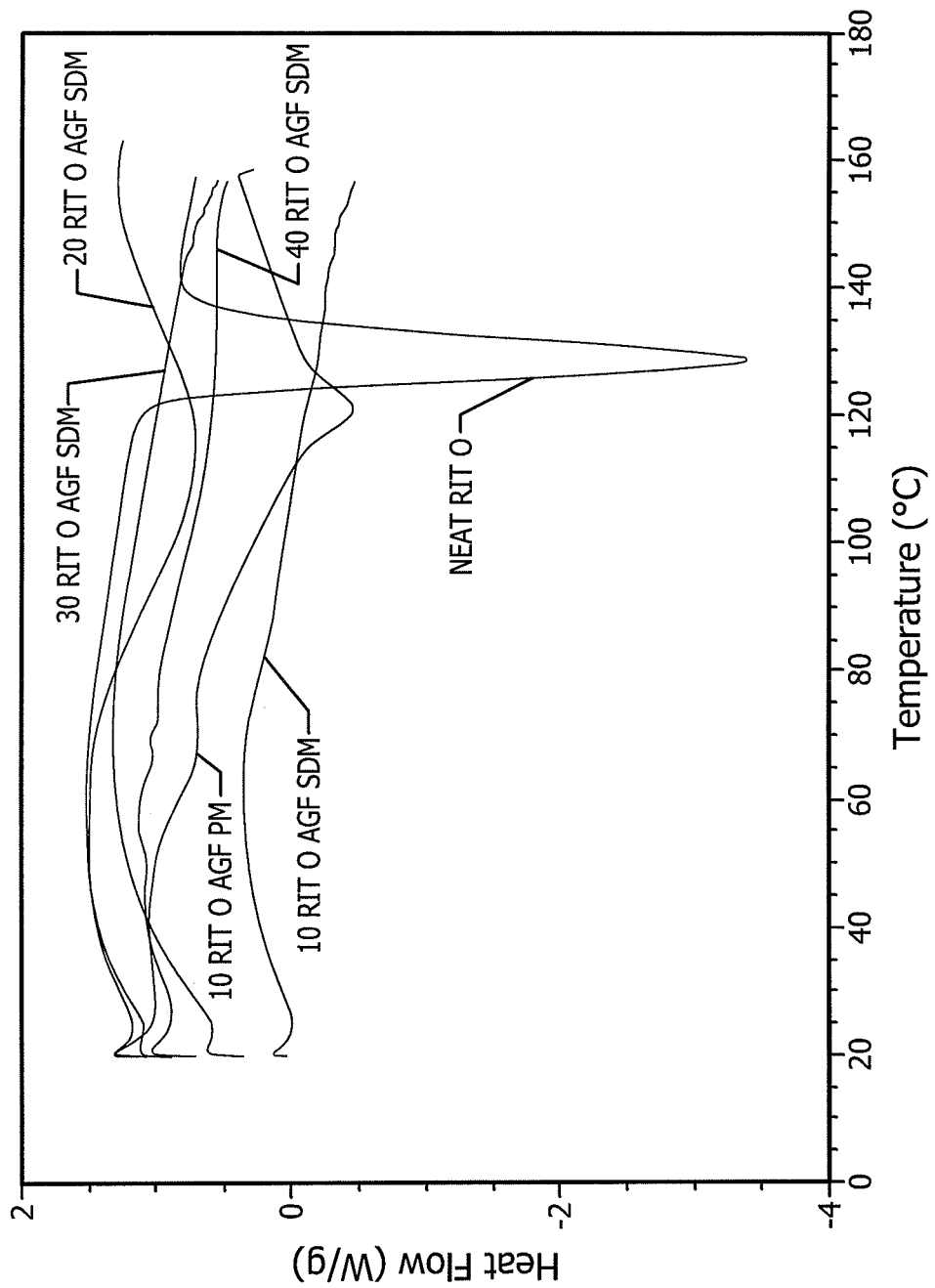
FIG. 31A shows the DSC thermographs of RITO AGF PM and RITO AGF SDM. The melting endotherm is at 128.68° C. From bottom to top (at the 90° C. mark) are shown: 10% RITO AGF SDM, 10% RITO AGF PM, 40% RITO AGF SDM, 20% RITO AGF SDM, 30% RITO AGF SDM and NEAT RITO.
Figure 31B:
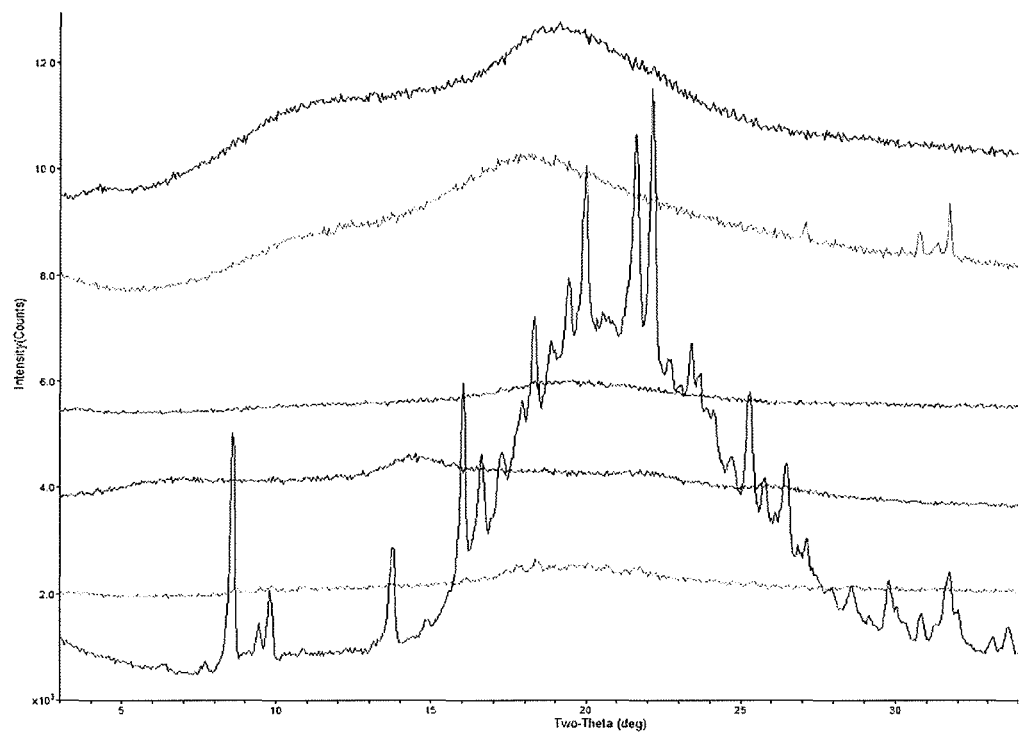
FIG. 31B shows XRPDs of RITO AGF SDM formulations. From bottom to top at the 12 Two-Theta mark are shown: NEAT RITO, 40% RITO AGF SDM, 30% RITO AGF SDM, 20% RITO AGF SDM, 10% RITO AGF SDM, NEAT AGF (crystallinity peaks at 2θ of 8.59°, 13.74°, 16°, 19.4°, 19.9°, 21.6°, 22.1° and 25.2°).

DSC studies showed that full amorphicity of RITO was observed for up to 40% drug load as is evident from the absence of RITO melting at 128.68 θC. Broadening of the endotherm for 10% RITO PM was indicative of a little disorder (FIG. 31A). The sharp, highly intense diffraction peaks of RITO crystallinity were either absent, or if present were of less intensity, in RITO AGF SDM formulations (FIG. 31B).

Figure 31C:
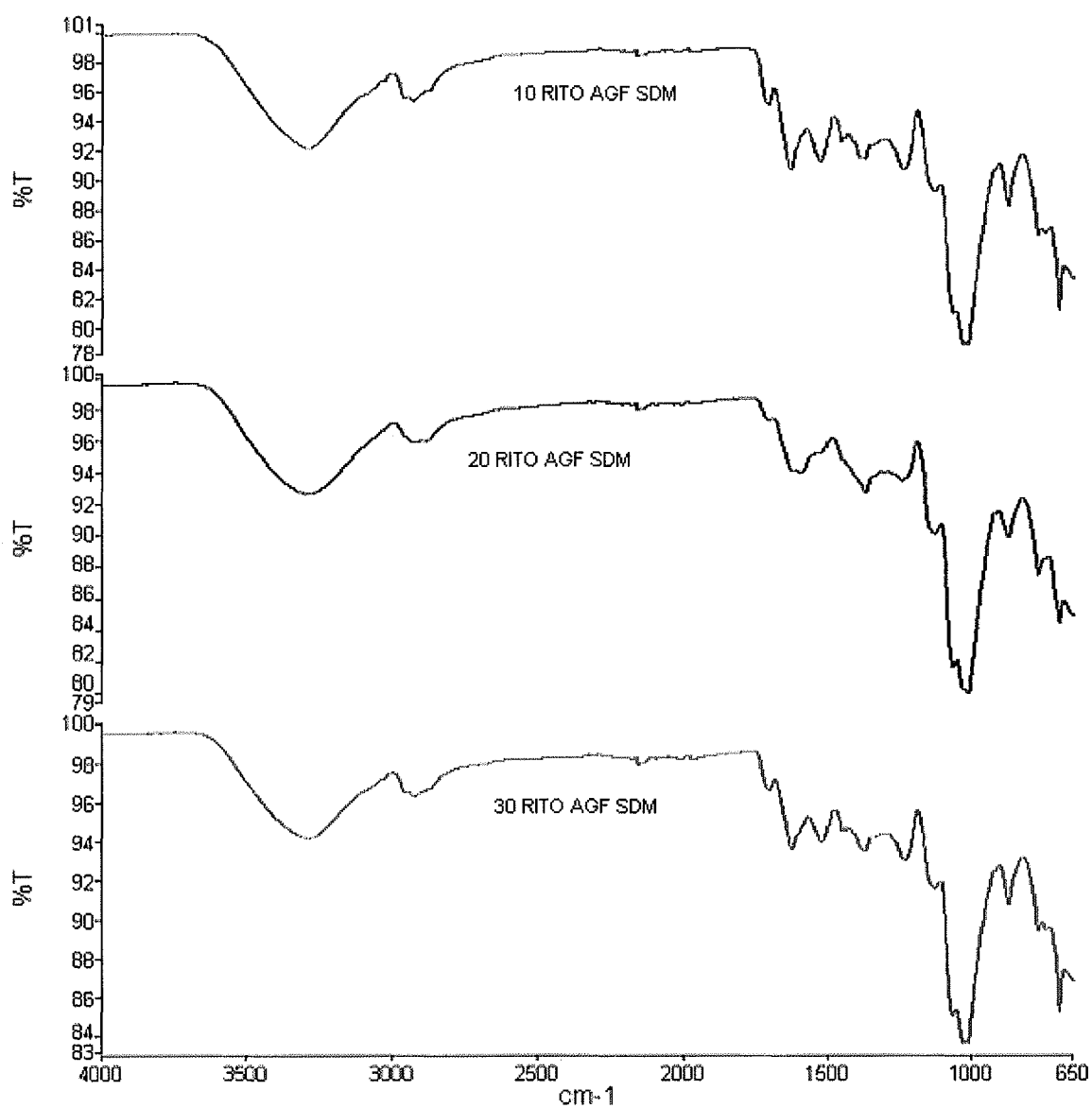
FIG. 31C shows FTIR spectra of 10% RITO AGF SDM, 20% RITO AGF SDM and 30% RITO AGF SDM.
Figure 31D:
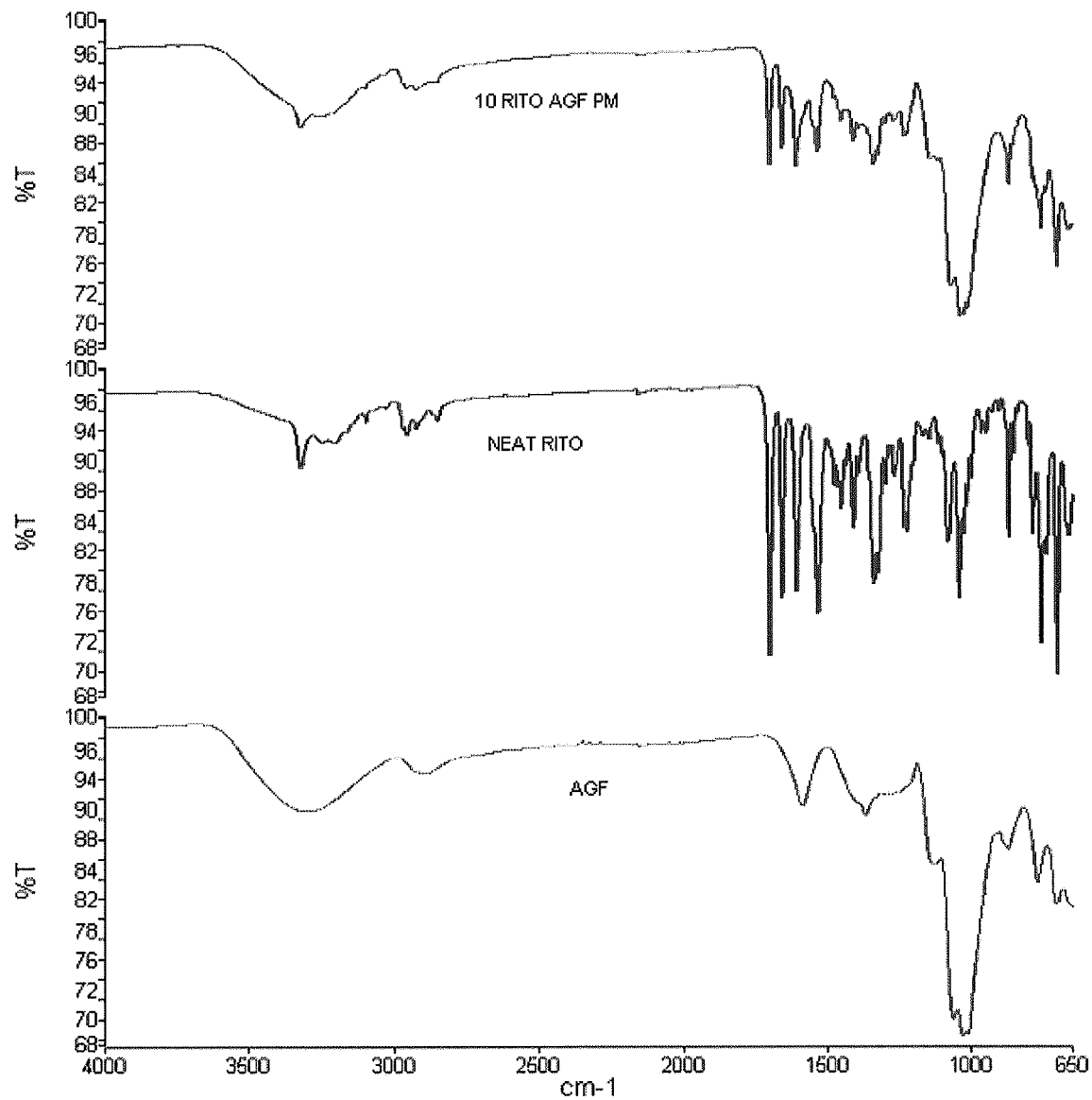
FIG. 31D shows FTIR spectra of NEAT RITO, NEAT AGF and 10 RITO AGF SDM.

Hydrogen bonding was observed between the C═O (ester linkage) of RITO and the OH group of AGF polymer in SDM formulations at all DL as well as in 10% PM formulation. This was evidenced by the reduced intensity and the shift in IR band at 1702 cm$^{-1}$ (ester linkage) and the red shift in the IR band at 3308 cm$^{-1}$ (OH) of AGF. The red shift of the IR band of RITO at 2958 cm$^{-1}$ was indicative of disruption of the hydrogen bonding within the RITO molecule (FIG. 31C, FIG. 31D). Thus, molecular dispersion of RITO in AGF SDM was found to be associated with hydrogen bonding.

Tioconazole (TIOCO)

Figure 32A:
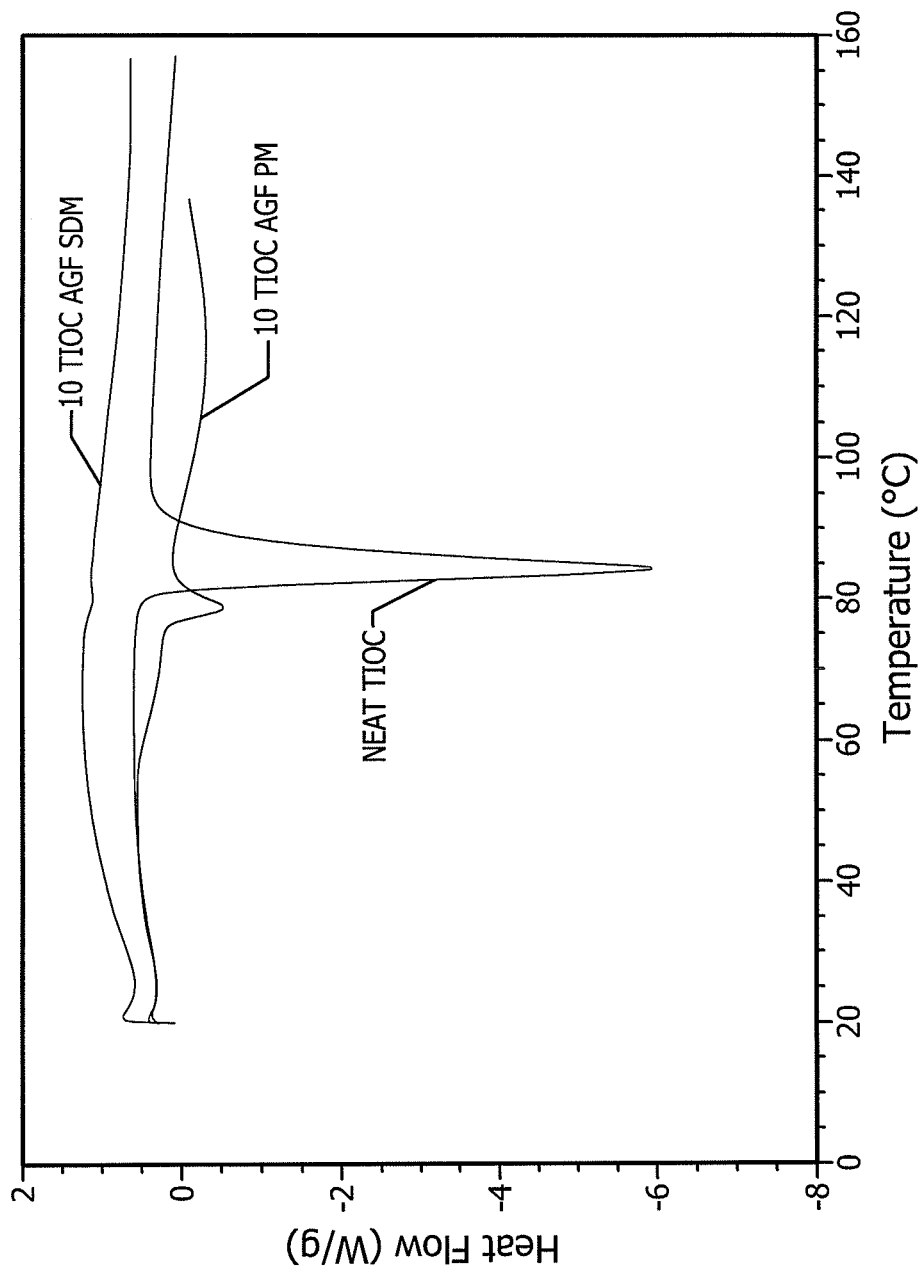
FIG. 32A shows the DSC thermographs of tioconazole (TIOCO) AGF PM and TIOCO AGF SDM. The melting endothers is at 84.24° C. From bottom to top (at the 100° C. mark) are shown: 10% TIOCO AGF PM, NEAT TIOCO and 10% TIOCO AGF SDM.
Figure 32B:
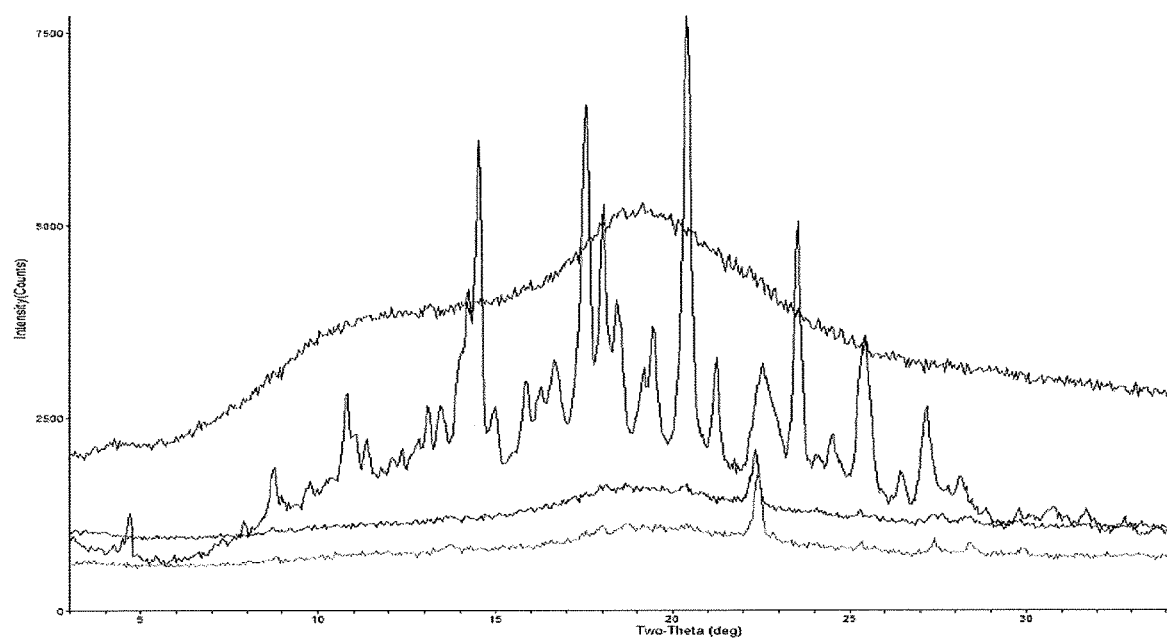
FIG. 32B shows the XRPD of TIOCO AGF SDM formulations. From bottom to top at the 10 Two-Theta mark are shown: 10% TIOCO AGF PM, 10% TIOCO AGF SDM, NEAT TIOCO, NEAT AGF (crystallinity peaks at 2θ of 10.8°, 14.50°, 17.54°, 20.40°, 23.53°, 25.44°, 27.11°.

FIG. 32A shows that a melting endotherm was completely absent in 10% TIOCO SDM formulation. Some XRPD peaks indicating TIOCO crystallinity disappeared whereas the remaining peaks (22.34; 27.3) showed shifts confirming almost amorphous TIOCO in 10% SDM (FIG. 32B). Little disorder was observed in PM formulations, as is shown by DSC in FIG. 32A and by XRPD in FIG. 32B.

Figure 32C:
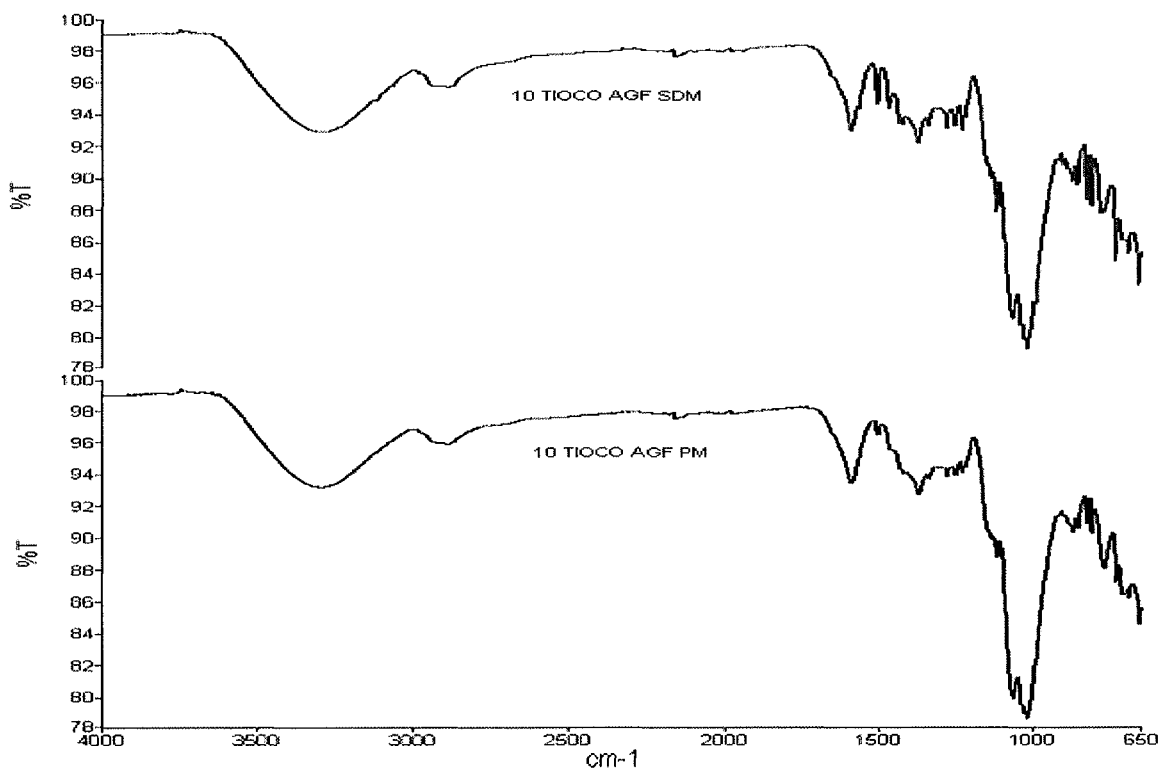
FIG. 32C shows FTIR spectra of 10% TIOCO AGF PM AND 10% TIOCO AGF SDM.
Figure 32D:
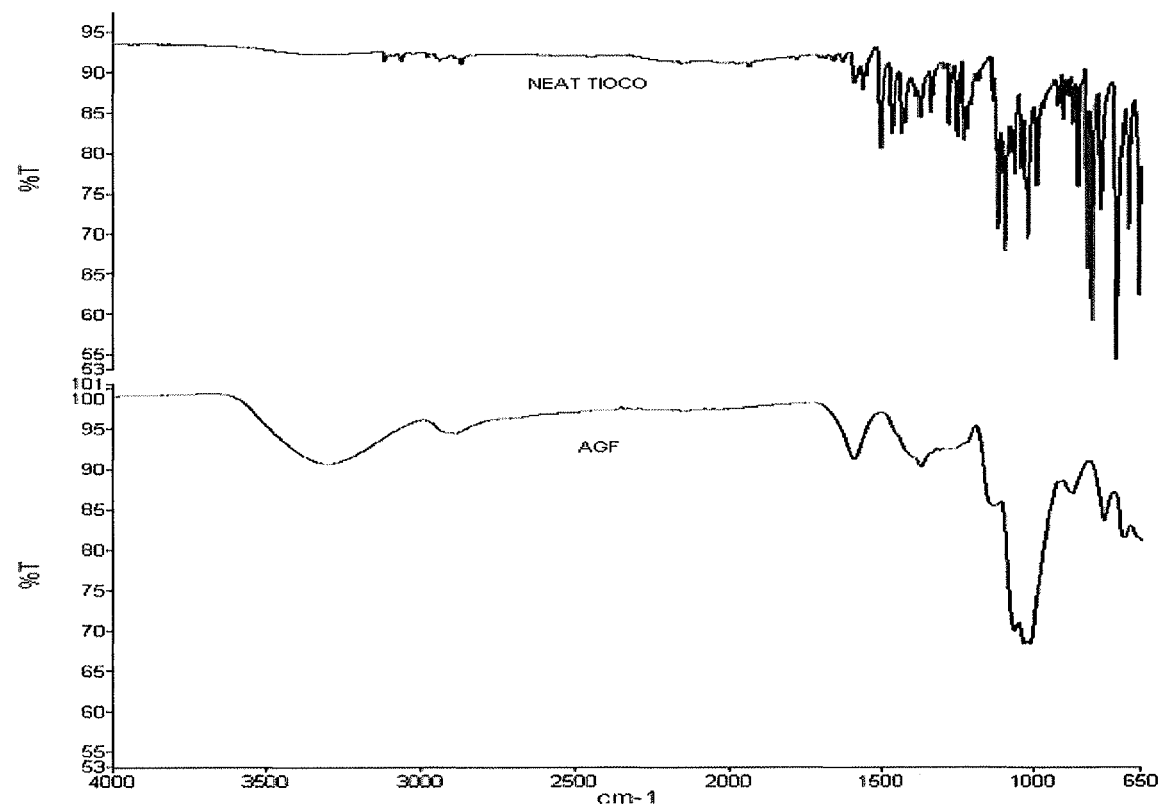
FIG. 32D shows FTIR spectra of NEAT TIOCO and AGF.

No shifts in the major IR band of TIOCO (Appendix) and that of AGF polymer were found, indicating the absence of TIOCO AGF interactions (FIGS. 32C and 32D).

Furosemide (FUROS)

Figure 33A:
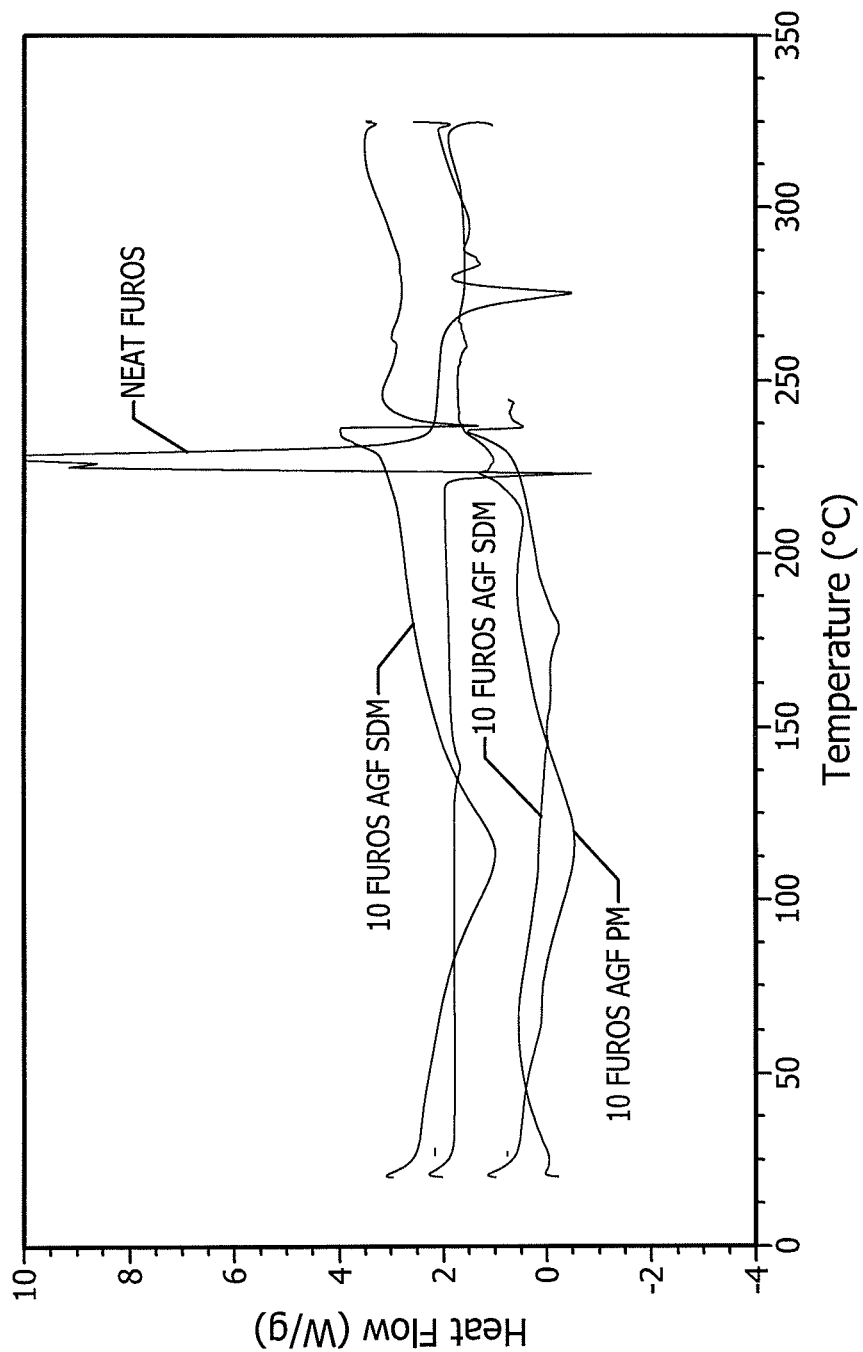
FIG. 33A shows the DSC thermographs of furosemide FUROS AGF PM and FUROS AGF SDM. The melting endotherm is at 228.05° C. From bottom to top (at the 160° C. mark) are shown: 10% FUROS AGF SDM, 10% FUROS AGF PM, NEAT FUROS and 10% FUROS AGF SDM.

The DSC thermogram (FIG. 33A) of NEAT FUROS showed an exothermic peak at 228.05° C. which was found to be associated with the melting of the drug and is indicative of the crystalline nature of the drug. The endothermic peak at 275.15° C. was associated with the degradation product. The endothermic peak of melting of FUROS at 228.05° C. was absent in SDM formulation. Repetition of the DSC scan of another sample of 10% FUROS AGF SDM formulation confirmed the absence of a melting peak of FUROS in SDM formulation. However, the SDM formulation showed another sharp peak at 236° C. It is unlikely that this transition was due to melting. It could be melting of the degradation product at a lower temperature.

Figure 33B:
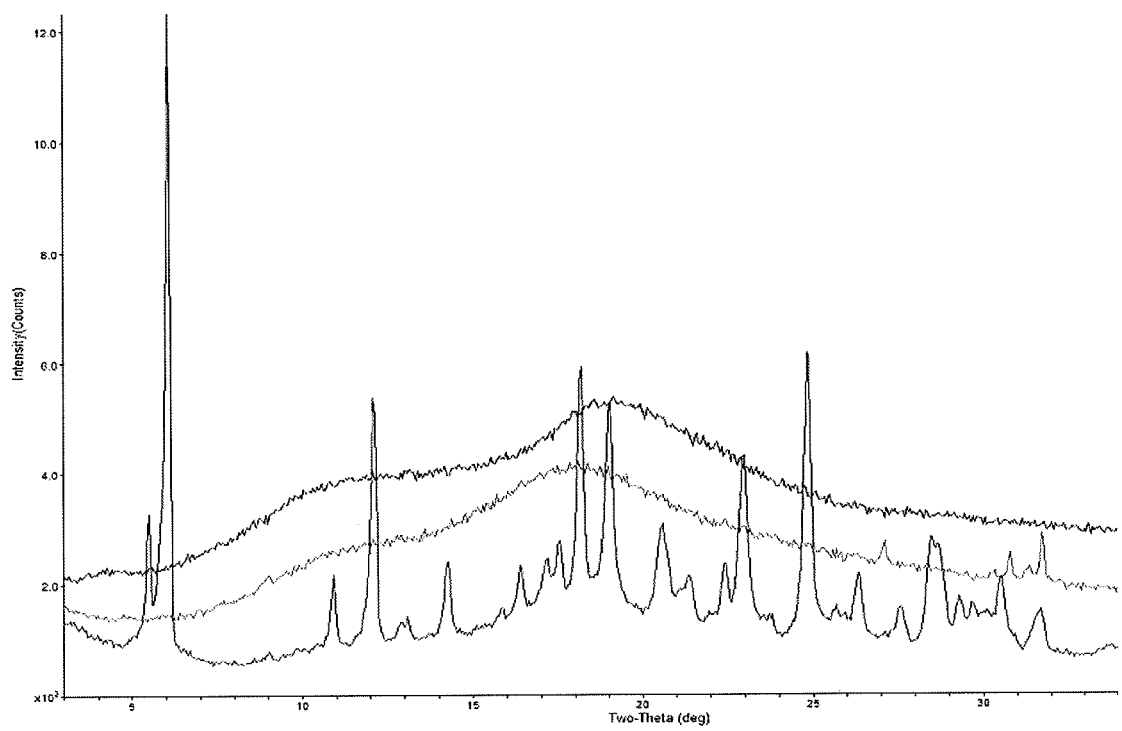
FIG. 33B shows the XRPD of FUROS AGF SDM formulations. From bottom to top are shown: NEAT FUROS, 10% FUROS AGF SDM, NEAT AGF (crystallinity peaks at 2θ of 12°, 18.1°, 19°, 23.9°, 24.8°, 28.4°).

Complete loss of crystallinity was observed in 10% FUROS AGF SDM samples as is clear from the disappearance of highly intense, sharp and less diffuse XRPD peaks at 2θC of 12°, 18.1°, 19°, 23.9°, 24.8 and 28.4°, indicative of FUROS crystallinity. It also confirms that the endotherm at 236° C. was due to a degradation product. The broad endotherm of the 10% FUROS PM formulation suggests little disorder in PM (FIG. 33B).

Figure 33C:
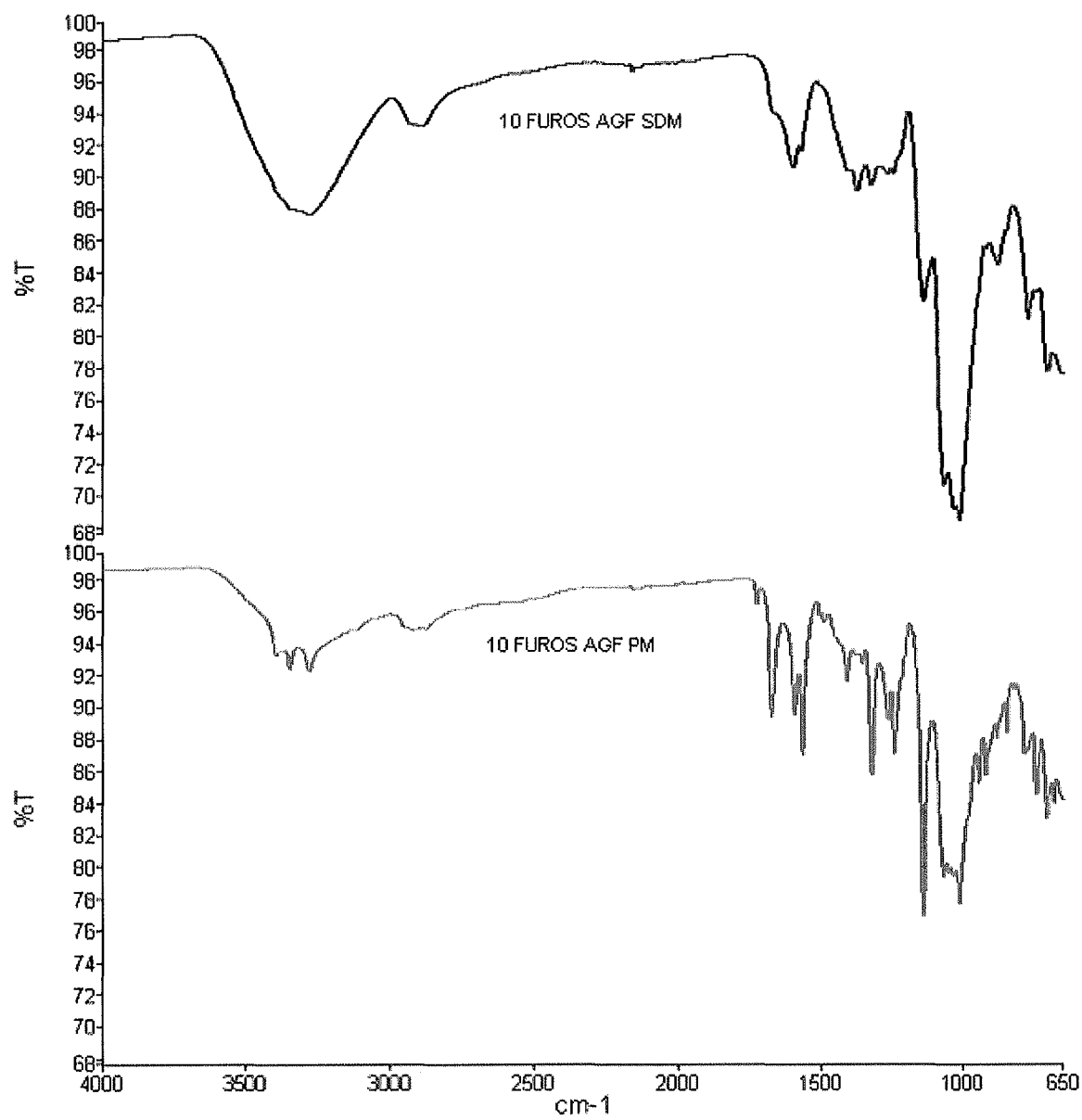
FIG. 33C shows FTIR spectra of 10% FUROS AGF PM AND 10% FUROS AGF SDM.
Figure 33D:
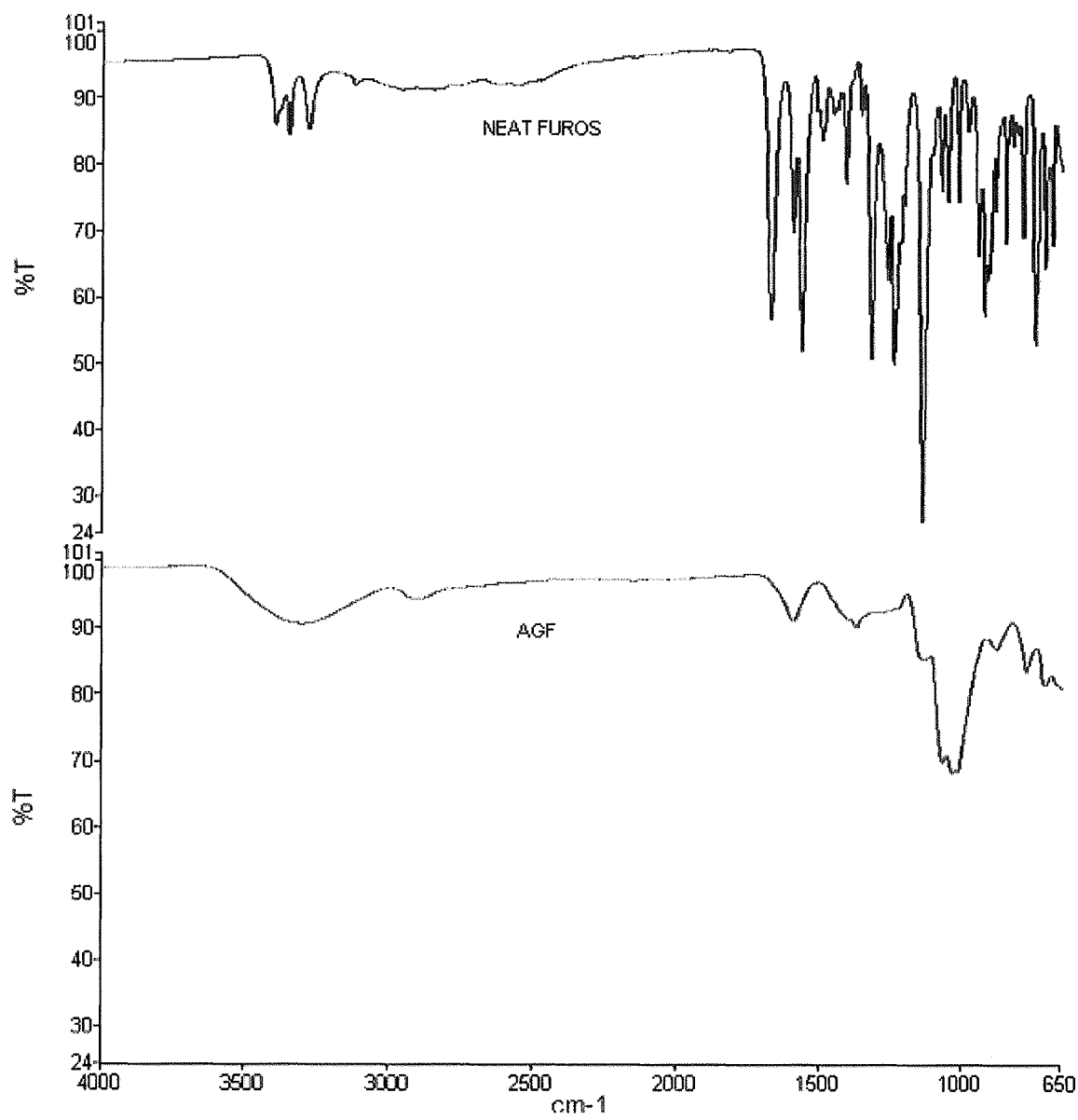
FIG. 33D shows FTIR spectra of NEAT FUROS and AGF.

The shift in the IR band at 3282.76 cm$^{-1}$ (N—H stretch), 1676.31 cm$^{-1}$ (N—H bending) and 1561 cm$^{-1}$ (C═O stretch) suggests involvement of these groups in hydrogen bonding with AGF. The corresponding shifts of AG IR bands at 3284 cm$^{-1}$ (OH) and 1590 cm$^{-1}$ (COO$^-$) were observed in FUROS formulations. (FIGS. 33C and 33D)

Ketoconazole (KETO)

Figure 34A:
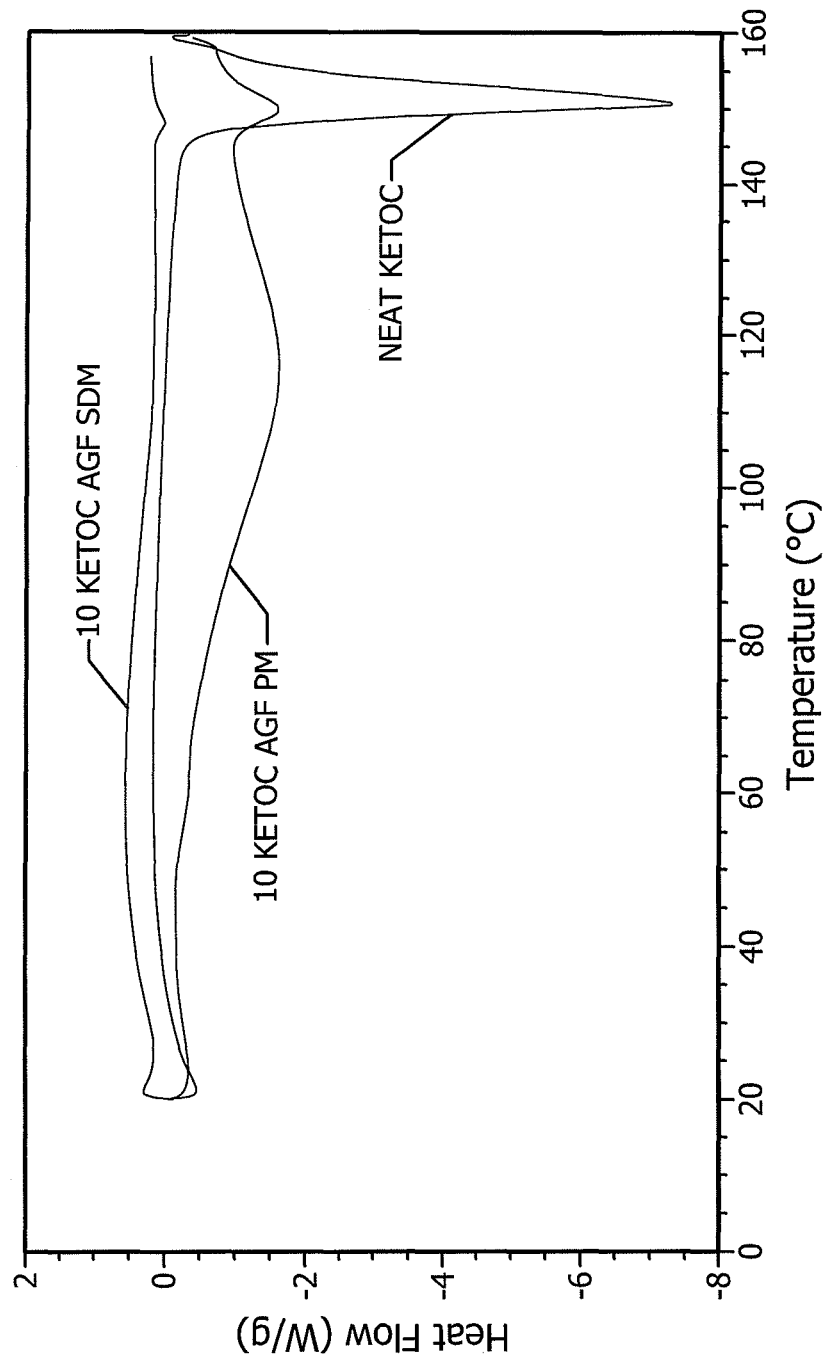
FIG. 34A shows the DSC thermographs of NEAT ketoconazole (KETOC), KETOC AGF PM and KETOC AGF SDM. The melting endotherm is at 150.51° C. From bottom to top (at the 150° C. mark) are shown: NEAT KETOC, 10% KETOC AGF PM and 10% KETOC AGF SDM.
Figure 34B:
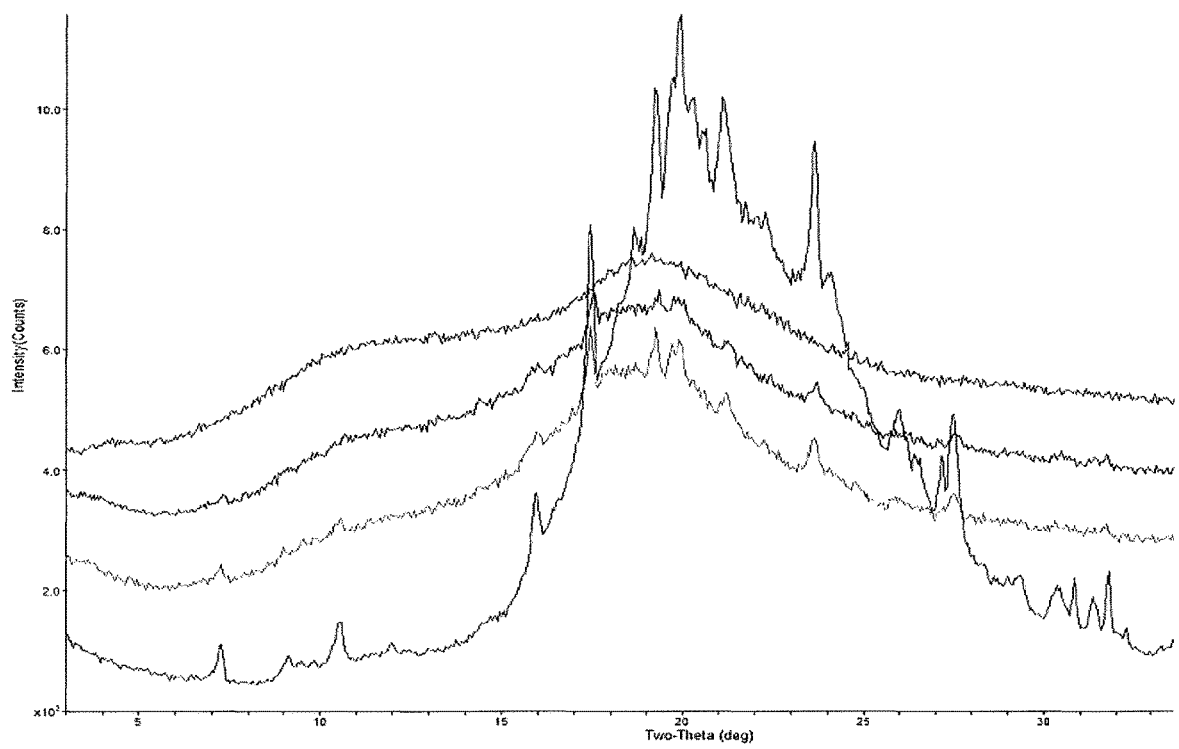
FIG. 34B shows the XRPD of KETOC AGF SDM formulations. From bottom to top at the 10 Two-Theta mark are shown: NEAT KETOC, 10% KETOC AGF PM, 10% KETOC AGF SDM, NEAT AGF (crystallinity peaks at 2θ of 7.21°, 11.95°, 17.44°, 18.6°, 19.94°, 20.34°, 21.01°, 23.6°, 24°, 27.4°).

Partial amorphicity was observed in 10 KETOC AGF SDM formulation. On the other hand, KETOC was almost crystalline in PM (FIG. 34A). The XRPD peaks of 10% SDM were shifted and were present with less intensity. However, KETOC crystallinity was retained in 10% PM formulation (FIG. 34B).

Figure 34C:
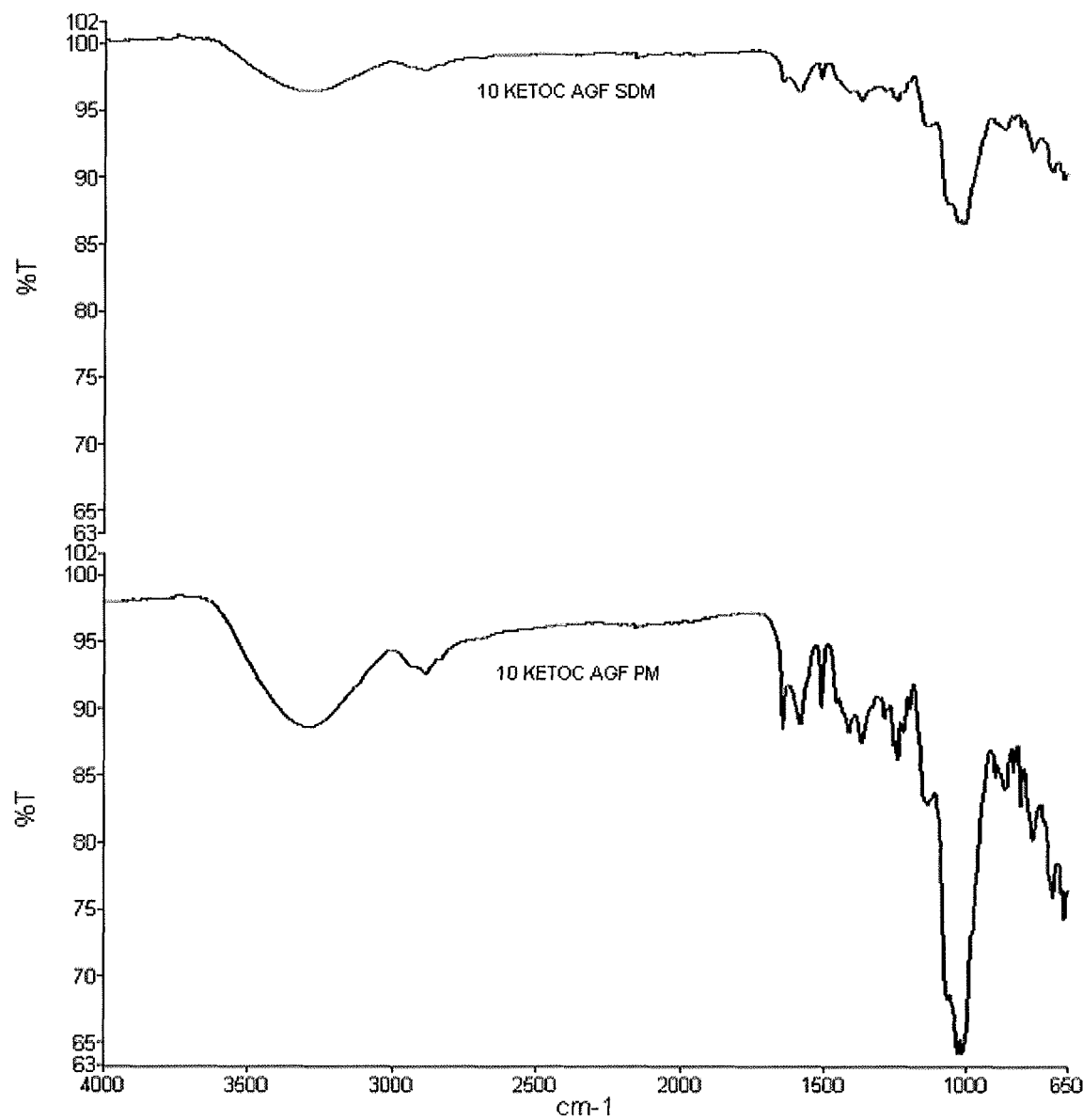
FIG. 34C shows FTIR spectra of 10% KETOC AGF PM AND 10% KETOC AGF SDM.
Figure 34D:
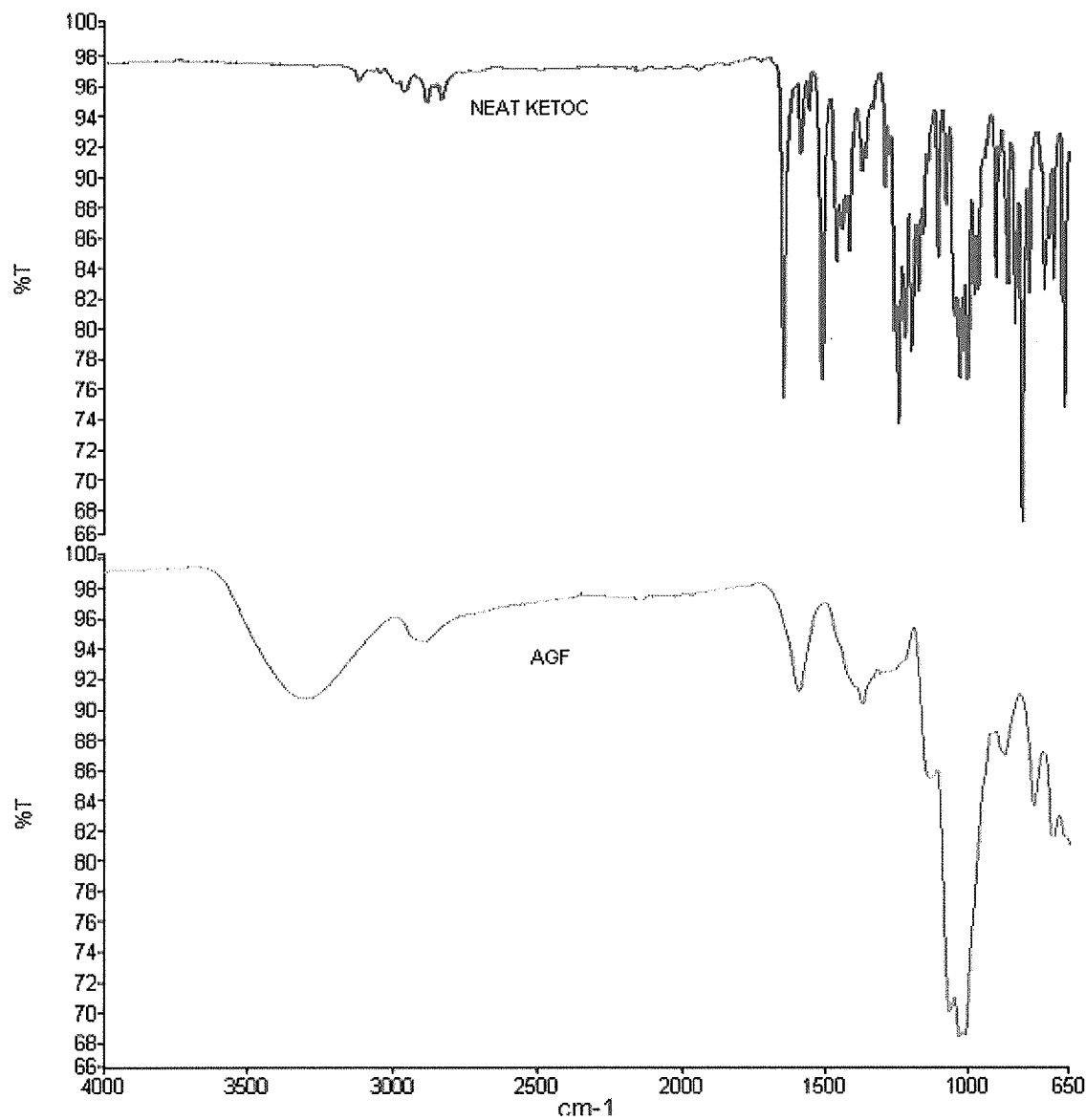
FIG. 34D shows FTIR spectra of NEAT KETOC and AGF.

The shifts in the major IR band of NEAT KETOC and NEAT AGF are depicted in FIGS. 34C and 34D. There was no shift in the IR band at 1645 cm$^{-1}$ (C═O stretch) in SDM and PM formulations compared to NEAT KETOC. However, the intensity of the IR band in SDM formulation was decreased compared to PM formulation. It suggests some degree of interaction in between the AGF and KETOC in the SDM formulation. However, the PM formulation was devoid of any interactions.

Propranolol Free Base (PROPFB)

Figure 35A:
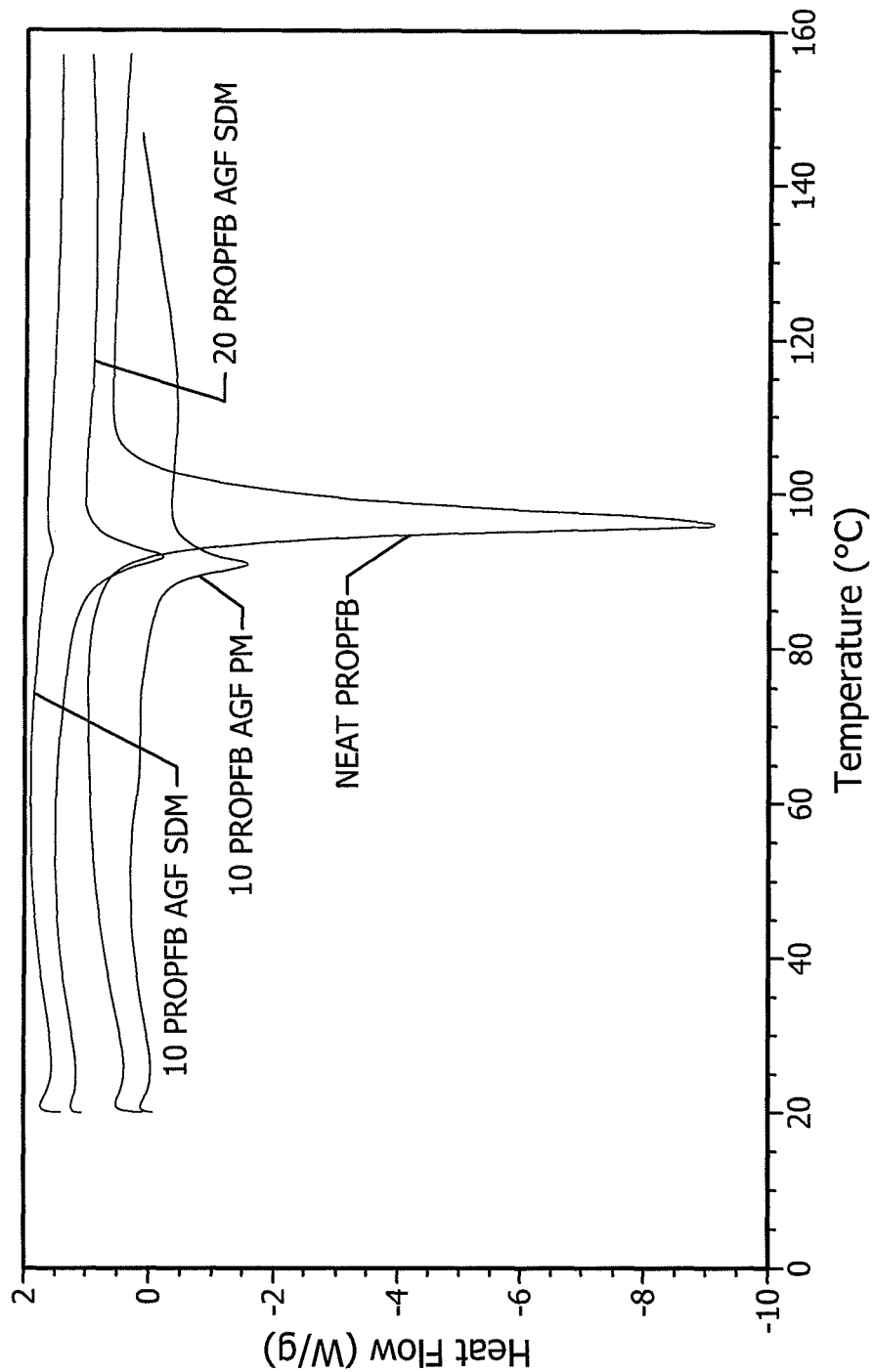
FIG. 35A shows the DSC thermographs of propranolol free base (PROPFB) AGF PM and PROPFB AGF SDM. The melting endotherm is at 95.86° C. From bottom to top (at the 120° C. mark) are shown: 10% PROPFB AGF PM, NEAT PROPFB, 20% PROPFB AGF SDM and 10% PROPFB AGF SDM.
Figure 35B:
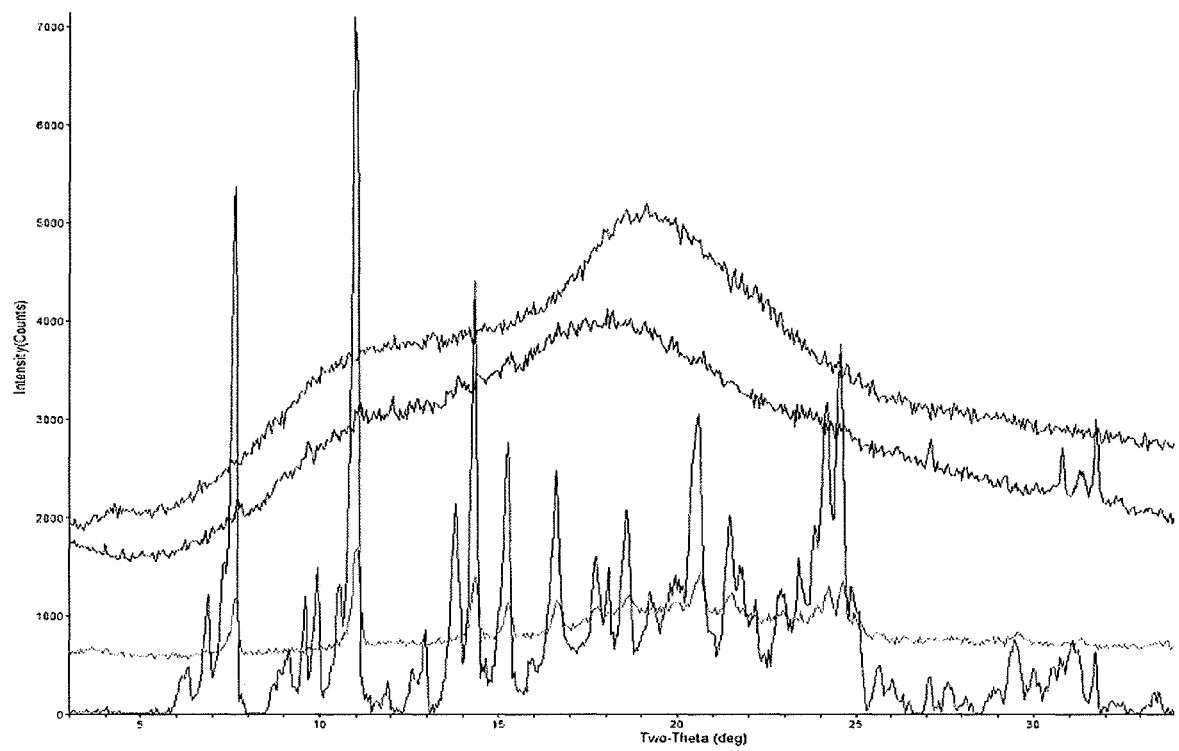
FIG. 35B shows the XRPD of PROPFB AGF SDM formulations. From bottom to top are shown: NEAT PROPFB, 10% PROPFB AGF PM, 10% PROPFB AGF SDM, NEAT AGF (crystallinity peaks at 2θ of 7.6°, 10.9°, 14.3°, 15.2°, 20.6°, 24.2°, 24.5°).

The DSC and XRPD findings indicated amorphous PROPFB in SDM formulation up to 10% drug load. However, PROPFB reminded crystalline in PM formulation (FIG. 35A and FIG. 35B).

Figure 35C:
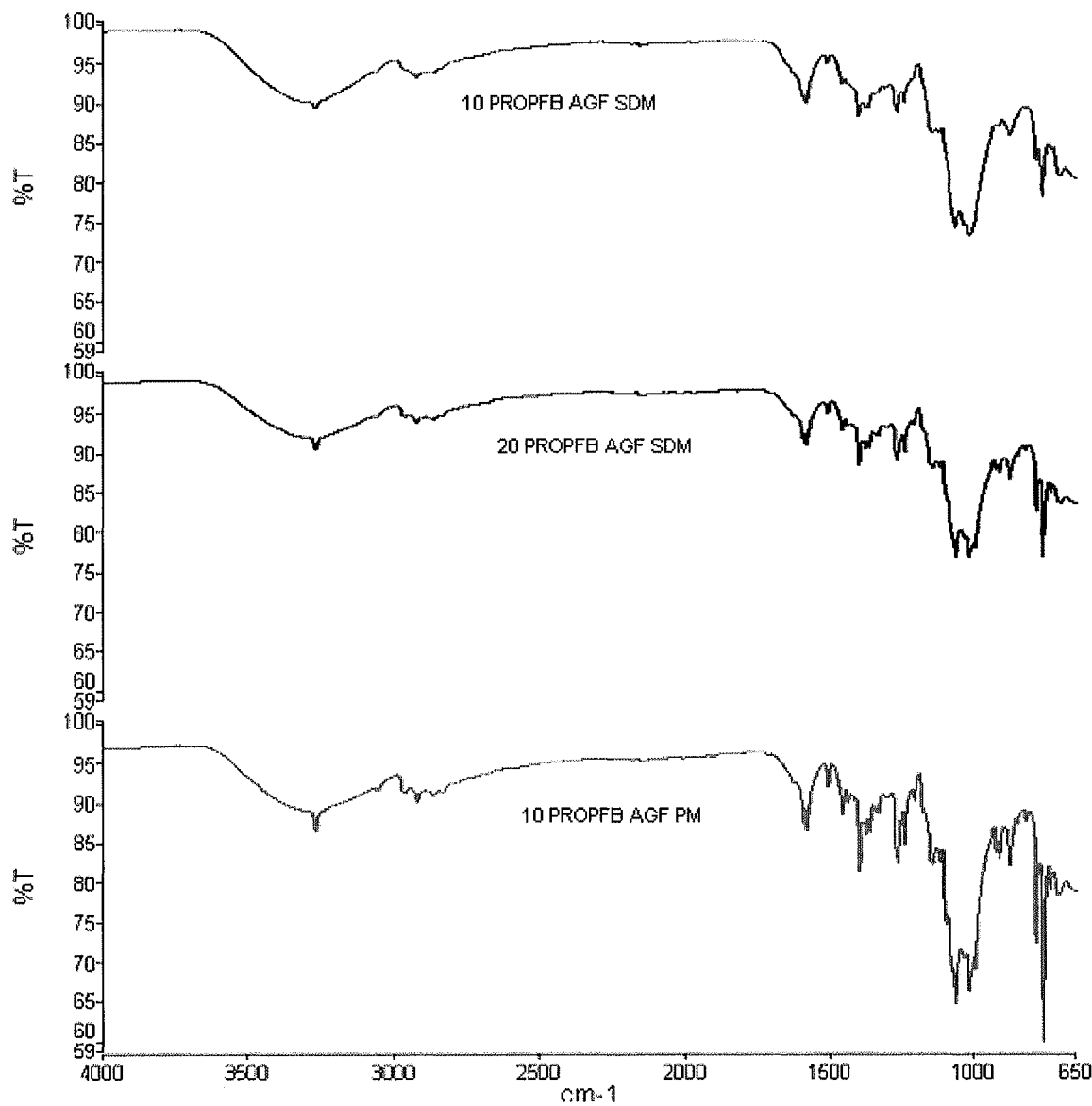
FIG. 35C shows FTIR spectra of 10% PROPFB AGF PM, 10% PROPFB AGF SDM AND 20% PROPFB AGF SDM.
Figure 35D:
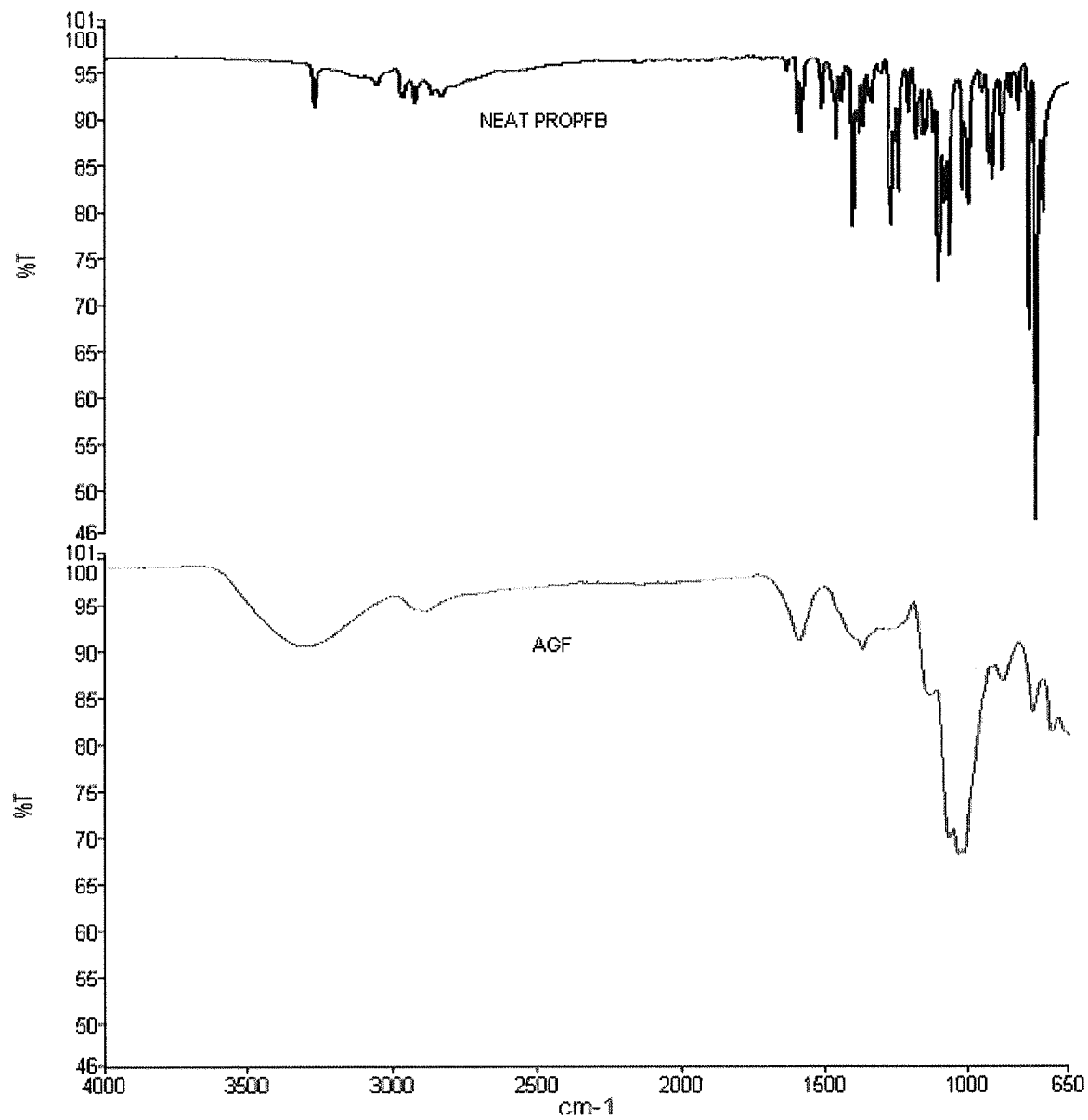
FIG. 35D shows FTIR spectra of NEAT PROPFB and AGF.

There was no change in the intensity and shift in the IR band of PROPFB and AGF polymer (FIG. 35C). In fact, the SDM and PM spectra looked like the sum of the FTIR spectra of NEAT PROPFB and NEAT AGF. Thus, the absence of hydrogen bonding was confirmed in the PROPFB AGF SDM system. No covalent bonding between the therapeutic agent and the arabinogalactan is detected in the FTIR data for the SDM formulations (FIG. 35C).

Naproxen (NAPROX)

Figure 36A:
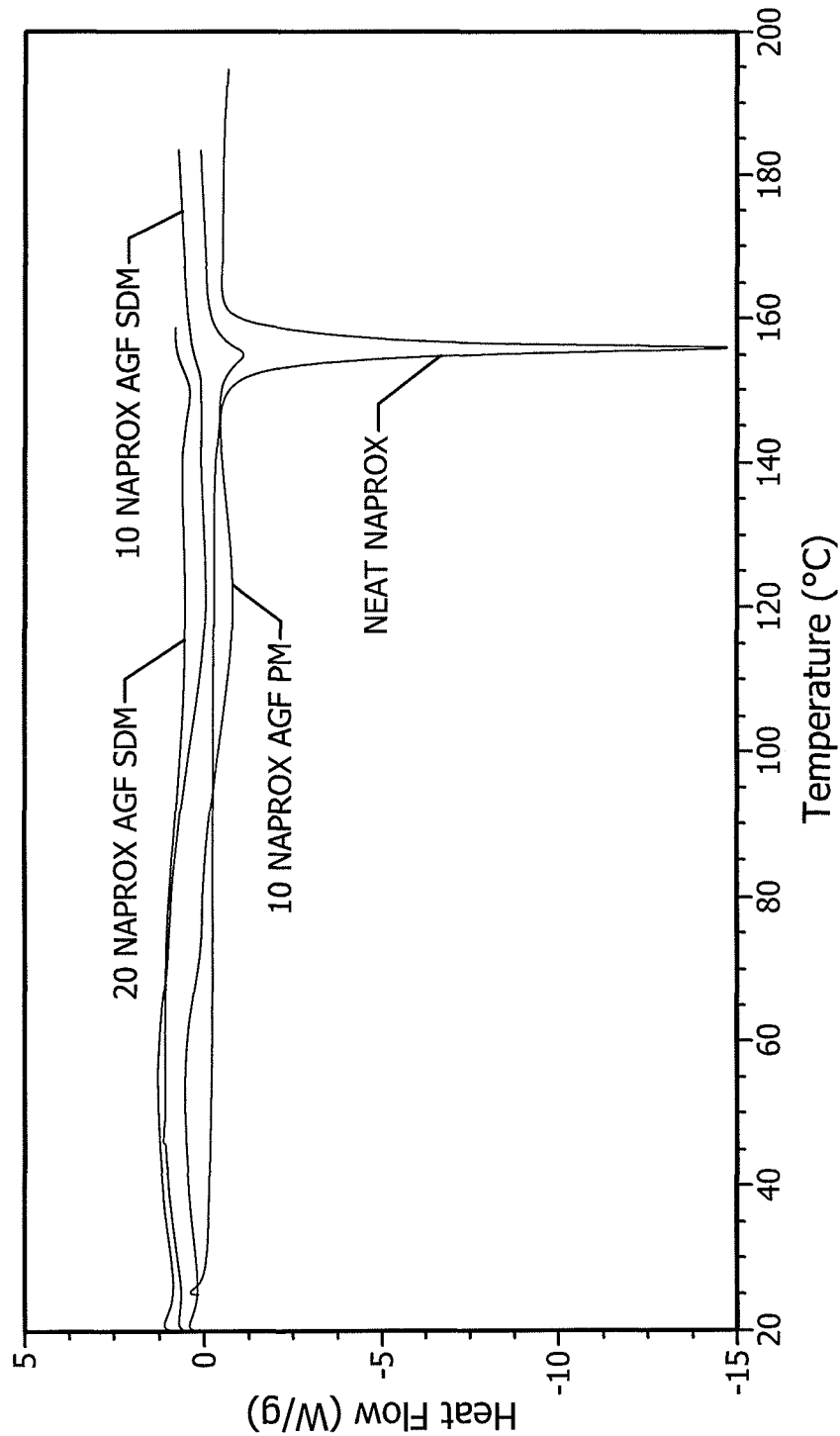
FIG. 36A shows the DSC thermographs of naproxen (NAPROX) AGF PM and NAPROX AGF SDM. The melting endotherm is at 155.93° C. From bottom to top (at the 155° C. mark) are shown: NEAT NAPROX, 10% NAPROX AGF PM, 10% NAPROX AGF SDM and 20% NAPROX AGF SDM.
Figure 36B:
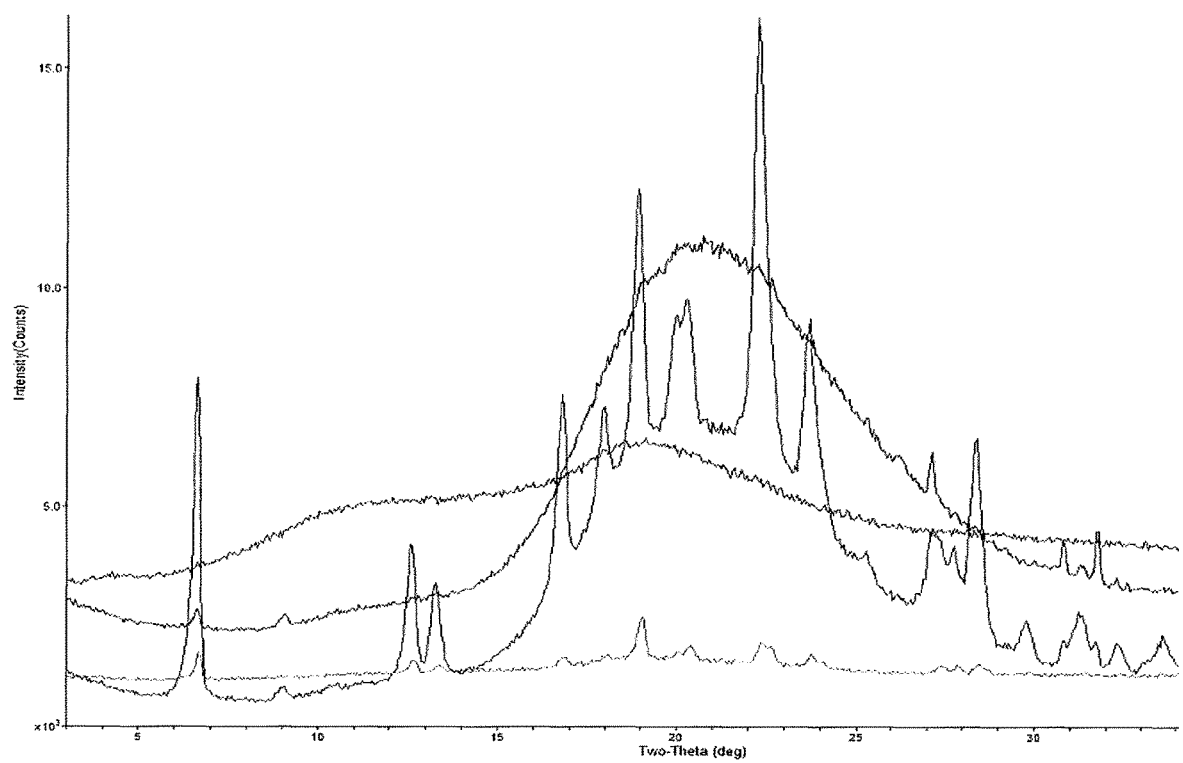
FIG. 36B shows the XRPD of NAPROX AGF SDM formulations. From bottom to top are shown: NEAT NAPROX, 20% NAPROX AGF SDM, 10% NAPROX AGF SDM, NEAT AGF (crystallinity peaks at 2θ of 6.6°, 12.6°, 16.7°, 18.94°, 20.25°, 22.25°, 23.69°, 28.35°).

DSC analysis (FIG. 36A) showed the absence of melting endotherm of NEAT NAPROX in 10% SDM formulation whereas it was present with low intensity in 20% SDM formulation. XRPD overlays are shown in FIG. 36B. The disappearance of the diffraction peak at 12.6° was found in 10% NAPROX AGF SDM and other peaks were present with less intensity and showed shifts. On the other hand, the diffraction peaks were present with reduced intensity in 20% NAPROX SDM. Thus both DSC and XRPD findings proved the complete amorphization of NAPROX in 10% SDM formulation whereas partial amorphization was observed in 20% SDM formulation. The PM formulation retained the NAPROX in crystalline form.

Figure 36C:
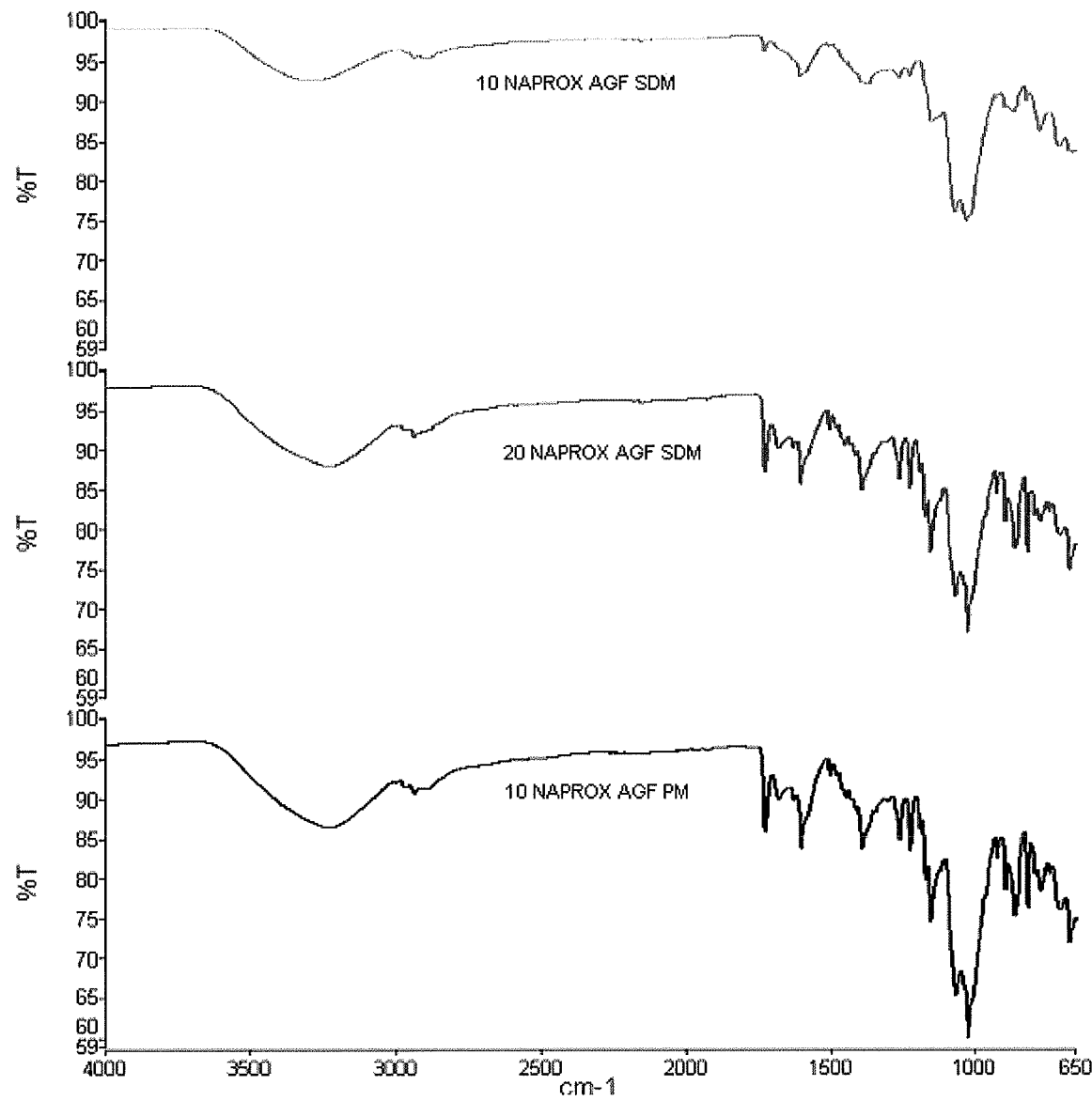
FIG. 36C shows FTIR spectra of 10% NAPROX AGF PM, 10% NAPROX AGF SDM AND 20% NAPROX AGF SDM.
Figure 36D:
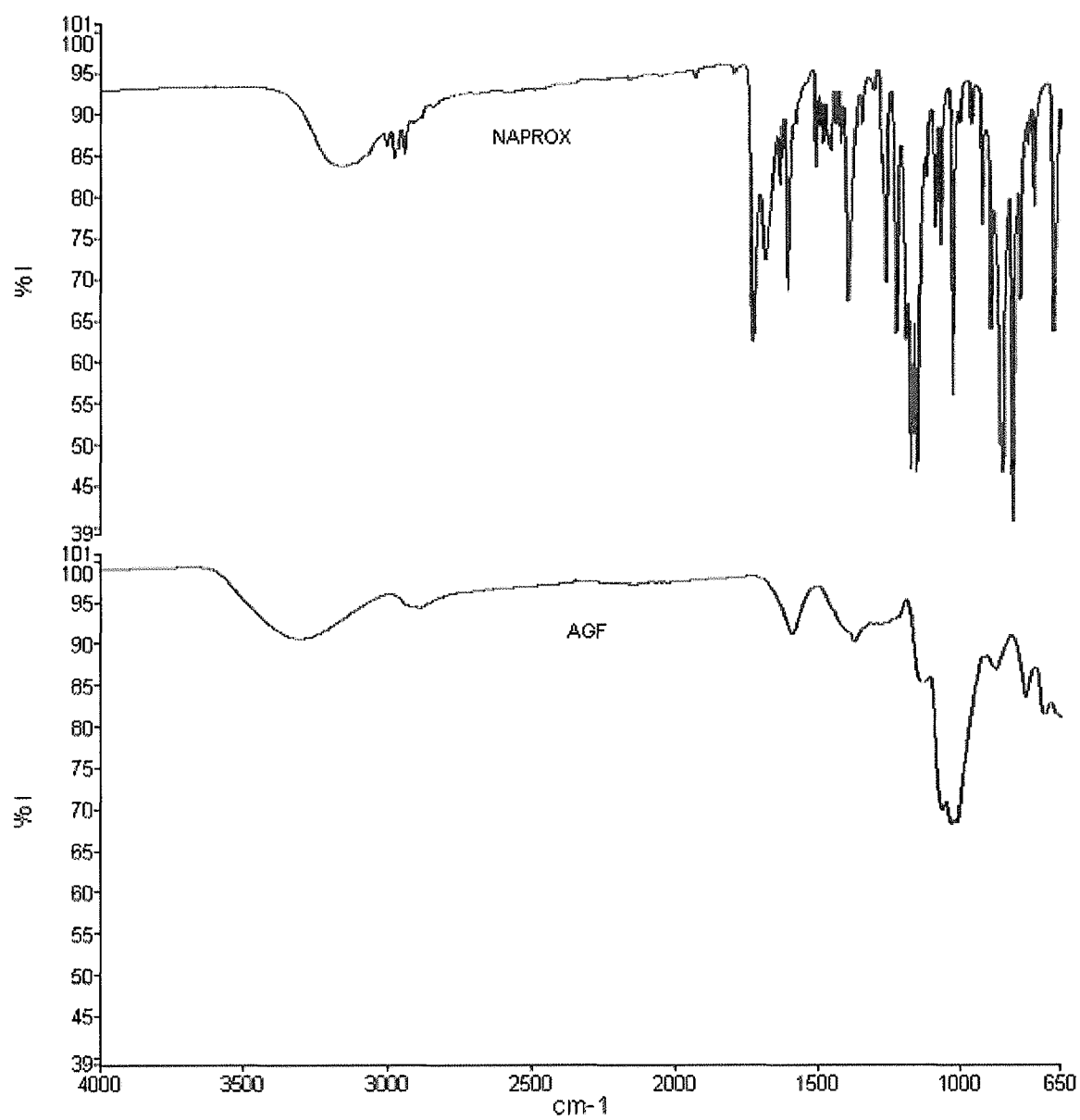
FIG. 36D shows FTIR spectra of NEAT NAPROX and AGF.

The shift in the NAPROX IR bands at 1726 cm$^{-1}$ (C=O stretch), at 1394 cm$^{-1}$ (COO$^{-1}$) and the shift in AGF's IR band at 3308 cm$^{-1}$ (OH stretch) in 10% NAPROX AGF SDM indicate the formation of hydrogen bonds between NAPROX and AGF. Whereas in 20% NAPROX SDM, there was no shift in the NAPROX IR band at 1394 cm$^{-1}$ (COO$^{-1}$) indicating free carboxylic group has less role in hydrogen bonding in 20% NAPROXEN AGF SDM. The PM formulations are devoid of any interactions (FIG. 36C).

Flurbiprofen (FLURB)

Figure 37A:
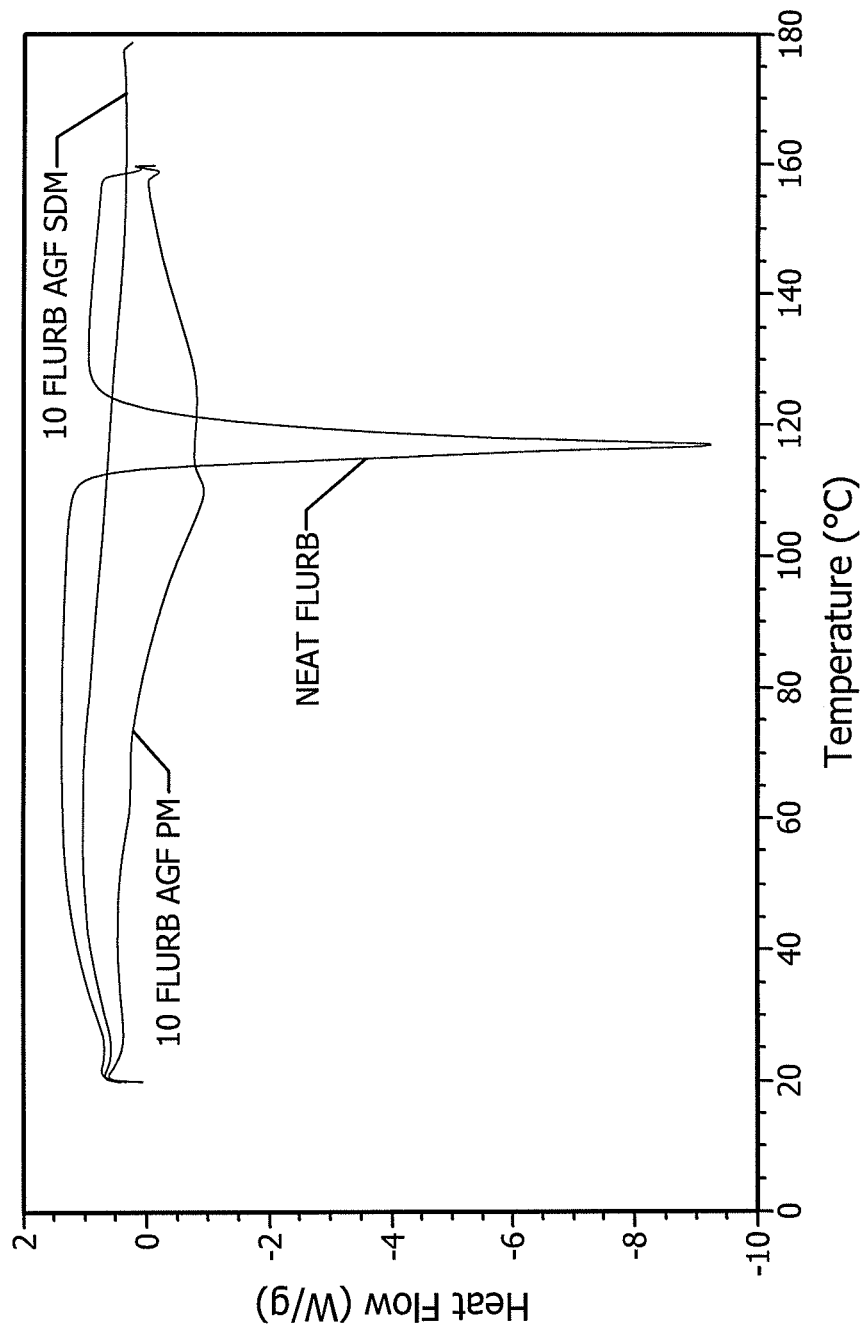
FIG. 37A shows the DSC thermographs of flurbiprofen (FLURBI) AGF PM and FLURBI AGF SDM. The melting endotherm is at 121.57° C. From bottom to top (at the 100° C. mark) are shown: 10% FLURBI AGF PM, 10% FLURBI AGF SDM and NEAT FLURBI.
Figure 37B:
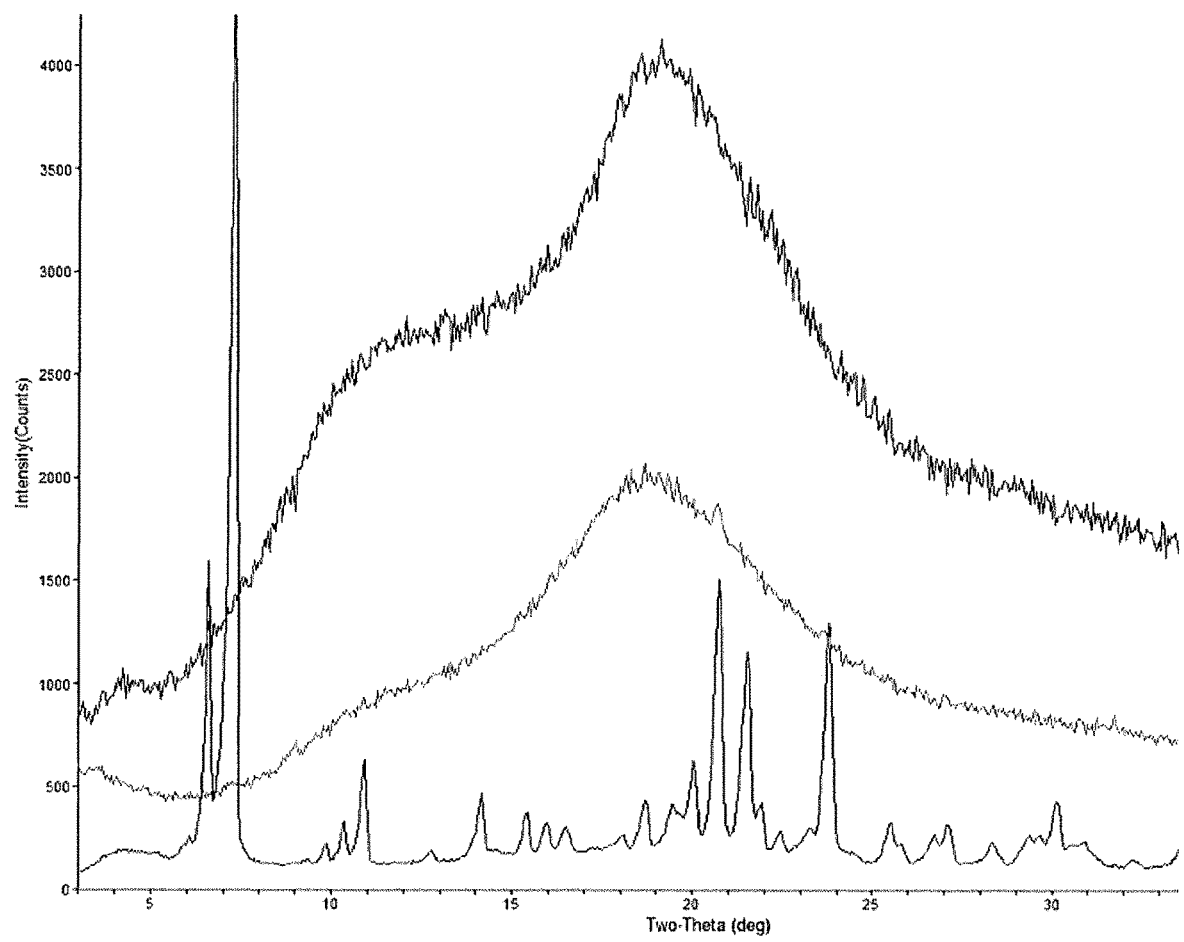
FIG. 37B shows the XRPD of FLURBI AGF SDM formulations. From bottom to top are shown: NEAT FLURBI, NEAT AGF, 10% FLURBI AGF SDM (crystallinity peaks at 2θ of 7.3°, 10.92°, 20.74°, 21.53°, 23.79°, 25.5°, 30.14°).
Figure 37C:
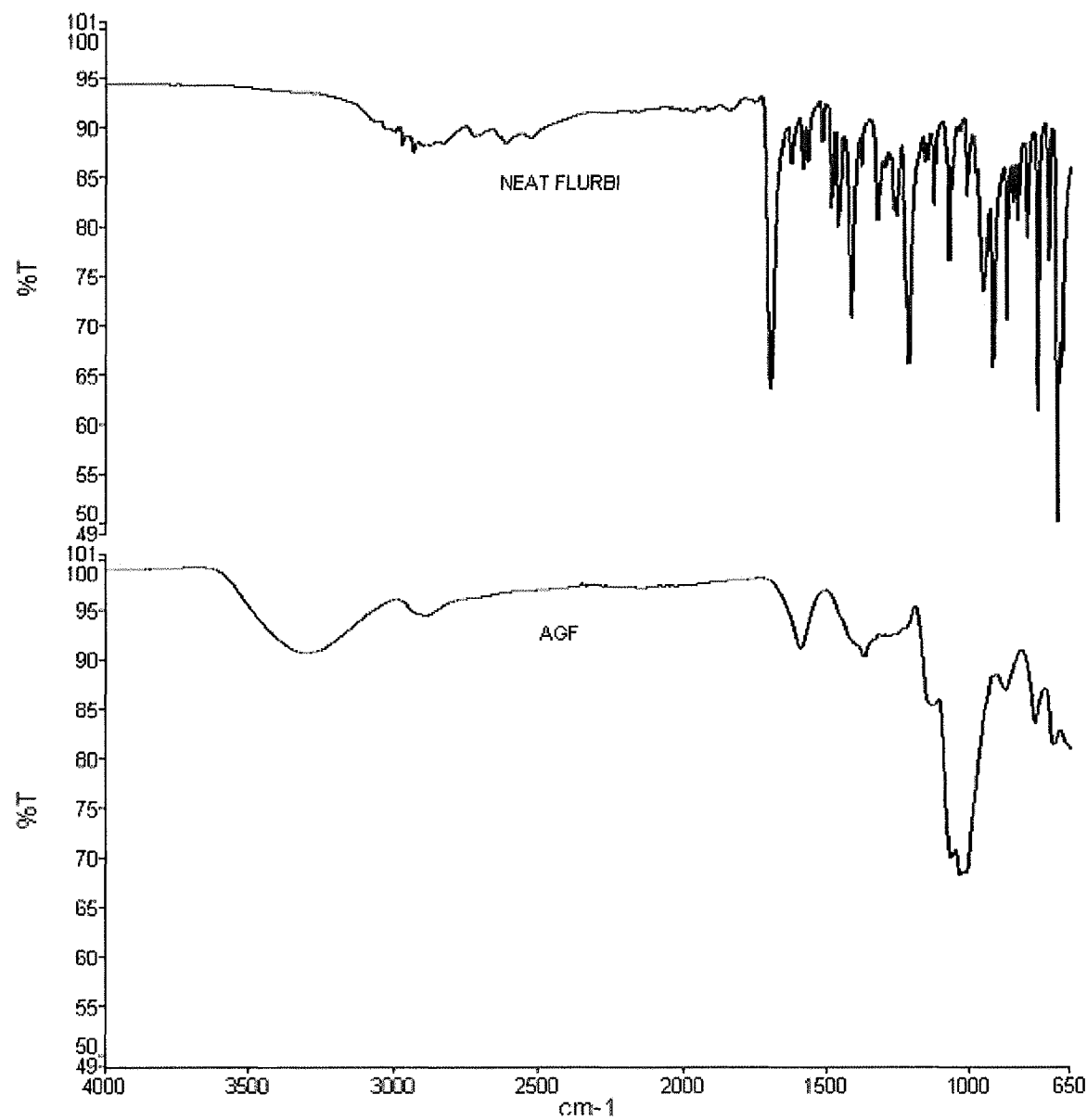
FIG. 37C shows FTIR spectra of NEAT FLURBI and AGF.
Figure 37D:
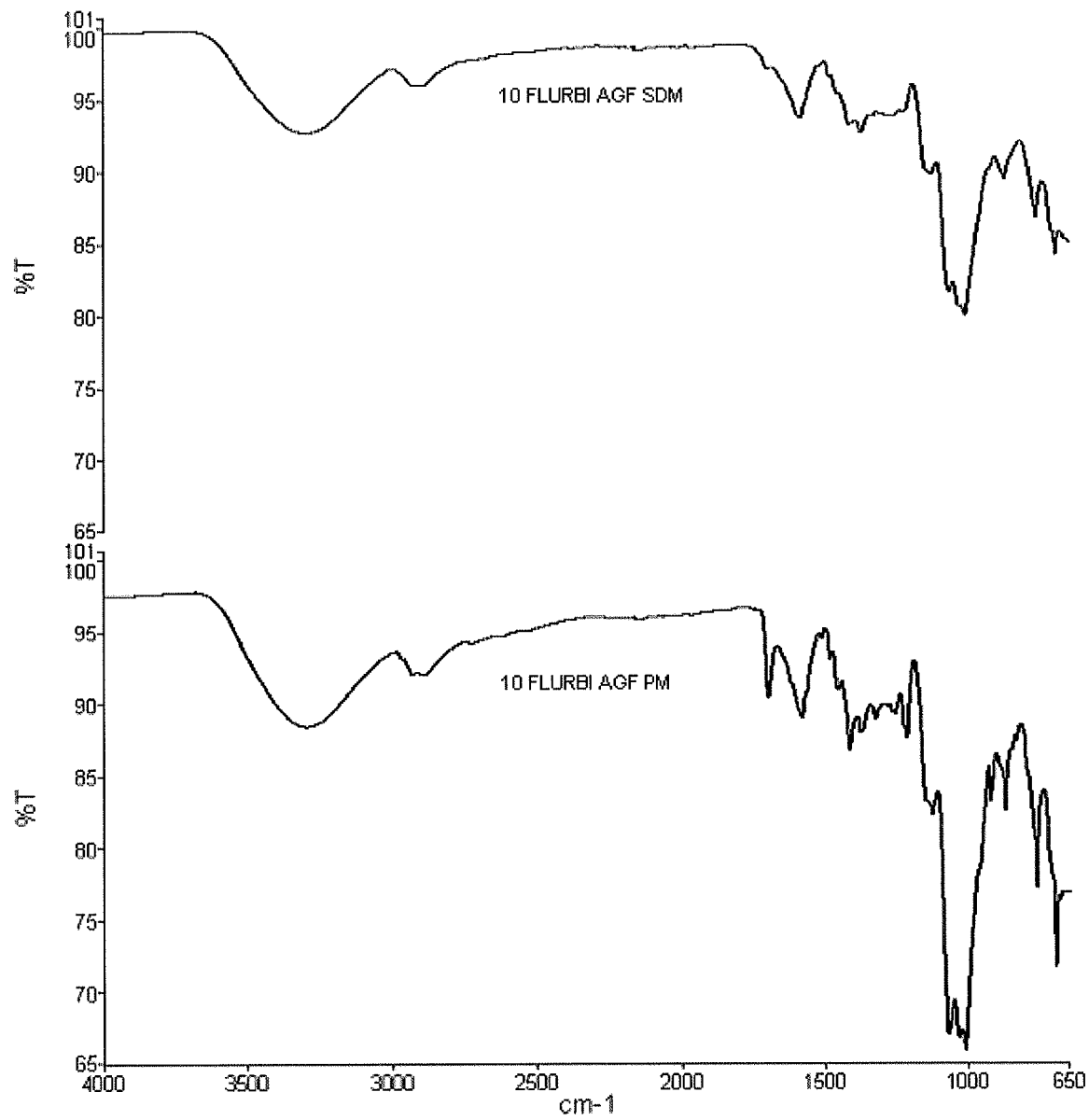
FIG. 37D shows FTIR spectra of 10% FLURBI AGF PM AND 10% FLURBI AGF SDM.

The overlay of DSC thermographs and XRPD patterns are shown in FIG. 37A and FIG. 37B. Full amorphicity in 10% FLURBI AGF SDM formulation was obvious. There is a possibility of disorder in the PM formulation as is evident from the broadening of the melting endotherm of 10% FLURBI AGF PM. The shift of the FLURBI IR band at 1694 cm$^{-1}$ (C=O stretch) and the AG FIR band at 3308 cm$^{-1}$ (OH stretch) indicated the existence of hydrogen bonding between FLURBI and AGF (FIGS. 37C and 37D).

Nimodipine (NIMO)

Figure 38A:
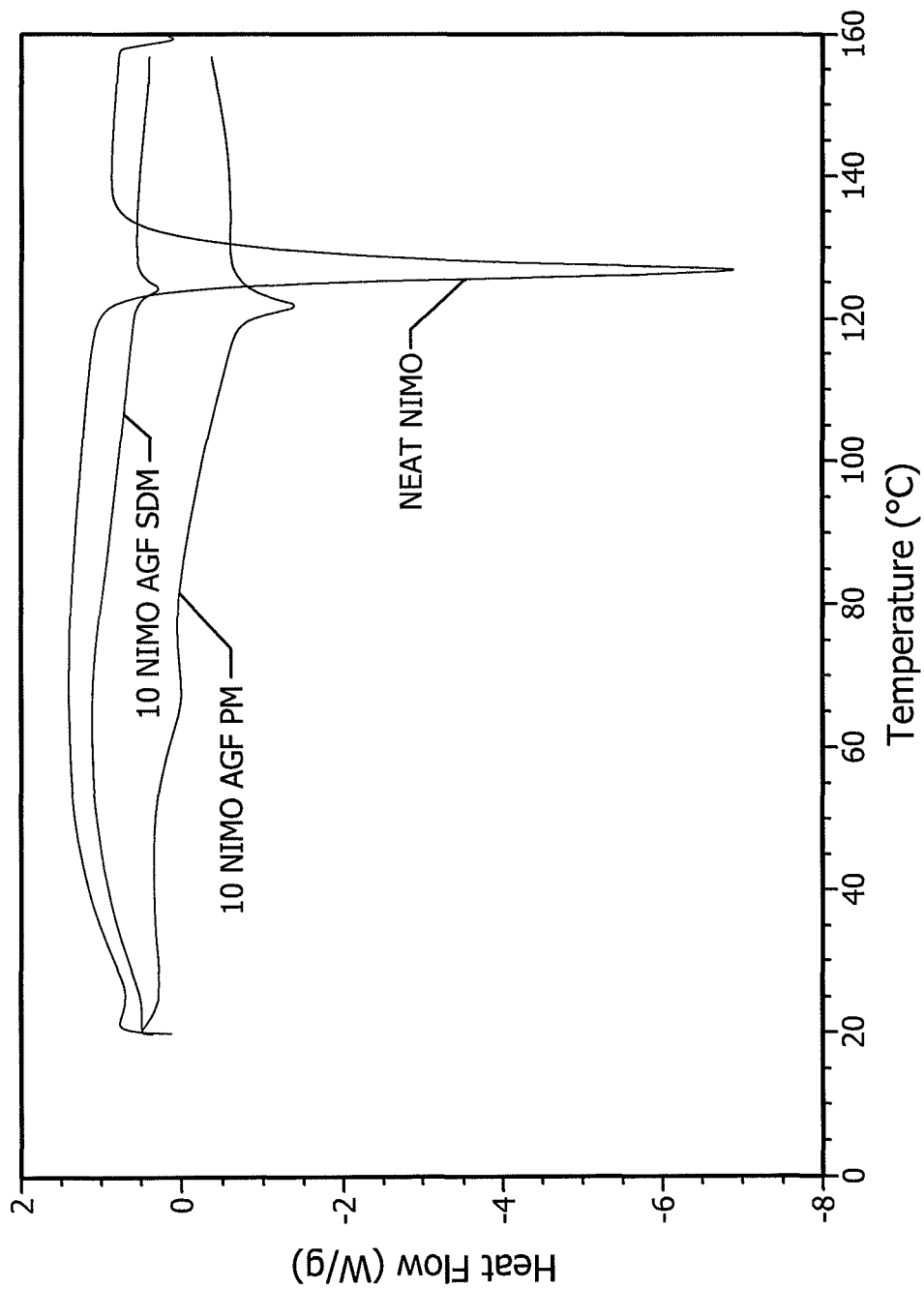
FIG. 38A shows the DSC thermographs of nimopidine (NIMO) AGF PM and NIMO AGF SDM. The melting endotherm is at 126.77° C. From bottom to top (at the 100° C. mark) are shown: 10% NIMO AGF PM, 10% NIMO AGF SDM and NEAT NIMO.
Figure 38B:
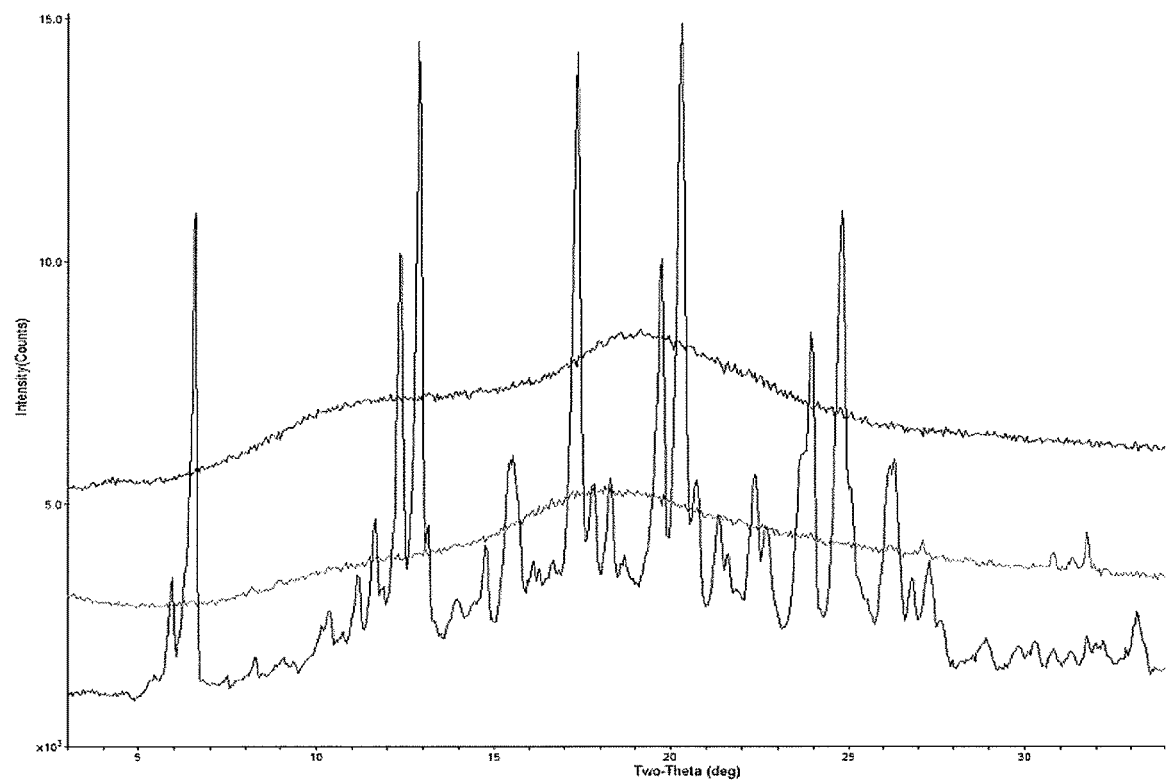
FIG. 38B shows the XRPD of NIMO AGF SDM formulations. From bottom to top are shown: NEAT NIMO, 10% NIMO AGF SDM, NEAT AGF (crystallinity peaks at 2θ of 6.54°, 12.8°, 17.3°, 20.2°, 24.8°, 24.7°).

A significant reduction in the crystallinity was observed in 10% NIMO AGF SDM formulations (FIG. 38A). The diffraction peak at 17.3° was shifted to 17.2° in 10% NIMO AGF SDM whereas other peaks were absent. The overall XRPD pattern of 10% NIMO AGF SDM was suggestive of complete NIMO amorphization. DSC of another sample showed a similar reduction in crystallinity in 10% NIMO AGF SDM formulations (FIG. 38B).

Although XRPD can successfully detect amorphous material down to the level of 5%, it is comparable to DSC in detecting trace crystallinity in amorphous drug dispersions. Thus, DSC and XRPD results together suggest almost complete amorphization in the NIMO SDM sample. However, complete NIMO crystallinity was retained in the 10% NIMO AGF PM formulations.

Figure 38C:
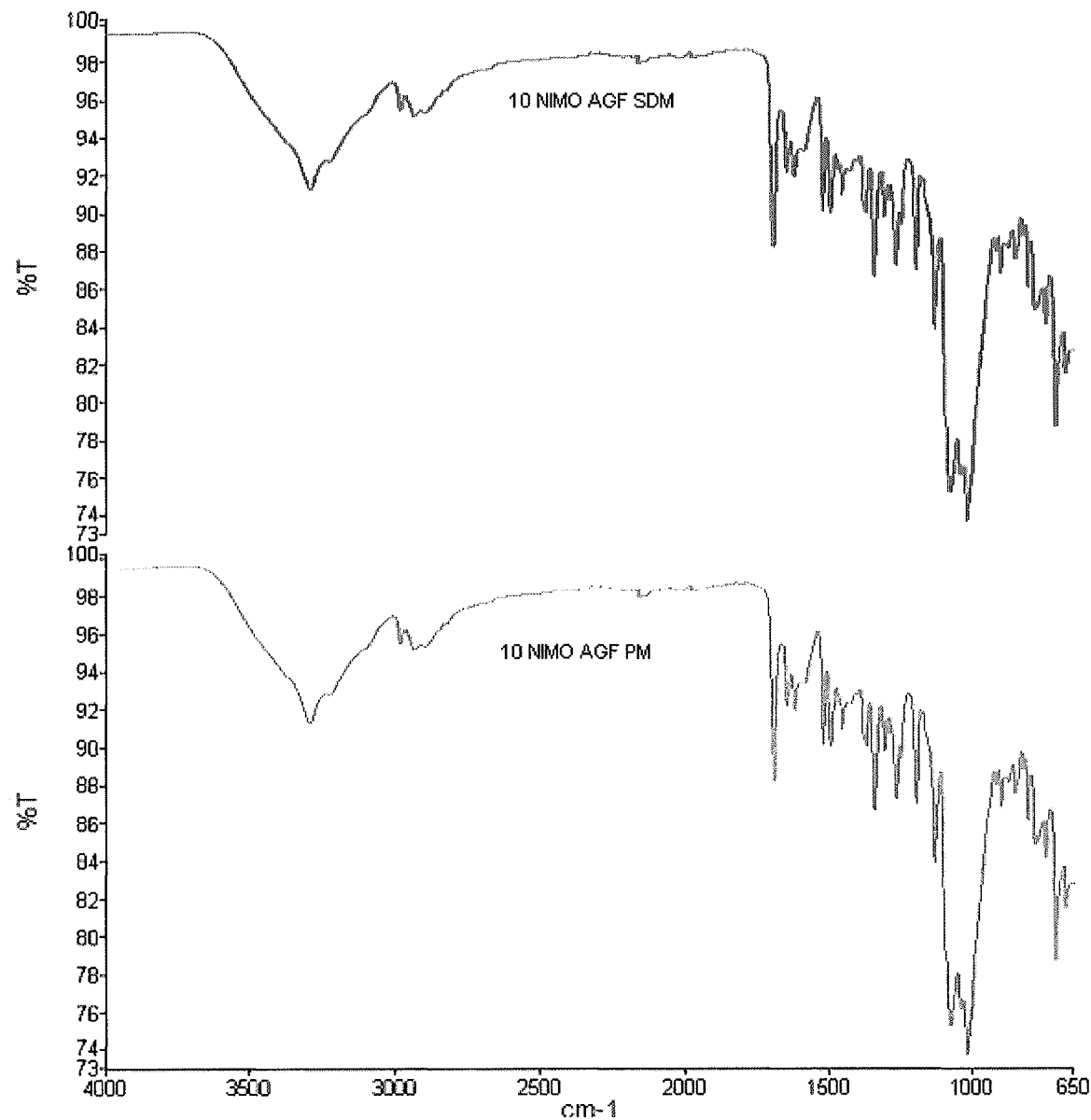
FIG. 38C shows FTIR spectra of 10% NIMO AGF PM AND 10% NIMO AGF SDM.
Figure 38D:
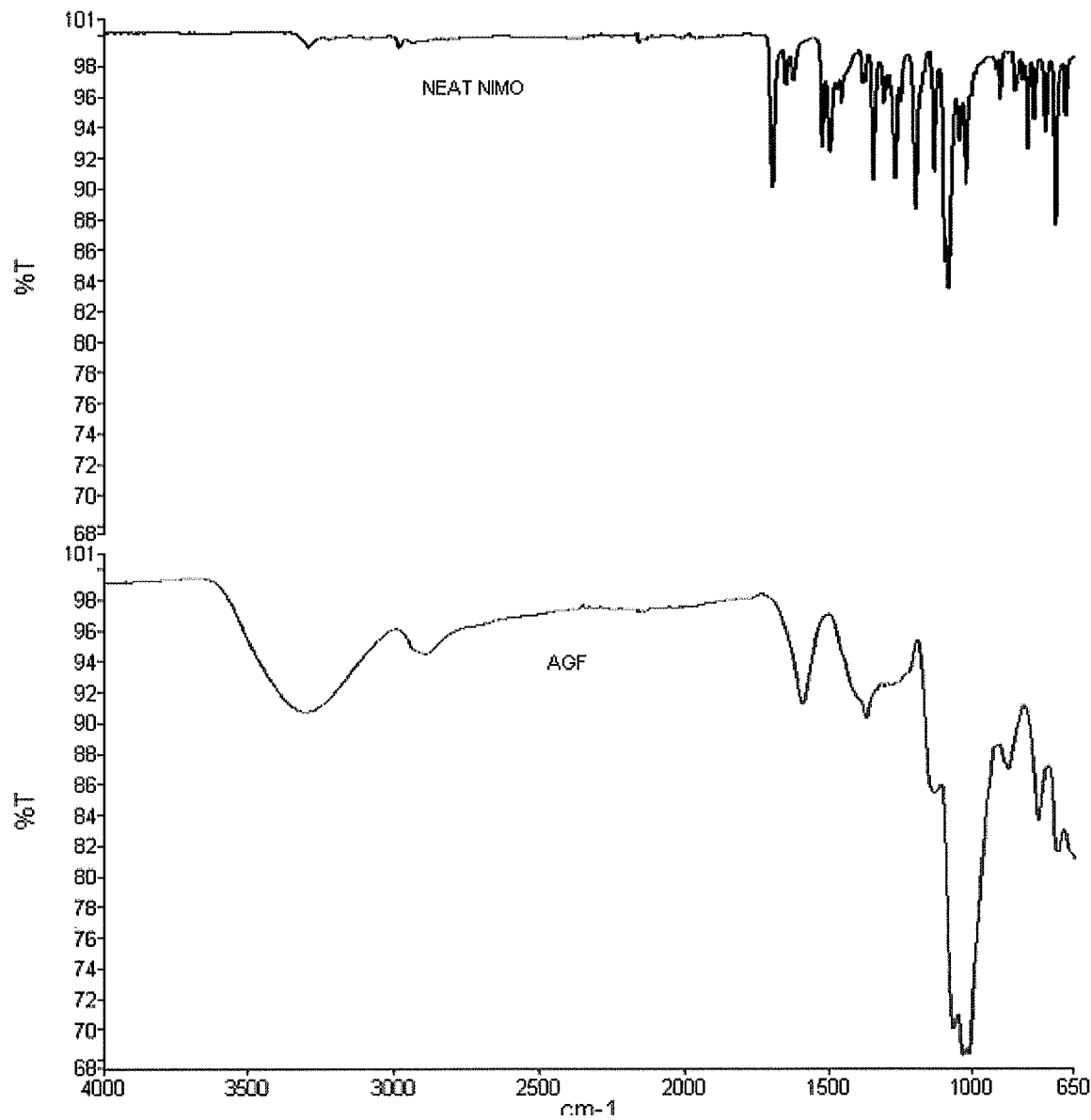
FIG. 38D shows FTIR spectra of NEAT NIMO and AGF.

Hydrogen bonding was present in 10% NIMO AGF SDM formulation as well as in physical mixtures as is clear from the shifts in the IR band at 1693 cm$^{-1}$ of NIMO (C=O stretch) and in the IR band at 3308 cm$^{-1}$ (OH stretch) of AGF polymer (FIGS. 38C and 38D).

Chlorpromamide (CHLOPR)

Figure 39A:
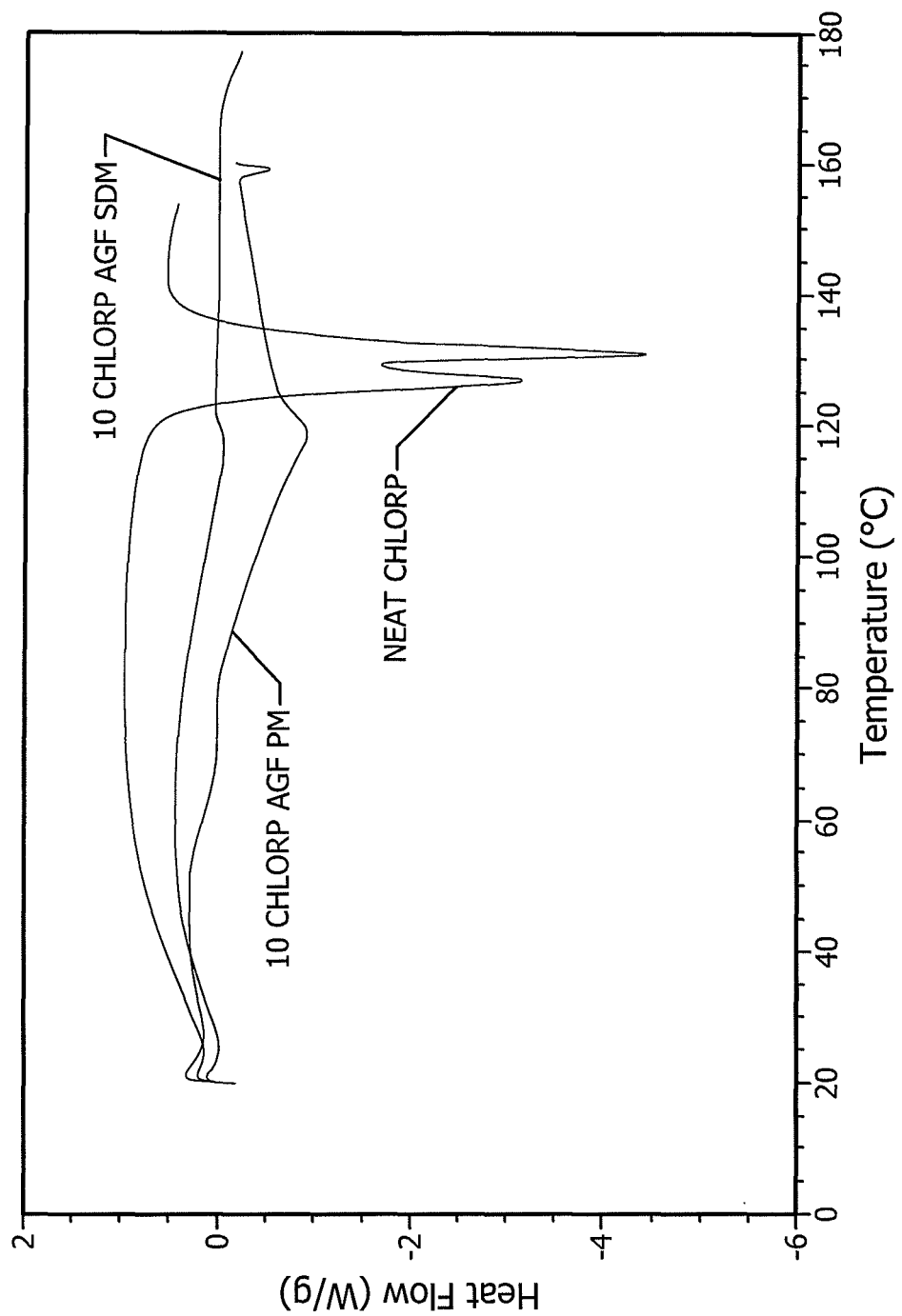
FIG. 39A shows the DSC thermographs of chlorpropamide (CHLORP) AGF PM and CHLORP AGF SDM. The melting endotherm is at 130.84° C. From bottom to top (at the 100° C. mark) are shown: 10% CHLORP AGF PM, 10% CHLORP AGF SDM and NEAT CHLORP.
Figure 39B:
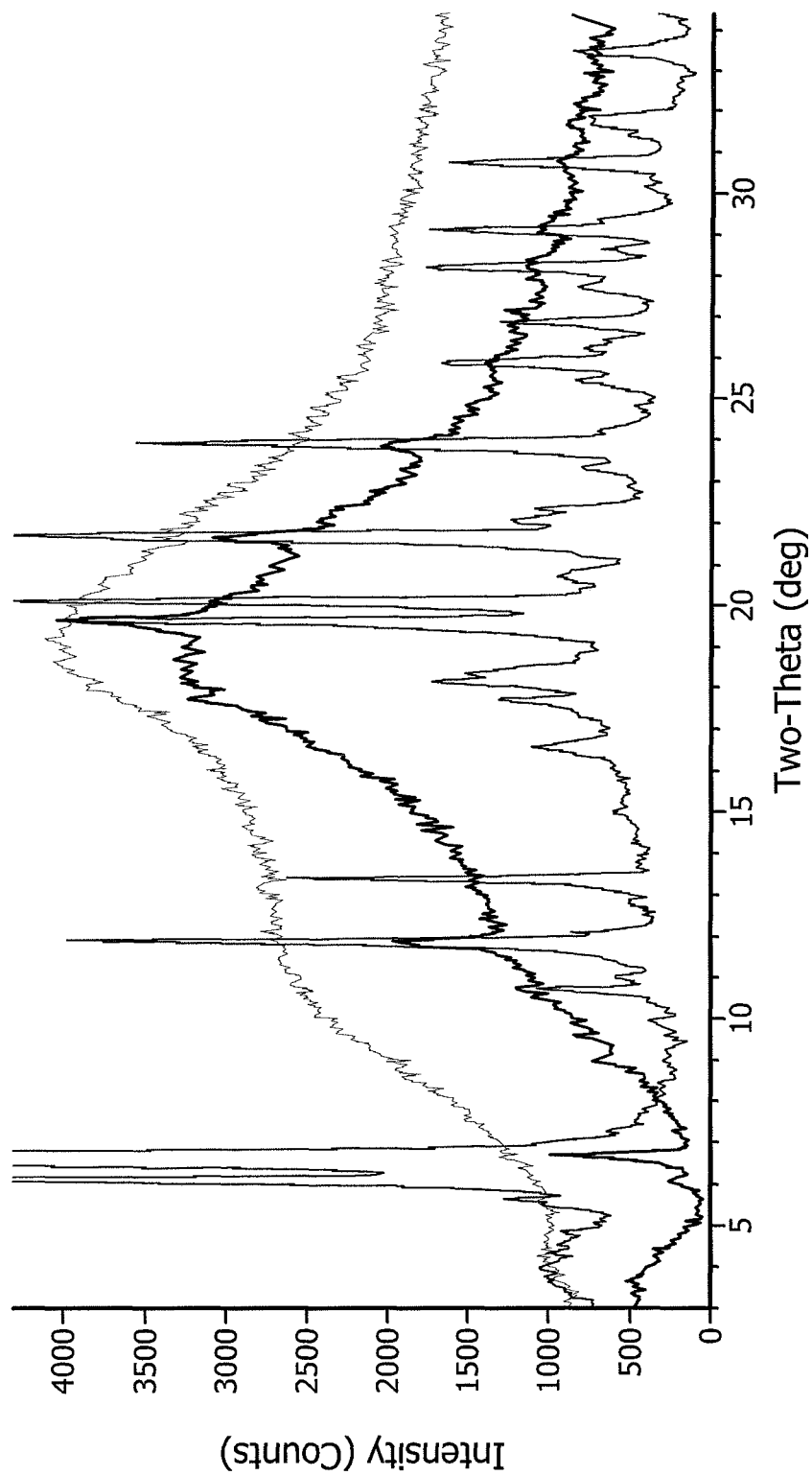
FIG. 39B shows the XRPD of CHLORP AGF SDM formulations. From bottom to top at the 15 Two-Theta mark are shown: NEAT CHLORP, 10% CHLORP AGF SDM, NEAT AGF (crystallinity peaks at 2θ of 6.7°, 11.8°, 19.5°, 20°, 21.6°, 23.8°).

The double melting peak at 127.30 θC and 130.84 θC characteristic of α form of CHLORP was observed in a DSC scan of NEAT CHLOPR (FIG. 39A). DSC thermographs and XRPD diffractograms showed an appreciable amount of drug transformed into amorphous form in CHLORP SDM (FIG. 39B). Thus, the XRPD findings confirm the DSC results. Disorder was observed in the PM formulation as well.

Figure 39C:
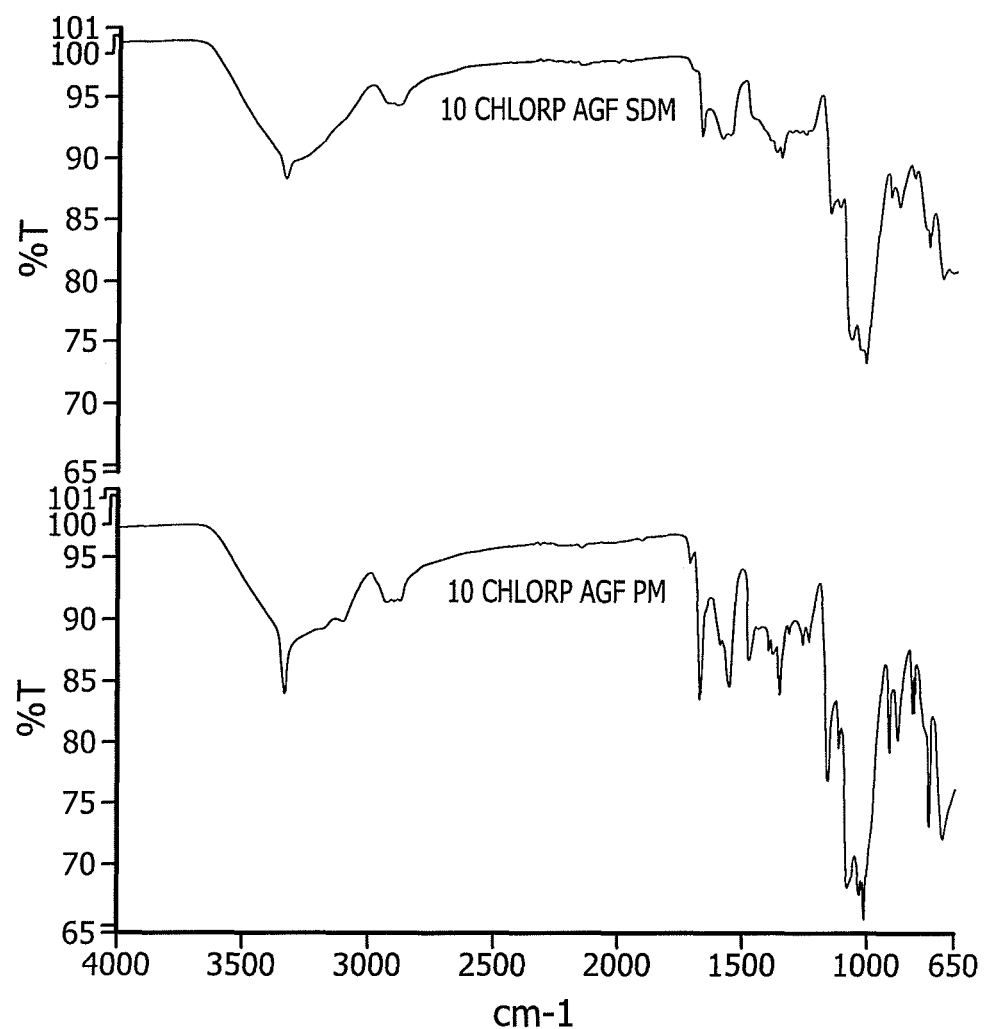
FIG. 39C shows FTIR spectra of 10% CHLORP AGF PM AND 10% CHLORP AGF SDM.
Figure 39D:
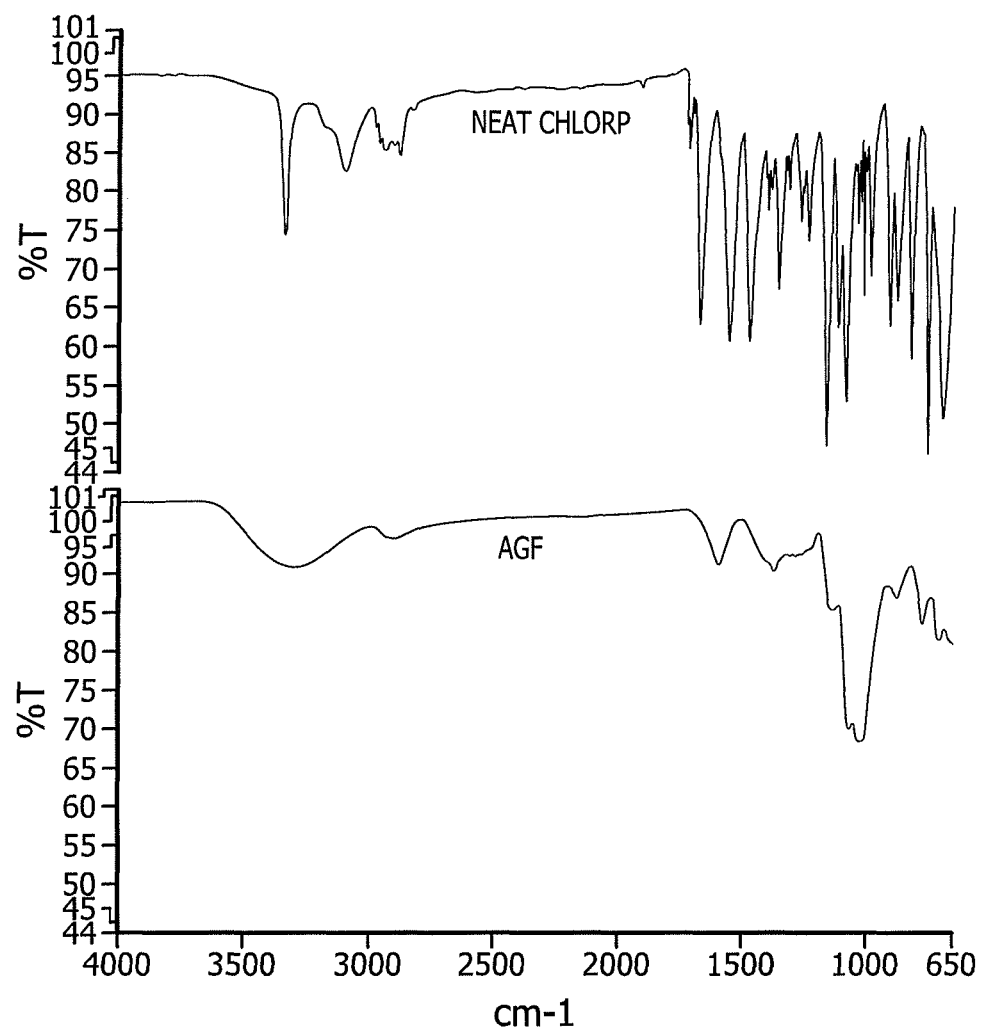
FIG. 39D shows FTIR spectra of NEAT CHLORP and AGF.

Hydrogen bonding between CHLORP and AGF was observed in SDM and PM formulations. The IR band of CHLORP at 1709 cm$^{-1}$ (C=O stretch) either disappeared or was present with less intensity and the IR band at 1666 cm$^{-1}$ (COO$^-$ stretch) shifted to a higher wave number. Similarly the IR band of AGF at 3308 cm$^{-1}$ (OH stretch) was found shifted too (FIGS. 39C and 39D).

Fenoprofen (FENOP)

Figure 40A:
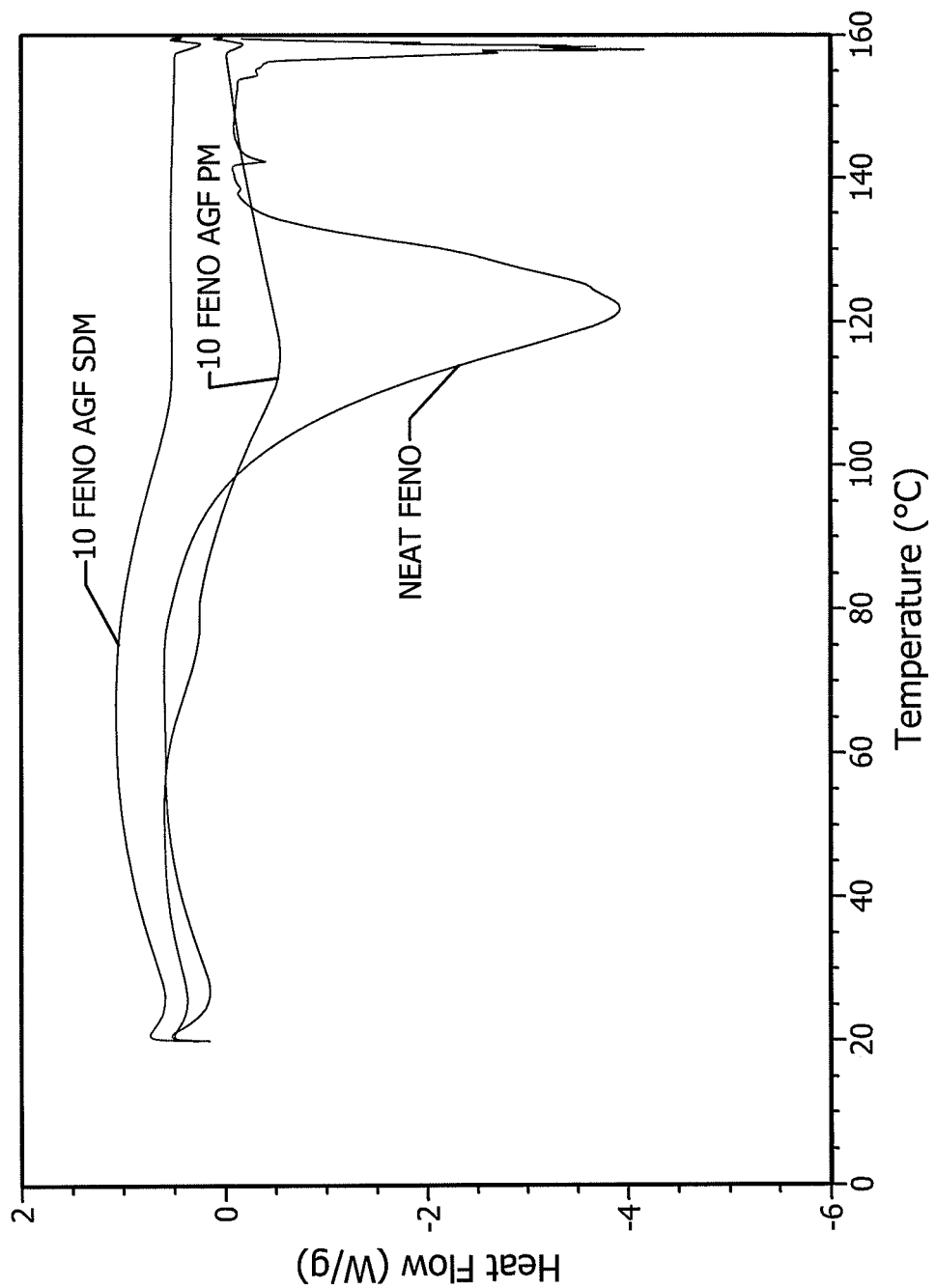
FIG. 40A shows the DSC thermographs of fenoprofen (FENO) AGF PM and FENO AGF SDM. The melting endotherm is at 121.57° C. From bottom to top (at the 120° C. mark) are shown: NEAT FENO, 10% FENO AGF PM and 10% FENO AGF SDM.
Figure 40B:
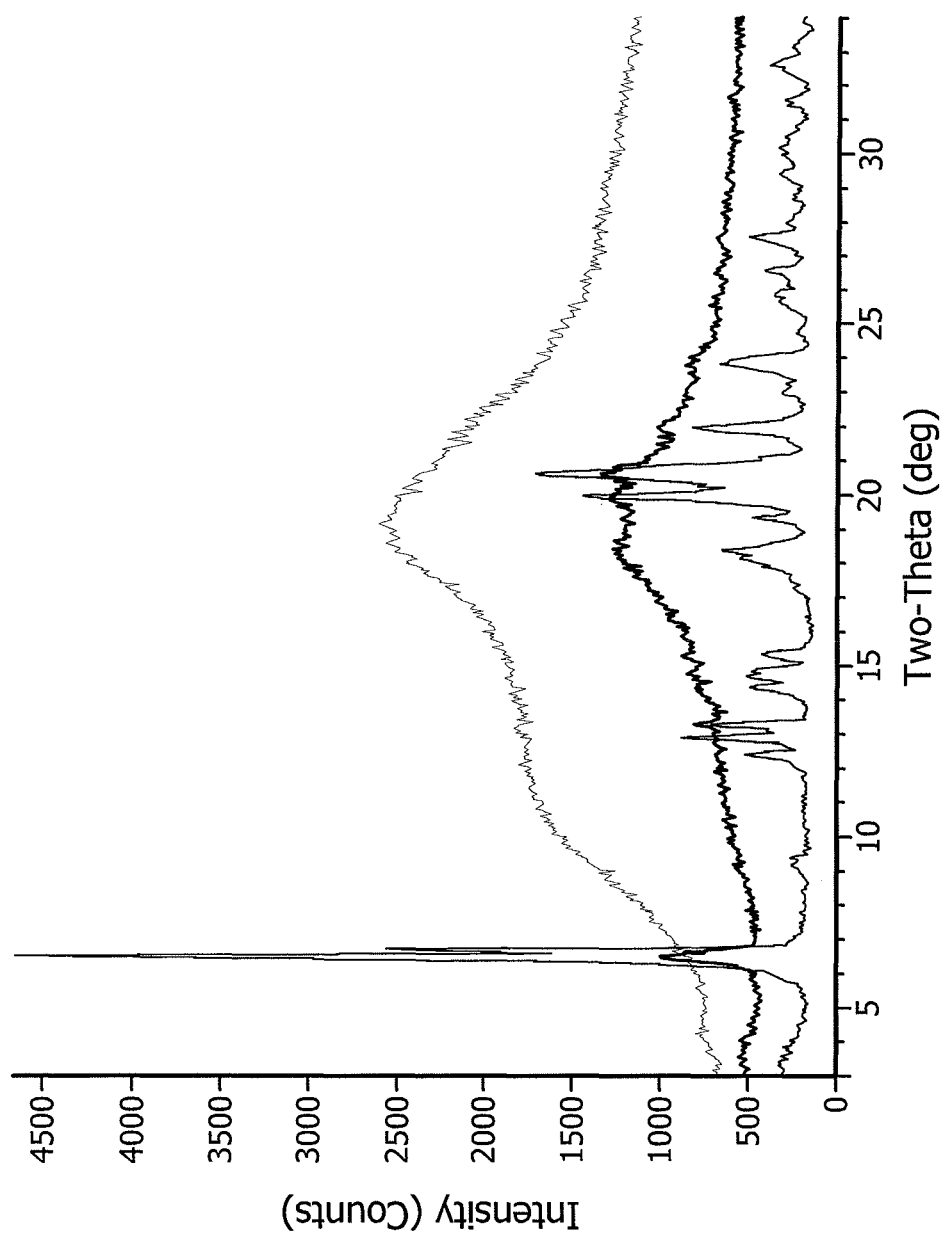
FIG. 40B shows the XRPD of FENO AGF SDM formulations. From bottom to top at the 10 Two-Theta mark are shown: NEAT FENO, 10% FENO AGF SDM, NEAT AGF (crystallinity peaks at 2θ of 6.49°, 19.95°, 20.6°, 21.94°, 23.8°).

FENOP was present in amorphous state in SDM formulation, whereas little disorder was observed in PM formulation. (FIG. 40A). Distinct XRPD peaks at 2θ of 6.49°, 19.95°, 20.6°, 21.94° and 23.8° of FENOP crystallinity were present with significantly reduced intensity in 10% FENO AGF SDM confirming DSC findings of amorphous FENOP in this formulation (FIG. 40B).

The blue shift in 1557 cm$^{-1}$ and 1415 cm$^{-1}$ (COO$^-$ stretch) IR band and red shift AGF OH stretch indicate the existence of hydrogen bonding between these two groups of FENOP and AGF respectively (Table 18).

TABLE 18

Major IR bands of NEAT FENOP and NEAT AGF relevant to interactions in FENOP AGF formulations.

| SAMPLE | FENOP IR BAND 1557 cm$^{-1}$ | FENOP IR BAND 1420 cm$^{-1}$ | AGF IR BAND 3308 cm$^{-1}$ | Hydrogen bonding |
|---|---|---|---|---|
| NEAT FENOP | 1557.90 | 1415.97 | NA | |
| 10% FENOP AGF SDM | 1579.06 | 1419.2 LESS INTENSE | 3292.76 | Yes |
| 10% FENOP AGF PM | 1560.24 | 1416.85 | 3278.61 | Yes |

Figure 41A:
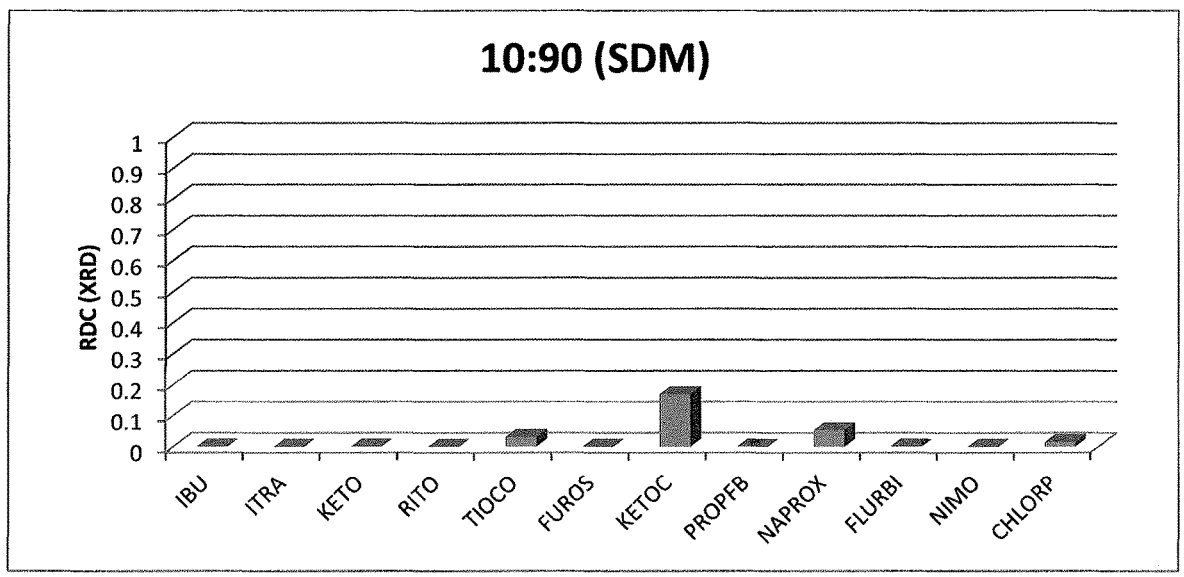
FIG. 41A shows the relative degree of crystallinity (RDC) from XRPD data for SDMs of the indicated drugs at 10% drug loading (Neat drug as a reference; RDC of neat drug is 1).
Figure 41B:
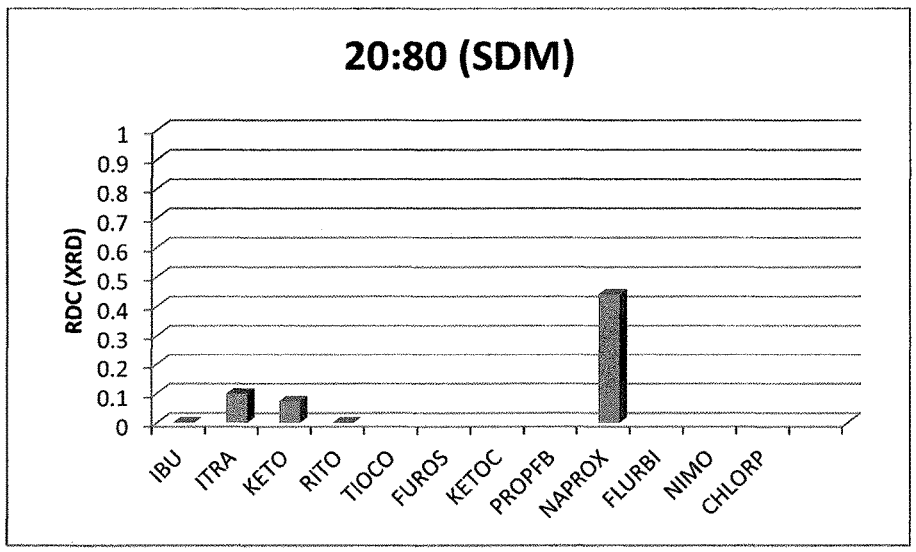
FIG. 41B shows the relative degree of crystallinity (RDC) from XRPD data for 20% drug loading (Neat drug as a reference; RDC of neat drug is 1).
Figure 41C:
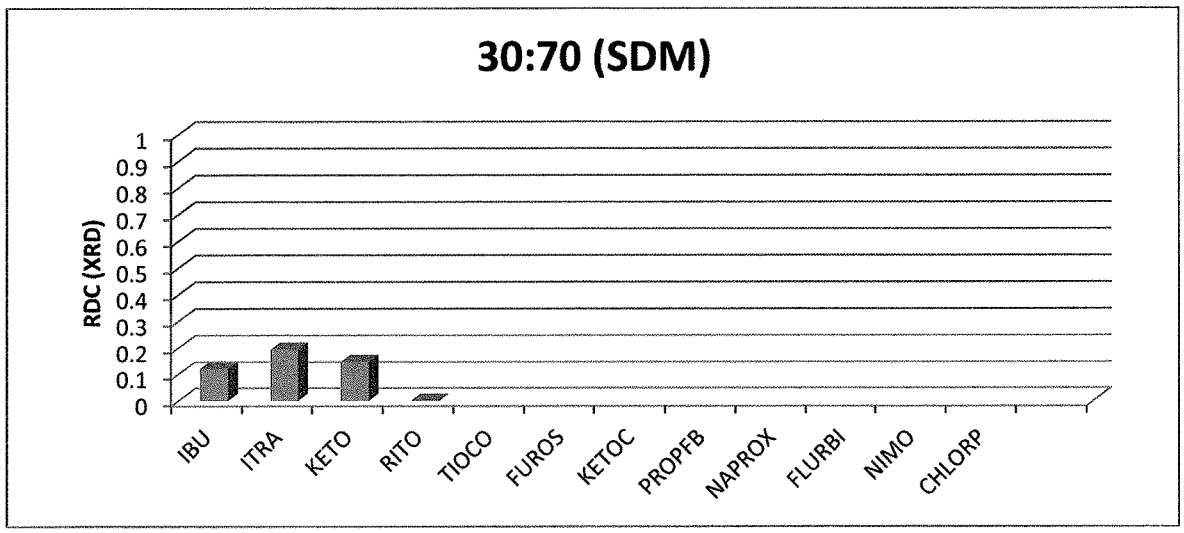
FIG. 41C shows the relative degree of crystallinity (RDC) from XRPD data for 30% drug loading (Neat drug as a reference; RDC of neat drug is 1).

Example 9. Relative Degree of Crystallinity (RDC) and Relative Crystallinity (% RC) of the Various Drugs Tested FIG. 41 A-C shows the RDC for 10%, 20% and 30% DL SD. In FIG. 41 A-D, the drugs on the bar graph that do not have a bar were not tested at those drug loads.

The results are listed in Table 19 and Table 20.

TABLE 19

DSC melting, % relative crystallinity (% RC) for Drug AGF PM and relative degree of crystallinity (RDC) (XRPD) for Drug AGF SDM formulations with NEAT Drug as a reference.

| Drug | Formulation | DSC Tm (θ C.) | % RC by DSC | RDC by XRPD | Note |
|---|---|---|---|---|---|
| RITO | 10% RITO AGF SDM | 0 | — | 0 | (Tm-128.68 θ C.) |
| | 20% RITO AGF SDM | 0 | — | 0 | (XRPD peak at 22.1° 2θ |
| | 30% RITO AGF SDM | 0 | — | 0.016 | used to calculate RDC) |
| | 10% RITO AGF PM | 120.32 | ≥100 | NA | |
| TIOCO | 10% TIOCO AGF SDM | 79.17 | — | 0.031 | (Tm-84.24 θ C.) |
| | 10% TIOCO AGF PM | 78.71 | 83.968 | 0.045 | (XRPD peak at 20.4° 2θ used to calculate RDC) |

TABLE 19-continued

DSC melting, % relative crystallinity (% RC) for Drug AGF PM and relative degree of crystallinity (RDC) (XRPD) for Drug AGF SDM formulations with NEAT Drug as a reference.

| Drug | Formulation | DSC Tm (θ C.) | % RC by DSC | RDC by XRPD | Note |
|---|---|---|---|---|---|
| FUROS | 10% FUROS AGF SDM | 0 | — | 0 | (Tm-228.34 θ C.) |
| | 10% FUROS AGF PM | 236.58 | — | NA | (XRPD peak at 6° 2θ used to calculate RDC) |
| KETOC | 10% KETOC AGF SDM | 148.09 | — | 0.169 | (Tm-150.51 θ C.) |
| | 10% KETOC AGF PM | 149.86 | 87.349 | NA | (XRPD peak at 19.9° 2θ used to calculate RDC) |
| PROPFB | 10% PROPFB AGF SDM | 87.12 | — | 0 | (Tm-95.86 θ C.) |
| | 20% PROPFB AGF SDM | 92.44 | — | NA | (XRPD peak at 10.9° 2θ |
| | 10% PROPFB AGF PM | 90.73 | 92.39 | 0.228 | used to calculate RDC) |
| NAPROX | 10% NAPROX AGF SDM | 0 | — | 0.053 | (Tm-155.53 θ C.) |
| | 20% NAPROX AGF SDM | 150.38 | — | 0.44 | (XRPD peak at 22.25° 2θ |
| | 10% NAPROX AGF PM | 107.76 | ≥100 | NA | used to calculate RDC) |
| FLURBI | 10% FLURB AGF SDM | 0 | — | 0 | (Tm-116.96 θ C.) |
| | 10% FLURB AGF PM | 107.15 | ≥100 | NA | (XRPD peak at 6.49° 2θ used to calculate RDC |
| NIMO | 10% NIMO AGF SDM | 123.98 | — | 0 | (Tm-126.77 θ C.) |
| | 10% NIMO AGF PM | 121.78 | ≥100 | NA | (XRPD peak at 20.2° 2θ used to calculate RDC |
| CHLORP | 10% CHLORP AGF SDM | 115.78 | — | 0.015 | (Tm-118.27 θ C.) |
| | 10% CHLORP AGF PM | 117.82 | ≥100 | NA | (XRPD peak at 6.7° 2θ used to calculate RDC |

A Tm of "0" means that no melting endotherm was present which is suggestive that complete loss of crystallinity was evident.

TABLE 20

DSC melting, % relative crystallinity (% RC) (DSC) for Drug AGF PM and relative degree of crystallinity (RDC) (XRPD) for Drug AGF SDM formulations with Drug as a reference.

| Drug | Formulation | DSC Tm (θ C.) | % Crystallinity by DSC | RDC by XRPD | Note |
|---|---|---|---|---|---|
| IBU | 10% IBU AGF SDM | 0 | — | 0 | (Tm-76.56 θ C.) |
| | 20% IBU AGF SDM | 72.80 | — | 0.219 | (XRPD peak at 22.3° 2θ |
| | 30% IBU AGF SDM | 74.02 | — | 0.120 | used to calculate RDC) |
| | 10% IBU AGF PM | 73.48 | 95.25 | NA | |
| ITRA | 10% ITRA AGF SDM | 0 | — | 0 | (Tm-169.92 θ C.) |
| | 20% ITRA AGF SDM | 167.79 | — | 0.099 | (XRPD peak at 20.4° 2θ |
| | 30% ITRA AGF SDM | 167.66 | — | 0.194 | used to calculate RDC) |
| | 10% ITRA AGF PM | 169.49 | 81.043 | — | |
| KETO | 10% KETO AGF SDM | 0 | — | 0 | (Tm-96.53 θ C. |
| | 20% KETO AGF SDM | 0 | — | 0.073 | (XRPD peak at 22.6° 2θ |
| | 30% KETO AGF SDM | 0 | — | 0.148 | used to calculate RDC |
| | 10% KETO AGF PM | 0 | 0 | — | |

A Tm of "0" means that no melting endotherm was present which is suggestive that complete loss of crystallinity was evident.

At 10% DL SD, KETOC retained an appreciable amount of crystalline drug whereas TIOCO, NAPROX and CHLORP were almost amorphous. At 20% DL SD, NAPROX was partially crystalline, whereas IBU, ITRA and KETO were almost fully amorphous. At 30% DL, only RITO was completely amorphous. Also tested but not shown on FIG. 41 A-C was Fenoprofen, which had a RDC value of 0.125 at 10% DL SD.

Formulations with RDC values determined from XRPD data that were less than 0.17 were designated as amorphous formulations.

Figure 42:
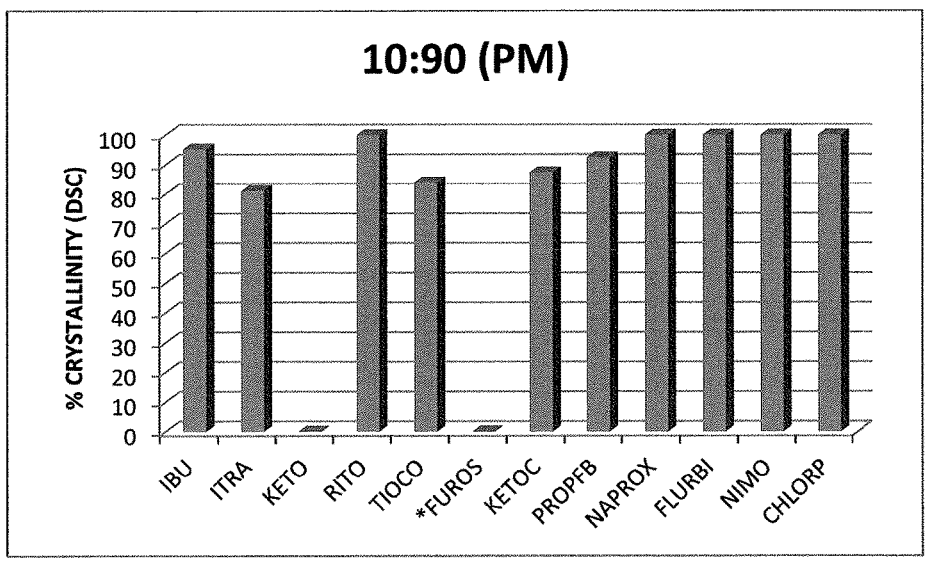
FIG. 42 shows the relative crystallinity (RC) from DSC data for PMs of the indicated drugs at 10% drug loading formulations (% RC of neat drug is 100%); *% crystallinity cannot be calculated for the FUROS PM formulation.

The relative crystallinity (% RC) calculated from the fusion enthalpy of data of the physical mixture and that of pure drug are shown in FIG. 42. All of the drugs were almost crystalline in physical mixture at 1:9 ratio except for KETO.

AGF polymer interacts with drug via the polymer's OH groups. Investigation of the functional groups of the different drugs tested showed that the C=O of carboxylic acid was strongly related to complete crystallization inhibition of drug upon amorphous solid dispersion preparation. Examples of such drugs included IBU, KETO, FLURBI, FUROS and NAPROX. The ester C=O of RITO was related to the existence of an amorphous state as well. The C=O of ITRA and KETOC did not take active part in hydrogen bonding which resulted in the presence of crystalline drug in these formulations. The amide C=O of CHLORP was involved in interaction with AGF polymer and was associated with complete crystallization inhibition but not as extensively as with the C=O of carboxylic acid. Thus the functional groups of the drugs that were found to be related to the formation of an amorphous state of drug in AGF solid dispersion were in the order of C=O of carboxylic acid>C=O of ester>C=O of amide.

AGF polymer was not able to form hydrogen bonding with compounds containing aliphatic ether groups or hydroxyl groups like PROPFB, ITRA, KETOC and TIOCO.

The formation of amorphous AGF solid dispersions with ITRA, TIOCO, PROPFB and KETOC even in the absence of drug polymer hydrogen bonding suggests that the antiplasticizing effect of the AGF polymer was a prominent mechanism in these systems.

In general, acidic polymers are good crystallization inhibitors for basic drugs and basic polymers are good crystallization inhibitors for acidic drugs. However, AGF unexpectedly successfully inhibited the crystallization of acidic (IBU, KETO, NAPROX, FLURBI, CHLORP), basic (RITO, FUROS, ITRA, TIOCO and PROPFB) and neutral (NIMO) drugs in solid dispersions prepared by solvent evaporation. Although glucuronic acid makes AGF slightly acidic, it is comparable to HPMCAS, HPMC on the acid base scale for polymer (PSSA, PAA acidic); (PVP, PVPVA, E100 basic); (HPMC, HPMCAS intermediate).

The polymers with hydrogen bond donor groups (like HPMC and HPMCAS) were better at inhibiting crystallization of the compounds with hydrogen bond acceptor groups like carbonyl etc whereas hydrogen bond acceptor group polymers like PVP, PVP-VA, CrosPVP inhibit the crystallization of the compounds with hydrogen bond donor groups such as carboxyl or hydroxyl. The AGF polymer with hydrogen donor groups has successfully inhibited the crystallization of compounds containing carbonyl groups. Amorphous state formation was not related to the Tg/Tm ratio of the various drugs.

Despite having a slow crystallization tendency, KETOC was partially crystalline in AGF solid dispersion. This can be attributed to the absence of hydrogen bonding between the KETOC and AGF polymer. The presence of crystalline drug in 20 NAPROX AGF SDM formulation even in the presence of carboxylic C=O group can be explained as NAPROX not being a good glass former.

Thus the crystallization inhibition ability of the AGF polymer upon formation of amorphous solid dispersion was found to be governed by the ability of the AGF polymer to form hydrogen bonds with the compound, the antielasticizing effect of the AGF polymer as well as the inherent tendency of the drug to form and stabilize the amorphous form.

The drug loads at which amorphous solid dispersions were formed with comparable carriers were compared to the current findings with AGF and are summarized in Table 21.

TABLE 21

Comparisons of the drug load at which amorphous solid dispersions are formed with AGF polymer, compared to when solid dispersions are formed with commonly used polymers.

| Solid Dispersion | Drug load upto amorphous SD | Detection Technique | Our Findings regarding Drug AGF System |
|---|---|---|---|
| IBU -HPMCK3 | Between 10%-30% | XRPD, DSC | Almost up to 20% |
| IBU- Kollidon | 16% | XRPD, DSC | Almost up to 20% |
| IBU PVPVA | 50% | XRPD, DSC | Almost up to 20% |
| IBU PVP | 15% | XRPD, DSC | Almost up to 20% |
| Itraconazole/ HPMC E5 | 40% | XRPD | Almost up to 20% |
| ITRA-HPMC Coevaporates | Little disorder up to 40% | DSC | Almost 30% |
| ITRA -HPMCE5 melt extrude | 40% | DSC | Almost up to 30% |
| ITRA- PVP film | Upto 40% | DSC | Almost up to 30% |
| ITRA -HPMCAS film | Upto 20% | DSC | Almost up to 30% |
| KETO-PVPK30 co precipitate | Upto 50% | XRPD | Almost up to 30% |
| KETO PVP | Upto 50% | XRPD | Almost up to 30% |
| KETO -Gelucire | Upto 33% | XRPD, DSC | Almost up to 30% |
| RITO -PVPVA | Upto 20% with disso enhancement, could be higher | XRPD | Upto 40% |
| Naproxen- HPMC | 33% (1:2 ratio) | DSC | Partially in 20% DL |
| Naproxen -PVP | 30% | XRPD | Partially in 20% DL |
| KETOC -PVPK25 SPRAYDRY | Upto 10% and upto 10% in PM | XRPD | 10% |
| FLURBI- PVP | Upto 50% | DSC | 10% but could be up to higher DL |
| FLURBI-HPMC | 60% DL | polarized light microscopy | |
| FLURBI-HPMCAS | 50% DL | polarized light microscopy | |
| FLURBI-PVP | 75% DL | polarized light microscopy | |
| DRUG: POLYMER FILM (CHLORP HPMC/ HPMCAS/PVP | 75% DL | polarized light microscopy | Full amorphous at 10% DL can go up to higher DL |
| NIMO- PVP | 25% (1:3 ratio) | DSC, XRPD | Almost upto 10% can go up to higher DL |

The amorphous drug loading capacity of the AGF polymer was found to be comparable for some drugs (ITRA, KETOC, NIMO) and lower for other drugs (KETO, NAPROX, FLURBI) when compared to amorphous drug loading capacity of the commonly used polymer additives. This finding can only be explained by the intermediate placement of AGF polymer on the acid base scale. Surprisingly, slightly acidic AGF polymer was found to be a weak crystallization inhibitor for acidic drugs and therefore requires more polymer to form the amorphous drug. For neutral and basic carriers, on the other hand, AGF acts as a comparable crystallization inhibitor. However, the crystallization inhibition of ketoconazole cannot be explained by the present findings. In sum, it can be concluded that AGF, a novel excipient, is comparable as a solid dispersion carrier to HPMC, HPMCAS and PVP polymers.

AGF polymer was able to inhibit the crystallization of all selected model drugs for the current investigation except KETOC at 10% DL. IBU, ITRA, KETO and RITO were almost fully amorphous at 20% DL and RITO alone was amorphous at 30% and 40% DL in AGF solid dispersions. AGF acted as a drug crystallization inhibitor via forming AGF hydrogen bonds and through AGF's antiplasticizing effect. The crystallization effect of AGF polymer was strong for neutral and basic drugs (except ketoconazole) whereas it was moderate for acidic drugs requiring more AGF polymer to keep the drug in amorphous form. Comparisons of amorphous drug loading of different polymers with AGF polymer have shown that AGF was comparable to HPMC, HPMCAS and PVP.

Example 9. Enhanced Physical Stability of the Solid Dispersions

The RDC was measured by XRPD as described above for the dosage forms listed in Table 22 at various accelerated storage conditions. Batches of IBU AGF SDM, IBU HPMCK3 SDM, IBU HPMCK3 MSD and IBU AGF MSD at 10% drug load and 20% drug load were prepared as described above. In addition, 10% IBU AGF MSD and 10% IBU AGF SDM batches were prepared with 0.02% butylated hydroxytoluene (BHT), an antioxidant. The RDC values were either zero or were significantly lower at 25° C. 60% relative humidity and 40° C. 75% relative humidity storage conditions compared to the initial conditions for both SDM and MSD formulations, suggesting stability of the amorphous IBU. These findings were confirmed by DSC (not shown).

Overall the PM formulations showed enhanced physical stability at 40° C. 75% relative humidity conditions compared to the initial conditions, as evident from the results in Table 22. The RDC was unexpectedly found to be decreased for SDM and MSD formulations. An enhancement in physical stability of the solid dosage forms stored at 40° C. and 0% relative humidity and 40° C. and 75% relative humidity conditions compared to the SD stored at 25° C. and 0% relative humidity and 25° C. and 60% relative humidity was observed. An increase in % amorphous drug in SD under the study conditions was indicative of strong hydrogen bonding between the drug and the polymer.

should be made to the appended claims, rather than to the foregoing specification, as indicating the scope of the invention.

The invention claimed is:

1. A solid dosage form for oral delivery of a therapeutic agent comprising a matrix comprising:
   (i) a structural network formed of a polymer selected from the group consisting of wood species arabinogalactans; and
   (ii) a therapeutic agent dispersed in said polymeric structural network,
   wherein said therapeutic agent is substantially completely amorphous, and
   wherein there is no detectable covalent bonding between the therapeutic agent and the arabinogalactan as determined by Fourier transform infrared spectroscopy (FTIR).

2. The solid dosage form of claim 1 wherein said dosage form is selected from the group consisting of a microsphere, a nano sphere, a powder, a tablet, a film or a pellet enclosed in a capsule.

3. The solid dosage form of claim 1 wherein the relative degree of crystallinity of the therapeutic agent in said dosage form as compared to that of neat therapeutic agent is equal to or less than about 0.20 as measured by X-ray diffraction.

4. The solid dosage form of claim 1 wherein said therapeutic agent is completely amorphous.

5. The solid dosage form of claim 1 wherein said therapeutic agent is a therapeutic agent having low solubility in water and high permeability or a therapeutic agent having low solubility in water and low permeability.

6. The solid dosage form of claim 1 wherein said therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, ketoconazole and furesamide.

TABLE 22

XRPD relative degree of crystallinity (RDC) for IBU AGF formulations with IBU as a reference at different accelerated storage conditions, as a measure of stability (measured at 2θ of 22.4°).

| Formulation | INITIAL | 25° C. and 0% relative humidity (6 Months) | 25° C. and 60% relative humidity (6 Months) | 40° C. and 0% relative humidity (3 Months) | 40° C. and 75% relative humidity (3 Months) |
|---|---|---|---|---|---|
| NEAT IBU | 1 | 1 | 1 | 1 | 1 |
| NEAT AGF | — | — | — | — | — |
| 10% IBU AGF SDM | 0 | 0 | 0 | 0 | 0 |
| 20% IBU AGF SDM | 0.076 | 0.020 | 0.0325 | 0 | 0 |
| 10% IBU AGF SDM 0.02% BHT | 0.049 | 0.016 | 0.019 | 0 | 0 |
| 10% IBU AGF MSD | 0.015 | 0 | 0 | 0 | 0 |
| 20% IBU AGF MSD | 0.046 | 0 | 0.023 | 0 | 0 |
| 10% IBU AGF MSD 0.02% BHT | 0.018 | 0 | 0.022 | 0 | 0 |
| 10% IBU AGF PM | 0.105 | 0 | 0.101 | 0.010 | 0 |
| 10% IBU HPMCK3 SDM | 0 | 0.015 | 0.017 | 0 | 0 |
| 10% IBU HPMCK3 PM | 0.273 | 0.1255 | 0.083 | 0 | 0 |

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference 7. The solid dosage form of claim 1 wherein FTIR shows non-covalent bonding of said therapeutic agent to said polymeric structural network.

8. The solid dosage form of claim 1 wherein said therapeutic agent forms hydrogen bonds to said polymeric structural network.

9. The solid dosage form of claim 1 wherein said dosage form is prepared by dissolving a woody species arabinogalactan in a solvent, followed by emulsion-solvent evaporation of a solvent for said polymeric structural network.

10. The solid dosage form of claim 1 wherein said solid dosage form is prepared by dissolving a woody species arabinogalactan in a solvent, followed by solvent evaporation of a solvent for said matrix comprising said polymeric structural network formed of a polymer consisting of a woody species arabinogalactan.

11. The solid dosage form of claim 1 wherein the relative degree of crystallinity of the therapeutic agent in said solid dosage form as compared to that of neat therapeutic agent after at least 3 months of storage of said solid dosage form is less than the initial relative degree of crystallinity of the therapeutic agent in said solid dosage form as compared to that of neat therapeutic agent.

12. The solid dosage form of claim 1 wherein said arabinogalactan is larch arabinogalactan.

13. A method for preparing a solid dosage form comprising the steps of:
dissolving a therapeutic agent in a solvent to form a first solution of said therapeutic agent;
adding the first solution to a woody species arabinogalactan wet mass to form a second solution; and
evaporating the water and solvent from said second solution to obtain a solid dosage form comprising a matrix comprising: (i) a structural network formed of a polymer selected from the group consisting of wood species arabinogalactans; and (ii) a therapeutic agent dispersed in said polymeric structural network, wherein said therapeutic agent is substantially completely amorphous, and wherein there is no detectable covalent bonding between the therapeutic agent and the arabinogalactan as determined by Fourier transform infrared spectroscopy (FTIR).

14. The method of claim 13 wherein said solid dosage form is a microsphere, a nano sphere or a powder.

15. The method of claim 13 wherein said therapeutic agent is a therapeutic agent having low solubility in water and high permeability or a therapeutic agent having low solubility in water and low permeability.

16. The method of claim 13 wherein said therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, ketoconazole and furesamide.

17. The method of claim 13 wherein FTIR shows non-covalent bonding of said therapeutic agent to said polymeric structural network.

18. The method of claim 13 wherein said therapeutic agent is hydrogen bonded to said polymeric structural network.

19. A method for preparing a solid dosage form comprising the steps of:
mixing a wood species arabinogalactan and a therapeutic agent to form a physical mixture;
adding water to the physical mixture to obtain a wet mass;
adding a solvent to the wet mass to form a solution; and
evaporating the water and solvent from the solution to obtain a solid dosage form comprising a matrix comprising: (i) a structural network formed of a polymer selected from the group consisting of wood species arabinogalactans; and (ii) a therapeutic agent dispersed in said polymeric structural network, wherein said therapeutic agent is substantially completely amorphous, and wherein there is no detectable covalent bonding between the therapeutic agent and the arabinogalactan as determined by Fourier transform infrared spectroscopy (FTIR).

20. The method of claim 19 wherein said solid dosage form is a microsphere, a nano sphere, or a powder.

21. The method of claim 19 wherein said therapeutic agent is a therapeutic agent having low solubility in water and high permeability or a therapeutic agent having low solubility in water and low permeability.

22. The method of claim 19 wherein said therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, ketoconazole and furesamide.

23. The method of claim 19 wherein FTIR shows non-covalent bonding of said therapeutic agent to said polymeric structural network.

24. The method of claim 19 wherein said therapeutic agent is hydrogen bonded to said polymeric structural network.

25. A method for preparing a solid dosage form comprising the steps of:
suspending a therapeutic agent in an aqueous solution of a woody species arabinogalactan to form a solution;
heating said solution near the melting point of said therapeutic agent;
emulsifying the solution with an oil to form a water in oil emulsion; and
evaporating the water from said solution to obtain a solid dosage form comprising a matrix comprising: (i) a structural network formed of a polymer selected from the group consisting of wood species arabinogalactans; and (ii) a therapeutic agent dispersed in said polymeric structural network, wherein said therapeutic agent is substantially completely amorphous, and wherein there is no detectable covalent bonding between the therapeutic agent and the arabinogalactan as determined by Fourier transform infrared spectroscopy (FTIR).

26. The method of claim 25 wherein said solid dosage form is a microsphere, a nano sphere, or a powder.

27. The method of claim 26 wherein said microsphere has a diameter of from about 100 μm to about 500 μm.

28. The method of claim 25 wherein said oil is safflower oil.

29. The method of claim 25 wherein said therapeutic agent is a therapeutic agent having low solubility in water and high permeability or a therapeutic agent having low solubility in water and low permeability.

30. The method of claim 25 wherein said therapeutic agent is selected from the group consisting of ibuprofen, ketoprofen, ritonavir, tioconazole, propranolol free base, flurbiprofen, chlorpropamide, fenoprofen, nimodipine, naproxen, itraconazole, ketoconazole and furesamide.

31. The method of claim 25 wherein FTIR shows non-covalent bonding of said therapeutic agent to said polymeric structural network.

32. The method of claim 25 wherein said therapeutic agent is hydrogen bonded to said polymeric structural network.

33. The solid dosage form of claim 1, wherein said solid dosage form has higher drug dissolution in water at stomach pH compared to the therapeutic agent in neat form.

34. The solid dosage form of claim 33 wherein the dissolution for % drug release at 15 minutes is from about 1.5 fold to about 55 fold compared to the therapeutic agent in neat form.

* * * * *